(12) United States Patent
Giordano et al.

(10) Patent No.: US 7,001,924 B2
(45) Date of Patent: Feb. 21, 2006

(54) INHIBITORS OF RNASE P PROTEINS AS ANTIBACTERIAL COMPOUNDS

(75) Inventors: Tony Giordano, Phoenixville, PA (US); Michael A. Sturgess, Quakertown, PA (US); Samala J. Rao, West Chester, PA (US)

(73) Assignee: Message Pharmaceuticals, Malvern, PA (US)

( * ) Notice: Subject to any disclaimer, the term of this patent is extended or adjusted under 35 U.S.C. 154(b) by 128 days.

(21) Appl. No.: 10/252,945

(22) Filed: Sep. 23, 2002

(65) Prior Publication Data

US 2003/0134904 A1 Jul. 17, 2003

Related U.S. Application Data

(60) Provisional application No. 60/323,853, filed on Sep. 21, 2001.

(51) Int. Cl.
*A61K 31/16* (2006.01)

(52) U.S. Cl. .................. 514/614; 514/616; 514/469; 514/367; 514/467; 514/468; 514/157

(58) Field of Classification Search ................. 514/614, 514/616, 469, 367, 467, 468, 157; 564/147, 564/148, 149, 157; 549/467, 468; 548/157
See application file for complete search history.

(56) References Cited

U.S. PATENT DOCUMENTS

| 2,815,377 A | 12/1957 | Meiser et al. |
|---|---|---|
| 5,238,941 A | 8/1993 | Stanek et al. |
| 5,376,685 A | 12/1994 | Stanek et al. |
| 5,747,508 A | 5/1998 | Richter et al. |
| 6,180,676 B1 * | 1/2001 | Bianchi et al. ............. 514/597 |
| 6,248,787 B1 | 6/2001 | Bianchi et al. |

FOREIGN PATENT DOCUMENTS

| EP | 0 433 526 A1 | 12/1989 |
|---|---|---|
| WO | WO 01/56553 A2 | 8/2001 |
| WO | WO 02/00613 A2 | 1/2002 |

OTHER PUBLICATIONS

Foye, et al, N–Glucopyranosyl–5–aralkylidenerhodanines: Synthesis and Antibacterial and Antiviral Activities., Journal of Pharmaceutical Sciences, 1977, 66:1607–1611.

Korytnyk, et al, Guanylhydrazones with Potential Antileukemic Activity. 2. Synthesis and Structure–Activity Relationships of Analogues of 4,4'–Diacetyl–N,N'–diphenylurea Bis (guanylhydrazone), Journal of Medicinal Chemistry, 1978, 21:507–513.

Magdolen, et al. Synthesis, Antimicrobial Testing and QSAR Study of New 2–phenylethenylbenzothiazolium Salts Substituted by Cyclic Amines, Pharmazie, 2000, 55:803–810.

* cited by examiner

*Primary Examiner*—Shailendra Kumar
(74) *Attorney, Agent, or Firm*—Clark & Elbing LLP; Kristina Bieker-Brady P.C.

(57) ABSTRACT

The present invention features compounds useful for inhibiting RNase P activity. These compounds can be used as therapeutics for treating or preventing a variety of bacterial infections. The compounds belong to several classes including mono- and bis-guanylhydrazones, guanylhydrazone mimetics, and benzothiazolium compounds. Exemplary compounds are compounds of formula I:

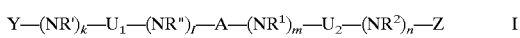

$$Y-(NR')_k-U_1-(NR'')_r-A-(NR^1)_m-U_2-(NR^2)_n-Z \qquad I$$

with substituents as described herein.

27 Claims, 30 Drawing Sheets

Figure 3.

| MES ID | Assay name | Concentration μM | Experimental Value |
|---|---|---|---|
| 10608 | N. gonorrhea MTS Bacterial Growth | 1 | 69.7 |
| 10608 | N. gonorrhea MTS Bacterial Growth | 3 | 76.8 |
| 10608 | N. gonorrhea MTS Bacterial Growth | 10 | 76.3 |
| 10608 | E. coli Bacterial Growth | 1 | 71.8 |
| 10608 | E. coli Bacterial Growth | 3 | 99.8 |
| 10608 | E. coli Bacterial Growth | 10 | 97.7 |
| 10608 | S. aureus Bacterial Growth | 1 | 95.6 |
| 10608 | S. aureus Bacterial Growth | 3 | 91.1 |
| 10608 | S. aureus Bacterial Growth | 10 | 83.2 |
| 10608 | S. pyogenes Bacterial Growth | 1 | 99.9 |
| 10608 | S. pyogenes Bacterial Growth | 3 | 44.9 |
| 10608 | S. pyogenes Bacterial Growth | 10 | 45.2 |
| 10608 | RNase P TRF Dose Response | 10 | 0.9 |
| 10608 | RNase P TRF Dose Response | 3 | 68.6 |
| 10608 | RNase P TRF Dose Response | 1 | 86.5 |
| 10608 | RNase P TRF Dose Response | 0.3 | 96.1 |
| 10608 | S. aureus Bacterial Growth | 10 | 57.7 |
| 10608 | S. aureus Bacterial Growth | 3 | 89.2 |
| 10608 | S. aureus Bacterial Growth | 1 | 97.6 |
| 10608 | E. coli Bacterial Growth | 10 | 103.5 |
| 10608 | E. coli Bacterial Growth | 3 | 100.7 |
| 10608 | E. coli Bacterial Growth | 1 | 101.8 |
| 10608 | S. pyogenes Bacterial Growth | 10 | 7.2 |
| 10608 | S. pyogenes Bacterial Growth | 3 | 7.3 |
| 10608 | S. pyogenes Bacterial Growth | 1 | 76.5 |
| 10608 | N. gonorrhea MTS Bacterial Growth | 10 | 114.3 |
| 10608 | N. gonorrhea MTS Bacterial Growth | 3 | 90.8 |
| 10608 | N. gonorrhea MTS Bacterial Growth | 1 | 121.3 |
| 10608 | S. aureus Bacterial Growth | 10 | 82.3 |
| 10608 | S. aureus Bacterial Growth | 3 | 98.6 |
| 10608 | S. aureus Bacterial Growth | 1 | 95.5 |
| 10608 | E. coli Bacterial Growth | 10 | 98.1 |
| 10608 | E. coli Bacterial Growth | 3 | 98.9 |
| 10608 | E. coli Bacterial Growth | 1 | 96.7 |
| 10608 | S. pyogenes Bacterial Growth | 10 | 0.1 |
| 10608 | S. pyogenes Bacterial Growth | 3 | -1 |
| 10608 | S. pyogenes Bacterial Growth | 1 | 57.9 |
| 10608 | MCF-7 110 6D-2 24 hour MTS Toxicity | 1 | 109.7 |
| 10608 | MCF-7 110 6D-2 24 hour MTS Toxicity | 3 | 108.6 |

Figure 3.

| MES ID | Assay name | Concentration μM | Experimental Value |
|---|---|---|---|
| 10608 | MCF-7 110 6D-2 24 hour MTS Toxicity | 10 | 99.5 |
| 10608 | PBMC 24 hour MTS Toxicity | 1 | 97.7 |
| 10608 | PBMC 24 hour MTS Toxicity | 3 | 101.4 |
| 10608 | PBMC 24 hour MTS Toxicity | 10 | 86.1 |
| 10608 | RNase P TRF Dose Response | 0.3 | 91.8 |
| 10608 | RNase P TRF Dose Response | 1 | 81.9 |
| 10608 | RNase P TRF Dose Response | 3 | 66.4 |
| 10608 | RNase P TRF Dose Response | 10 | 84.9 |
| 10608 | RNase P TRF Dose Response | 0.3 | 94.2 |
| 10608 | RNase P TRF Dose Response | 1 | 82.1 |
| 10608 | RNase P TRF Dose Response | 3 | 56.2 |
| 10608 | RNase P TRF Dose Response | 10 | -6 |
| 10608 | PBMC 24 hour MTS Toxicity | 1 | 112.3 |
| 10608 | PBMC 24 hour MTS Toxicity | 3 | 132.9 |
| 10608 | PBMC 24 hour MTS Toxicity | 10 | 96.1 |
| 10609 | N. gonorrhea MTS Bacterial Growth | 1 | 101 |
| 10609 | N. gonorrhea MTS Bacterial Growth | 3 | 71.9 |
| 10609 | N. gonorrhea MTS Bacterial Growth | 10 | 64 |
| 10609 | E. coli Bacterial Growth | 1 | 100.8 |
| 10609 | E. coli Bacterial Growth | 3 | 95.4 |
| 10609 | E. coli Bacterial Growth | 10 | 100.3 |
| 10609 | S. aureus Bacterial Growth | 1 | 100.9 |
| 10609 | S. aureus Bacterial Growth | 3 | 104.8 |
| 10609 | S. aureus Bacterial Growth | 10 | 100.6 |
| 10609 | S. pyogenes Bacterial Growth | 1 | 101.5 |
| 10609 | S. pyogenes Bacterial Growth | 3 | 98.2 |
| 10609 | S. pyogenes Bacterial Growth | 10 | 98.3 |
| 10609 | RNase P TRF Dose Response | 10 | 62.3 |
| 10609 | RNase P TRF Dose Response | 3 | 92.3 |
| 10609 | RNase P TRF Dose Response | 1 | 101.6 |
| 10609 | RNase P TRF Dose Response | 0.3 | 96.5 |
| 10609 | S. aureus Bacterial Growth | 10 | 91.7 |
| 10609 | S. aureus Bacterial Growth | 3 | 90.5 |
| 10609 | S. aureus Bacterial Growth | 1 | 98.6 |
| 10609 | E. coli Bacterial Growth | 10 | 99.4 |
| 10609 | E. coli Bacterial Growth | 3 | 98.9 |
| 10609 | E. coli Bacterial Growth | 1 | 99.5 |
| 10609 | S. pyogenes Bacterial Growth | 10 | 11 |
| 10609 | S. pyogenes Bacterial Growth | 3 | 94.1 |

Figure 3.

| MES ID | Assay name | Concentration μM | Experimental Value |
|---|---|---|---|
| 10609 | S. pyogenes Bacterial Growth | 1 | 97 |
| 10609 | N. gonorrhea MTS Bacterial Growth | 10 | 50.8 |
| 10609 | N. gonorrhea MTS Bacterial Growth | 3 | 90.2 |
| 10609 | N. gonorrhea MTS Bacterial Growth | 1 | 102.5 |
| 10609 | S. aureus Bacterial Growth | 10 | 92 |
| 10609 | S. aureus Bacterial Growth | 3 | 92.9 |
| 10609 | S. aureus Bacterial Growth | 1 | 99.4 |
| 10609 | E. coli Bacterial Growth | 10 | 97.5 |
| 10609 | E. coli Bacterial Growth | 3 | 97 |
| 10609 | E. coli Bacterial Growth | 1 | 97 |
| 10609 | S. pyogenes Bacterial Growth | 10 | 17.6 |
| 10609 | S. pyogenes Bacterial Growth | 3 | 82.4 |
| 10609 | S. pyogenes Bacterial Growth | 1 | 89 |
| 10609 | MCF-7 110 6D-2 24 hour MTS Toxicity | 1 | 111.8 |
| 10609 | MCF-7 110 6D-2 24 hour MTS Toxicity | 3 | 109.9 |
| 10609 | MCF-7 110 6D-2 24 hour MTS Toxicity | 10 | 97.6 |
| 10609 | PBMC 24 hour MTS Toxicity | 1 | 91.3 |
| 10609 | PBMC 24 hour MTS Toxicity | 3 | 103.2 |
| 10609 | PBMC 24 hour MTS Toxicity | 10 | 84.2 |
| 10609 | RNase P TRF Dose Response | 0.3 | 82.8 |
| 10609 | RNase P TRF Dose Response | 1 | 85.7 |
| 10609 | RNase P TRF Dose Response | 3 | 85.4 |
| 10609 | RNase P TRF Dose Response | 10 | 65 |
| 10609 | RNase P TRF Dose Response | 0.3 | 94.9 |
| 10609 | RNase P TRF Dose Response | 1 | 91 |
| 10609 | RNase P TRF Dose Response | 3 | 83.2 |
| 10609 | RNase P TRF Dose Response | 10 | 42.2 |
| 10609 | PBMC 24 hour MTS Toxicity | 1 | 117.8 |
| 10609 | PBMC 24 hour MTS Toxicity | 3 | 114 |
| 10609 | PBMC 24 hour MTS Toxicity | 10 | 104.2 |
| 32029 | RNase P ECL Dose Response | 10 | 46.1 |
| 32029 | RNase P ECL Dose Response | 3 | 90.2 |
| 32029 | RNase P ECL Dose Response | 1 | 107.6 |
| 32029 | RNase P ECL Dose Response | 0.3 | 113 |
| 32029 | N. gonorrhea MTS Bacterial Growth | 1 | 82.7 |
| 32029 | N. gonorrhea MTS Bacterial Growth | 3 | 69.3 |
| 32029 | N. gonorrhea MTS Bacterial Growth | 10 | 76.5 |
| 32029 | N. gonorrhea MTS Bacterial Growth | 1 | 103.4 |
| 32029 | N. gonorrhea MTS Bacterial Growth | 3 | 94.1 |

Figure 3.

| MES ID | Assay name | Concentration μM | Experimental Value |
|---|---|---|---|
| 32029 | N. gonorrhea MTS Bacterial Growth | 10 | 102.1 |
| 32029 | S. aureus Bacterial Growth | 1 | 90.7 |
| 32029 | S. aureus Bacterial Growth | 3 | 72.8 |
| 32029 | S. aureus Bacterial Growth | 10 | 96 |
| 32029 | S. pyogenes Bacterial Growth | 1 | 97.6 |
| 32029 | S. pyogenes Bacterial Growth | 3 | 101.1 |
| 32029 | S. pyogenes Bacterial Growth | 10 | 104.2 |
| 32029 | E. coli Bacterial Growth | 1 | 84.9 |
| 32029 | E. coli Bacterial Growth | 3 | 84.6 |
| 32029 | E. coli Bacterial Growth | 10 | 86 |
| 32029 | E. coli Bacterial Growth | 1 | 79.8 |
| 32029 | E. coli Bacterial Growth | 3 | 78.7 |
| 32029 | E. coli Bacterial Growth | 10 | 75 |
| 32029 | S. pyogenes Bacterial Growth | 1 | 100.7 |
| 32029 | S. pyogenes Bacterial Growth | 3 | 97.9 |
| 32029 | S. pyogenes Bacterial Growth | 10 | 102.4 |
| 32029 | S. aureus Bacterial Growth | 1 | 86.6 |
| 32029 | S. aureus Bacterial Growth | 3 | 83.4 |
| 32029 | S. aureus Bacterial Growth | 10 | 87.5 |
| 32029 | RNase P ECL Dose Response | 10 | 102 |
| 32029 | RNase P ECL Dose Response | 3 | 98.3 |
| 32029 | RNase P ECL Dose Response | 1 | 104.1 |
| 32029 | RNase P ECL Dose Response | 0.3 | 135 |
| 32029 | RNase P ECL Dose Response | 10 | 106.9 |
| 32029 | RNase P ECL Dose Response | 3 | 110.8 |
| 32029 | RNase P ECL Dose Response | 1 | 113 |
| 32029 | RNase P ECL Dose Response | 0.3 | 115 |
| 32029 | RNase P TRF Dose Response | 0.3 | 102.1 |
| 32029 | RNase P TRF Dose Response | 1 | 85.8 |
| 32029 | RNase P TRF Dose Response | 3 | 78.7 |
| 32029 | RNase P TRF Dose Response | 10 | 58.7 |
| 32029 | RNase P TRF Dose Response | 0.3 | 96.5 |
| 32029 | RNase P TRF Dose Response | 1 | 66.6 |
| 32029 | RNase P TRF Dose Response | 3 | 55 |
| 32029 | RNase P TRF Dose Response | 10 | 36.7 |
| 32198 | RNase P ECL Dose Response | 10 | 32.8 |
| 32198 | RNase P ECL Dose Response | 3 | 95.3 |
| 32198 | RNase P ECL Dose Response | 1 | 97.8 |
| 32198 | RNase P ECL Dose Response | 0.3 | 97.6 |

Figure 3.

| MES ID | Assay name | Concentration μM | Experimental Value |
|---|---|---|---|
| 32198 | N. gonorrhoeae MTS Bacterial Growth | 1 | 35.4 |
| 32198 | N. gonorrhoeae MTS Bacterial Growth | 3 | 66.1 |
| 32198 | N. gonorrhoeae MTS Bacterial Growth | 10 | 76.3 |
| 32198 | N. gonorrhoeae MTS Bacterial Growth | 1 | 86.1 |
| 32198 | N. gonorrhoeae MTS Bacterial Growth | 3 | 107 |
| 32198 | N. gonorrhoeae MTS Bacterial Growth | 10 | 102.7 |
| 32198 | S. aureus Bacterial Growth | 1 | 95.2 |
| 32198 | S. aureus Bacterial Growth | 3 | 83.9 |
| 32198 | S. aureus Bacterial Growth | 10 | 69.6 |
| 32198 | S. pyogenes Bacterial Growth | 1 | 105.5 |
| 32198 | S. pyogenes Bacterial Growth | 3 | 121.9 |
| 32198 | S. pyogenes Bacterial Growth | 10 | 117.4 |
| 32198 | E. coli Bacterial Growth | 1 | 95.5 |
| 32198 | E. coli Bacterial Growth | 3 | 95 |
| 32198 | E. coli Bacterial Growth | 10 | 92.3 |
| 32198 | E. coli Bacterial Growth | 1 | 99.5 |
| 32198 | E. coli Bacterial Growth | 3 | 76.7 |
| 32198 | E. coli Bacterial Growth | 10 | 100.1 |
| 32198 | S. pyogenes Bacterial Growth | 1 | 103.7 |
| 32198 | S. pyogenes Bacterial Growth | 3 | 99.7 |
| 32198 | S. pyogenes Bacterial Growth | 10 | 101.1 |
| 32198 | S. aureus Bacterial Growth | 1 | 108.1 |
| 32198 | S. aureus Bacterial Growth | 3 | 88.7 |
| 32198 | S. aureus Bacterial Growth | 10 | 82.6 |
| 32198 | RNase P TRF Dose Response | 0.3 | 98.3 |
| 32198 | RNase P TRF Dose Response | 1 | 91.4 |
| 32198 | RNase P TRF Dose Response | 3 | 85.6 |
| 32198 | RNase P TRF Dose Response | 10 | 58.1 |
| 32198 | RNase P TRF Dose Response | 0.3 | 98.9 |
| 32198 | RNase P TRF Dose Response | 1 | 90.9 |
| 32198 | RNase P TRF Dose Response | 3 | 65.9 |
| 32198 | RNase P TRF Dose Response | 10 | 17.7 |
| 32198 | PBMC Toxicity Low-LPS-Induced | 1 | 107.2 |
| 32198 | PBMC Toxicity Low-LPS-Induced | 3 | 105 |
| 32198 | PBMC Toxicity Low-LPS-Induced | 10 | 99.7 |
| 10635 | N. gonorrhoeae MTS Bacterial Growth | 1 | 75.1 |
| 10635 | N. gonorrhoeae MTS Bacterial Growth | 3 | 83.2 |
| 10635 | N. gonorrhoeae MTS Bacterial Growth | 10 | 85.5 |
| 10635 | S. aureus Bacterial Growth | 1 | 85 |

Figure 3.

| MES ID | Assay name | Concentration μM | Experimental Value |
|---|---|---|---|
| 10635 | S. aureus Bacterial Growth | 3 | 67.3 |
| 10635 | S. aureus Bacterial Growth | 10 | 0.9 |
| 10635 | E. coli Bacterial Growth | 1 | 101.4 |
| 10635 | E. coli Bacterial Growth | 3 | 103.9 |
| 10635 | E. coli Bacterial Growth | 10 | 102.3 |
| 10635 | S. pyogenes Bacterial Growth | 1 | 103.1 |
| 10635 | S. pyogenes Bacterial Growth | 3 | 97 |
| 10635 | S. pyogenes Bacterial Growth | 10 | -2.6 |
| 10635 | RNase P TRF Dose Response | 1 | 107 |
| 10635 | RNase P TRF Dose Response | 3 | 98.7 |
| 10635 | RNase P TRF Dose Response | 10 | 89.5 |
| 10635 | RNase P TRF Dose Response | 30 | 13.7 |
| 10635 | RNase P TRF Dose Response | 1 | 110.2 |
| 10635 | RNase P TRF Dose Response | 3 | 100.3 |
| 10635 | RNase P TRF Dose Response | 10 | 38.8 |
| 10635 | RNase P TRF Dose Response | 30 | -132.3 |
| 10635 | RNase P TRF Dose Response | 0.3 | 100.8 |
| 10635 | RNase P TRF Dose Response | 1 | 99.2 |
| 10635 | RNase P TRF Dose Response | 3 | 95 |
| 10635 | RNase P TRF Dose Response | 10 | 61.2 |
| 10635 | RNase P TRF Dose Response | 30 | -12.9 |
| 10636 | RNase P TRF Dose Response | 1 | 94.3 |
| 10636 | RNase P TRF Dose Response | 3 | 90.2 |
| 10636 | RNase P TRF Dose Response | 10 | 87.6 |
| 10636 | RNase P TRF Dose Response | 30 | 84.5 |
| 10636 | RNase P TRF Dose Response | 1 | 95.4 |
| 10636 | RNase P TRF Dose Response | 3 | 75.4 |
| 10636 | RNase P TRF Dose Response | 10 | 30.9 |
| 10636 | RNase P TRF Dose Response | 30 | -18.4 |
| 10636 | RNase P TRF Dose Response | 0.3 | 100.8 |
| 10636 | RNase P TRF Dose Response | 1 | 98.7 |
| 10636 | RNase P TRF Dose Response | 3 | 90.4 |
| 10636 | RNase P TRF Dose Response | 10 | 61.9 |
| 10636 | RNase P TRF Dose Response | 30 | 28.2 |
| 10636 | N. gonorrhoeae MTS Bacterial Growth | 1 | 94.7 |
| 10636 | N. gonorrhoeae MTS Bacterial Growth | 3 | 111.2 |
| 10636 | N. gonorrhoeae MTS Bacterial Growth | 10 | 88.6 |
| 10636 | S. aureus Bacterial Growth | 1 | 100.6 |
| 10636 | S. aureus Bacterial Growth | 3 | 94.3 |

Figure 3.

| MES ID | Assay name | Concentration μM | Experimental Value |
|---|---|---|---|
| 10636 | S. aureus Bacterial Growth | 10 | 0.1 |
| 10636 | E. coli Bacterial Growth | 1 | 101.7 |
| 10636 | E. coli Bacterial Growth | 3 | 103.4 |
| 10636 | E. coli Bacterial Growth | 10 | 106.4 |
| 10636 | S. pyogenes Bacterial Growth | 1 | 100.2 |
| 10636 | S. pyogenes Bacterial Growth | 3 | 102.6 |
| 10636 | S. pyogenes Bacterial Growth | 10 | 101.8 |
| 10609 | N. gonorrhoeae MTS Bacterial Growth | 1 | 100.8 |
| 10609 | N. gonorrhoeae MTS Bacterial Growth | 3 | 100.5 |
| 10609 | N. gonorrhoeae MTS Bacterial Growth | 10 | 95.8 |
| 10623 | N. gonorrhoeae MTS Bacterial Growth | 1 | 80.5 |
| 10623 | N. gonorrhoeae MTS Bacterial Growth | 3 | 90.8 |
| 10623 | N. gonorrhoeae MTS Bacterial Growth | 10 | 109.6 |
| 10624 | N. gonorrhoeae MTS Bacterial Growth | 1 | 93.1 |
| 10624 | N. gonorrhoeae MTS Bacterial Growth | 3 | 105.3 |
| 10624 | N. gonorrhoeae MTS Bacterial Growth | 10 | 119.5 |
| 10629 | N. gonorrhoeae MTS Bacterial Growth | 1 | 83.5 |
| 10629 | N. gonorrhoeae MTS Bacterial Growth | 3 | 86.7 |
| 10629 | N. gonorrhoeae MTS Bacterial Growth | 10 | 78.1 |
| 10609 | S. aureus Bacterial Growth | 1 | 96.4 |
| 10609 | S. aureus Bacterial Growth | 3 | 96.9 |
| 10609 | S. aureus Bacterial Growth | 10 | 82.2 |
| 10623 | S. aureus Bacterial Growth | 1 | 90 |
| 10623 | S. aureus Bacterial Growth | 3 | 91.4 |
| 10623 | S. aureus Bacterial Growth | 10 | 85.4 |
| 10624 | S. aureus Bacterial Growth | 1 | 95.7 |
| 10624 | S. aureus Bacterial Growth | 3 | 94.8 |
| 10624 | S. aureus Bacterial Growth | 10 | 88.4 |
| 10629 | S. aureus Bacterial Growth | 1 | 87 |
| 10629 | S. aureus Bacterial Growth | 3 | 87.8 |
| 10629 | S. aureus Bacterial Growth | 10 | 50 |
| 10609 | E. coli Bacterial Growth | 1 | 103.2 |
| 10609 | E. coli Bacterial Growth | 3 | 103.7 |
| 10609 | E. coli Bacterial Growth | 10 | 102.2 |
| 10623 | E. coli Bacterial Growth | 1 | 104.1 |
| 10623 | E. coli Bacterial Growth | 3 | 104 |
| 10623 | E. coli Bacterial Growth | 10 | 104.2 |
| 10624 | E. coli Bacterial Growth | 1 | 103.9 |
| 10624 | E. coli Bacterial Growth | 3 | 104.1 |

Figure 3.

| MES ID | Assay name | Concentration μM | Experimental Value |
|---|---|---|---|
| 10624 | E. coli Bacterial Growth | 10 | 104.2 |
| 10629 | E. coli Bacterial Growth | 1 | 103.4 |
| 10629 | E. coli Bacterial Growth | 3 | 104 |
| 10629 | E. coli Bacterial Growth | 10 | 100.4 |
| 10609 | S. pyogenes Bacterial Growth | 1 | 101.8 |
| 10609 | S. pyogenes Bacterial Growth | 3 | 104.7 |
| 10609 | S. pyogenes Bacterial Growth | 10 | 4.8 |
| 10623 | S. pyogenes Bacterial Growth | 1 | 103.4 |
| 10623 | S. pyogenes Bacterial Growth | 3 | 99.8 |
| 10623 | S. pyogenes Bacterial Growth | 10 | -1.5 |
| 10624 | S. pyogenes Bacterial Growth | 1 | 98 |
| 10624 | S. pyogenes Bacterial Growth | 3 | 100.6 |
| 10624 | S. pyogenes Bacterial Growth | 10 | 9.3 |
| 10629 | S. pyogenes Bacterial Growth | 1 | 101.5 |
| 10629 | S. pyogenes Bacterial Growth | 3 | 103.9 |
| 10629 | S. pyogenes Bacterial Growth | 10 | 98.4 |

*Streptococcus mutans* UAB159 (119 aa)
Amino acid sequence: SEQ ID NO. 20
VLKKAYRVKSDKDFQAIFTEGRSVANRKFVVYSLEKDQSHYRVGLSVGKRLGNAVVRNAIKRKLRHVLMELGPYLGT
QDFVVIARKGVEELDYSTMKKNLVHVLKLAKLYQEGSIREKE
Nucleotide sequence (plus strand): SEQ ID NO. 1
AGATTTTGGCTTTTCTCATTTATGATATAATAGTGATAATTAAATATTGGAGTCATGTTTGAAAAAGCCTA
TCGCGTTAAAAGTGATAAAGATTTTCAGGCAATTTTCACTGAAGGACGAAGTGTTGCCAATCGGAAATTGTTGTCT
ATAGTTTAGAAAAAGATCAAAGTCACTATCGTGTTGGACTTTCAGTTGGAAAAAGATTAGGAAATGCTGTCGTTAGA
AATGCGATTAAACGAAAATTGCGCCATGTCCTTATGGAACTGGTCCTTATTGGCACTCAAGATTTGTGTTAT
TGCTAGAAAAGGTGTTGAGGAACTTGATTATAGCACGATGAAAAAAATCTGTTCATGTTTAAAACTGGCTAAAC
TGTATCAGGAAGGATCTATTCGTGAAAAGAA
Sequence origin: University of Oklahoma ACGT; Contig 299

FIG. 5B

*Klebsiella pneumoniae* M6H 78578 (119 aa)
Amino acid sequence: SEQ ID NO. 21
VVKLAFPRELRLLTPSHFTFVFQQPQRAGTPQITILGRLNSLGHPRIGLTVAKKNVKRAHERNRIKRLTRESFRLRQ
HELPPMDFVVAKRGVADLDNRALSEALEKLWRRHCRLARGS
Nucleotide sequence (plus strand): SEQ ID NO. 2
CGTCGTCGTCGTAAAGGCCGCGCTCGTCGTCTGACCGTTTCCAAGTAATAAAGCTAACCCTGCGTGGTTAAGCTCGCATT
TCCCAGGGAGTTACGCTTGTTAACTCCCAGTCATTTCACTTTCGTCTTCCAGCAGCCACAACGGGCTGGCACGCCGC
AAATCACCATCCTCGGCCCGCCCTGAATTCGCTGGGGCATCCCCCGACCTCCACCGGTCTCGCCAAGAAAAACGTGAAA
CGCGCACATGAACGCCAATCGGATTAAACGTCTGACGCGTGACCCTGCGATAACCGTCGATAACCGTCAACATGAACTCCCGCCAAT
GGATTCGTGGTGGTCGCGAAAAGAGAGGGGTTGCCGACCTCGATAACCGTCGATAACCGTCGATAACCGTTGAAAAATTAT
GGCGCCGGCCATTGTCGCCTGGCTCGCGGGTCCGGGGTCCTGATCGGCCGCTGAGTTATCAGCGCCGCCTGATTAGTCCGCTAC
TCGGGCCGATTGTC
Sequence origin: Washington University; Contig 632

FIG. 5C

Salmonella paratyphi A ATCC 9150 (110 aa)

Amino acid sequence: SEQ ID NO. 22

VTFVNSRSFHIRLPATSTGCTPQITILGRLNSLGHPRIGLTVAKKNVRRAHERNRIKRLTRESFRLRQHELPAMDFV
VVAKKGVADLDNRALSEALEKLWRRHCRLARGS

Nucleotide sequence (plus strand): SEQ ID NO. 3

CTGACCGTTCCAAGTAATAAAGCTAACCCCTGAGTGGTTAAGCTCGCATTCCCAGGAG*TTA*CGTTTGTTAACTC
CCGCTCATTCACATTCGTCTTCCAGCAACCTCAACGGCTGCACGCCGCAAATCACCATCCTCGGCCGCCTGAATT
CGCTGGGCATCCCCCGTATCGGTCTTACCGTCGCCAAGAAAAATGTTCGACGTGCGCATGAACGCAACCGATTAAA
CGTCTGACGCGTGAAAGCTTCCGTCTGCGCCAGCATGAACTTCCTGCAATGGATTCGTGGTGGTGGCGAAAAAAGG
GGTTGCCGACCTCGATAACCGTCTGCTCTCTCGGAAGCGTTGGAAAAATTATGGCGCGCCACTGTCGCCTGGCTCCGCG
GGTCCTGATA*G*CCCTTATTCGGGTCTATCAACGCCCTGATCAGTCCGCTGCTTGGGCCGCATTGTCGTTTC

Sequence origin: Washington University;

FIG. 5E

Corynebacterium diphtheriae (129 aa)
Amino acid sequence:    SEQ ID NO. 24
VTLTSSNRTTVLPSQHKLSNSEQFRATIRKGKRAGRSTVVLHFYAEATAGNLATAGGPRFGLVVSKAVGNAVTRHRV
SRQLRHVVIAMKDQFPASSHVVVRAIPPAATASYEELRADVQAALDKLNRKR
Nucleotide sequence (plus strand): SEQ ID NO. 5
CCGGTCGCGCAATCGTGGCTGCACGTCGTAACAAGGGTCGTAAGAGCCTGACCGCTTAAG*GTC*ACTCTTACAAGCTC
GAATAGAACGACGGTGCTACCTTCACAGCACAAGCTCAGCAATTCCGAACAGTTCCGCGCAACGATTCGGAAGGGCA
AGCGTGCTGGGAGGAGCACCGTCGTTCTTCATTTTTATGCTGAGGCGACCGCGGGCAACCTTGCAACCGCAGGCGGC
CCGCGATTCGGCCTCGTTGTGTCCAAGGCTGTTGGAAATGCTGTGACTCGTCACCGTGTTTCGCGGCAGTTAAGGCA
CGTAGTAATCGCTATGAAAGACCAGTTCCCAGCGTCATCCCATGTTGTTGTGAGGGCGATACCGCCAGCGGCGACAG
CAAGTTATGAGGAGTTGCGGGCAGATGTGCAGGCAGCACTCGACAAGCTCAACCGCAAGCGATAAGGCGGTTACTCG
CCCTCGTGGGCTGGTTAGTCGCGCATTGTTTGATGCGGTGCGGTTCTA
Sequence origin: Sanger centre; Contig 390

FIG. 5F

*Chlamydia trachomatis* MoPn (119 aa)
Amino acid sequence: SEQ ID NO. 25
VHRLTLPKSARLLKRKQFVYVQRCGQYCRTDQATLRIVPSRHSNIRKVGVTVSKKFGKAHQRNRFKRIVREAFRHVR
PNLPACQVVVSPKGGTLPNFGKLSADLLKHIPEALPLVTSSK
Nucleotide sequence (plus strand): SEQ ID NO. 6
GCTACAAAAAGTGGAAGAAATCTTTTAAATCGTCGTCGCCGTCACGGCAGACATTCCTTAATTGATCTCTAAGATCT
TTCATTT*GTG*CATCGGTTAACTCTACCTAAAAGTGCCCGCCTATTGAAACGTAAACAATTTGTTTACGTGCAGCGTT
GTGGGCAATATTGTCGTACTGATCAGGCAACTTTACGAATAGTTCCTTCTCGTCATTCGAACATCCGTAAAGTAGGG
GTTACTGTTTCTAAAAAATTTGGGAAAGCCCATCAGCGCAATCGCTTTAAAAGAATTGTGCGAGAGGCTTTTAGGCA
TGTGCGACCAAATCTTCCCGCATGTCAAGTGGTAGTGTCTCCTAAAGGGGGCACTCTACCAAATTTTGGTAAACTAT
CCGCGGATCTTCTTAAGCATATTCCAGAGGCTTTGCCTCTCGTTACTTCTTCTAAGTAGTTTTTTATTTTGGTCAAA
AAATAAAAAACCATTCCACGCTATAGAGGCATGGAATGGGAA
Sequence origin: TIGR & Manitoba University;

FIG. 5G

Vibrio cholerae serotype O1, Biotype El Tor, Strain N16961 (122 aa)

Amino acid sequence:    SEQ ID NO. 26

SRIILSTYAFNRELRLLTPEHYQKVFQQAHSAGSPHLTIIARANNLSHPRLGLAVPKKQIKTAVGRNRFKRICRESF
RLHQNQLANKDFVVIAKKSAQDLSNEELFNLLGKLWQRLSRPSRG

Nucleotide sequence (minus strand): *NO INITIATOR CODON BEFORE STOP*    SEQ ID NO. 7
GGCAGCGTGGGCCGATAAGTGGACTATAATAAACCACTGGTAAAGTTTTACAATACCAATGCTAACCACGAGAAGGC
GAGAGAGGCGTTGCCATAGTTTGCCAAGCAAGTTAAACAGTTCTTCATTGCTCAAATCTTGCGCGCTCTTTTTGGCG
ATGACAACAAAATCTTTGTTAGCCAGTTGATTTTGATGAACGCGAGTCCAAACGAGATGAGAAAGTTATTAGCGCAG
ACGGCCGACGCAGTTTGATCTGCTTTTTAGGAACCTGTGAGCTTGCTGAGACTTTTTGATAATGTTCGGAGTTAACAAA
CGATGATTGTGAGATGAGAGAACCAGACTACTCAAAATAATTCGAGATTATTTTGACAGGCGCTTACGGCCTTTGCACG
CGTAACTCCCGATTGAATGCGTACGTACTACTCAAAATAATTCGAGATTATTTTGACAGGCGCTTACGGCCTTTGCACG
ACGTGCATTCAGAACTTTACGACCGTTCGC Sequence origin: TIGR

FIG. 5H

Neisseria gonorrhoea FA 1090 (123 aa)

Amino acid sequence:    SEQ ID NO. 27

VILDYRFGRQYRLLKTDDFSSVFAFRNRSRDLLQVSRSNGNGLDHPRIGLVVGKKTAKRANERNYMKRVIRDWFRL
NKNRLPPQDFVVRVRKFDRATAKQARAELAQLMFGNPATGCGKQV

Nucleotide sequence (minus strand):    SEQ ID NO. 8
ATGTTCCTTGTATGGAACCCGTTGCCGTTCTGAACCTTGCCTGCAGGTACCGTTCTGATCATACCTGTTCCCGC
ATCCGGTTGCGGGGTTGCCGAACATGAGTTGTGCCAGCAGTTGTGAGGCGGCAGCAGGCCGGTTCCGCGTTTGCGGGTAGCCCTGTCGAATTTC
CGGCGGACGCGCACGACGAAATCCTGAGGCGGCAGCCGGTTTTGTTCAATCTGAACCAGTCGCGATGACGCGTTT
CATATAGTTCCGCTCGTTGCGCGTTTGGCGGTTTTTTGCCGACCAGACCGATGCGGGGATGGTCCAGCCGT
TGCCGTTTGAGCGCGAAACTTGCAGCAGTCGCGGCTGCGGCCGGTTCTGAATGCAAAAACGATGCAAAAATCATCC
GTTTTTAACAAGCGGTACTGCCTTCCGAAGCGGTAGTCCAAAATTACACTGCCAGGCGTTTGCGGCGTTTGGCACGG
CGTGCGGCCAATACTGCGCGTCCGCGCGT Sequence origin: University of Oklahoma ACGT; Contig 60

FIG. 5I

***Neisseria meningitidis* serogroup A Strain Z2491** (123 aa)

Amino acid sequence: SEQ ID NO. 28

VILDYRFGRQYRLLKTDDFSSVFAFRNRRSRDLLQVSRSNGNGLDHPRIGLVVGKKTAKRANERNYMKRVIRDWFRL
NKNRLPPQDFVVRVRRKFDRATAKQARAELAQLMFGNPATGCRKQA

Nucleotide sequence (minus strand): SEQ ID NO. 9

TGTTCCTTAGTATGGGAAACCCGTTGCCGTCTGAACCTTGCCTGCAGAGTACCGTTCTGATCATGCCTGTTTCCTGC
ATCCGGTTGCGGGGTTGCCGAACATGAGTTGTGCCAGTTCCGCCCTTGCCTGTTTTGCGGTAGCCCTGTCGAATTTA
CGGCGGACGCGCACGACGAAATCCTGCGGCGGCAGCCGGTTTTTGTTCAATCTGAACCAGTCGCGGATGACGCGCTT
CATATAATTTCGTTCGTTGGCGCGTTTGGCGGTTTTTTGCCGACCACCAGACCGATGCGGGGATGATCCAGCCCGT
TGCCGTTTGAACGCGAAACTTGCAGCAGGTCGCGGCTGCGGCGGTTTCTGAATGCAAAAACGGATGAAAAATCATCC
GTTTTCAACAAGCGGTACTGCCTTCCGAAGCGGTAGTCCAAAATTACACCGCCAGGCGTTTGCGGCCTTTGGCGCGC
CGTGCGGCCAATACTGCGCGTCCGCCGCGC

Sequence origin: Sanger centre & Oxford University

FIG. 5J

***Streptococcus pyogenes* M1** (113 aa)

Amino acid sequence: SEQ ID NO. 29

VKREKDFQAIFKDGKSTANRKFVIYHLNRGQDHFRVGISVGKKIGNAVTRNAVKRKIRHVIMALGHQLKSEDFVVIA
RKGVESLEYQELQQNLHHVLKLAQLLEKGFESEEKH

Nucleotide sequence (minus strand): SEQ ID NO. 10

GTTACCTCACCACGACCACAGGCCACTAATAATAGAACTAAGGGGACTATTCTTGCAATTTTAATGTTTTTCTTCAC
TCTCAAAACCTTTCTCAAGCAATTGTGCTAACTTTAAAACATGATGTAAATTTTGTTGAAGCTCTTGATACTCCAAA
GATTCGACACCCTTACGGGCAATCACCACGAAATCCTCTGACTTCAGCTGATGCCCTAATGCCATGATAACATGACG
TATCTTTCGTTTGACTGCATTTCTGGTGACTGCATTTCCTATTTTTTACCGACAGAAATACCCACACGGAAGTGGT
CTTGGCCTCTATTTAAATGATAAATGACAAATTTTCGATTTGCTGTACTTTTTCCATCCTTAAATATGGCTTGGAAA
TCTTTCTCACGCTTGACACGATAGGTCTTCTTCAAAATTTAACTCCAATATCTAAATTATTACCATTATACCACATC

Sequence origin: University of Oklahoma ACGT; Contig 7

FIG. 5K

Bordetella pertussis Tohama I (123 aa)

Amino acid sequence:  SEQ ID NO. 30

MPRATLPAEARLHRPSEFAAALKGRRLARGAFFIVSASPCAPADDQPARARLGLVIAKRFAARAVTRNTLKRVIREA
FRARRLALPAQDYVVRLHSKLTPASLTALKRSARAEVDAHFTRIAR

Nucleotide sequence (minus strand):  SEQ ID NO. 11

CCACCCAGGGCTGAGGAAGTACCGGTAAAACCGGATCGGGGCGATAAGCAGTCTCCTGATCATCGGCTATCCGTG
TGAAGTGAGCATCTACTTCGGCGCCGGCAGGCGTTCAGGGCCGTGAGGCTTGCCGGTGTCAGCTTGCTGTGCAGC
CGCACCACGTAATCCTGGGCCGGCAGGGCAAGCCGGCGAGCCGGAACGCTTCGCGGATGACCCGCTTCAAGTATT
GCGCGTCACGGCCGGGGCGGCAAAACGCTTGGCGATCACCAGGCGCGCCCAGGCGCGCCTTTGAGGCGCGGCAG
GGGCACAGGGCGAGGCGCTGACAATAAAGAAGAAGCCCCTCGGGCCCAGTGCCGCCGGGCTGACGTGGTCATCGG
GAGGGGCGATGCAATCGCGCCTCCGCAGGAGCGTGGCGCCGGCATGGGTGACGTGACGGAGACTGGCGACGGGGC
CGGCGGCGATGCTCCTGTTACAGGCAATCC

Sequence origin: Sanger centre & MDS; Contig 267

FIG. 5L

Porphyromonas gingivalis W83 (137 aa)

Amino acid sequence:  SEQ ID NO. 31

MTSPPTFGLSKSERLYLRDEINTVFGEGKAFVVYPLRVVYRLGSEHRVAYSSMLVSVAKKRFRRAVKRNRVKRLVRE
AYRLNKHLLNDVLQERQIYATIAFMVVSDELPDFRTVERAMQKSLIRIAGNVPSSALKNE

Nucleotide sequence (minus strand):  SEQ ID NO. 12

AGAAGAAAATGGGAGCAGTAGAGTTGCACGAGAAAAGCCTTGATCAGTCGCATCGTATTTACTCGTTTTCAAAG
CCGATGAAGGTACATTTCCGGCAATTCTGATCAGATCTCTTTTGCATCGCTCTCCACTGTACGAAAGTCAGGAAGT
TCATCCGATACTACCATAAATGCATAGTAGCATAGATCGTCTCTTGGAGGACATCGTTCAGGAGGTGTTTGTT
GAGCCGATAAGCCTCCCTGACCAAAACGCTTGACCCTATTGCGCTTCACGGCTCGCCTAAACCTTTTCTTTGCTACGC
TTACCAGCATGGAGGAATATGCAACTCGATGCTCCCAGACGGTAGACTACGCGTAGAGGATAAACGACAAAC
GCCTTGCCTTCGCAAAGACCGTATTGATTTCATCGCGAAGATAGAGGCGTTCGCTTTTGGATAGGCCGAATGTAGG
CGGAGAGGTCATTTCCCGTTGAGGTAATCCTCTAATCCATAGCCATAGAAGGATATTGCTCGGTCGGCGCA

Sequence origin: TIGR & Forsyth Dental Center

FIG. 5M

Streptococcus pneumoniae Type 4 (124 aa)

Amino acid sequence:    SEQ ID NO. 32

VLKKNFRVKREKDFKAIFKEGTSFANRKFVVYQLENQKNRFRVGLSVSKKLGNAVTRNQIKRRIRHIIQNAKGSLVE
DVDFVVIARKGVETLGYAEMEKNLLHVLKLSKIYREGNGSEKETKVD

Nucleotide sequence (minus strand):        SEQ ID NO. 13

TCGCTAGTAGTACCCCATTAGTCGCACAGGCTGTCATGATTAACAGAGACAGTCCTAGCAAACTAGTCAACTTAGTTT
CTTTTCACTCCCATTCCTTCCCGGTAAATCTTTGATAATTTAATACATGGAGTAGATTTTCTCCATCTCTGCG
TATCCCAAGGTTTGACTCCTTTCGAGCAATGACAACAAAGTCGACATCTTCTACCAGACTCCCTTTGCATTCTG
GATAATATGCCGAATCCGTCGCTTAATTTGATTTCTAGTAGACCAGTTTTTGCTAACTGATAGACCTA
CTCGAAAACGGTTTTCTGGTTTTCTAATTGGTAGACACGAAAGTTTTCTCCAAAACTTGTCCCCTCCTTGAAA
ATCGCCTAAAATCTTTCTCTTTTTACACGAAAGTTTTCTCAAAACTCAACTCCATCTATTAAATTACTACTA
TTATACCATATTTTTCAAAAAGCCAATCATAG

Sequence origin: TIGR;

FIG. 5N

Clostridium difficile 630 (epidemic type X) (114 aa)

Amino acid sequence:    SEQ ID NO. 33

MDFNRTKGLKKDSDFRKVYKHGKSFANKYLVIYILKNKSDYSRVGISVSKKVGKAITRNRVRRLIKEAYRLNIDEKI
KPGYDIVFIARVSSKDATFKDIDKSIKNLVKRTDISI

Nucleotide sequence (minus strand):        SEQ ID NO. 14

TCCTTTAATATATAAATTATTTTATTCAAAGTCATTAACCTCCATATTTATAGCATACAATTAAATAGAAATATCCG
TTCTTTTAACTAAATTTTTATAGACTTGTCTATGTCTTTAAAAGTAGCATCCTTACTAGATACCCTTGCTATAAAT
ACTATATCATATCCAGGCTTAATTTTTCATCATAATTAATCTGTAGGCTTCTCTTTATTAATCTCTTACTCTATT
CCTAGTAATAGCTTTCCTACTTTTTTTGAAACAGAAATACCTACTACTATAATCTGATTATTTTAAGTATAT
ATATTACTAAATATTTGTTGCAAAAGATTTGCCGTGTTTATATACTTTCTAAAATCAGAGTCTTTTTCAACCCT
TTAGTCCTATTAAAGTCCATAGTTAACCTCCATAAACACAGCTAATCGTAATTATTTACACAAAAGGCCACCT
TTG

Sequence origin: Sanger centre; Contig 975

FIG. 5O

Camphylobacter jejuni NCTC (108 aa)
Amino acid sequence:                SEQ ID NO. 34
VKNFDKFSTNEEFSSVYKVGKKWHCEGVIIFYLNSYEKKIAVVASKKVGKAVVRNRSKRILRALFAKFERYLQDGKY
IFVAKNEITELSFSRLEKNLKWGLKKLECFK
Nucleotide sequence (minus strand):            SEQ ID NO. 15
AAGCAGCGGGTTTAAAGGGCTTAAGAATTCTGATAAAACGGAGTATTTTAGGCATATCATTTGAAACATTCTA
GTTTTTCAATCCCCATTTTAGATTTTTTTCTAACCTAGAGAAAAGAAAGTTCAGTGATTCATTTTAGCTACAAAA
ATATATTGCCATCTGAAGATATCTTCAAACTTAGCAAACAAAGCTCTTAAAATTCGTTTTGAACGATTCTAAC
CACTGCTTTCCAACTTTTTACTAGCAACAACTGCTATTTTTTTCATAACTATTCAGATAAAAATGATCACAC
CTTCGCAATGCCAATTTTTTGCCTACTTTATATACAGATGAAAATTCCTCGTTTGTGCTAAATTATCAAAATTTTTC
ACACAGCAAGTCTTTTTCTACCTTTAGCGCGTCTTGCATTGATCACTTTGCGACCATTTTA
Sequence origin: Sanger centre & MDS

FIG. 5P

Bacillus anthracis Ames (119 aa)
Amino acid sequence:                SEQ ID NO. 35
MKKKHRIKKNDEFQTVFQKGKSNANRQFVVYQLDKEEQPNFRIGLSVSKKIGNAVVRNRIKRMIRQSITELKDEIDS
GKDFVIIARKPCAEMTYEELKKSLIHVFKRSGMKRIKSSVRK Nucleotide sequence (minus strand): SEQ ID NO. 16

TAAACCTAATTTCTTTTTCAAAGCCTACTCCTCCTTGTATCGGTATGTATATAGTGTAATTCATTTCCTTACGCTAC
TTTTTATTCTTTTCATACCAGAGCGTTTAAAGACATGAATTAAGCTTTTCTTTAATTCTTCATATGTCATCTCTGCA
CAAGGCTTCCTTGCTATTATAACAAAATCTTTTCCAGAATCTATCTCATCTTTTAATTCTGTGATCGACTGGCGAAT
CATACGTTTAATTCGGTTACGCACTACTGCATTTCCTATCTTCTTGCTGACAGAAAGGCCAATACGAAAGTTTGGCT
GCTCTTCTTTATCTAGTTGATAGACAACAAATTGACGATTCGCATTCGATTTCCTTTTTGAAAAACCGTCTGGAAT
TCATCATTCTTTTTTATACGATGTTTTTTCTTCATATCAATTGACACTCCTGTAGTTCATCAGCGGAAATTCACTAT
TATTAGAAAAAAAGACCA

Sequence origin: TIGR;

FIG. 5Q

Mycobacterium avium 104 (119 aa)

Amino acid sequence:  SEQ ID NO.36

MLPARNRMTRSTEFDATVKHGTRMAQPDIVVHLRRDSEPDDESAGPRVGLVVGKAVGTAVQRHRVARRLRHVARALL
GELEPSDRLVIRALPGSRTASSARLAQELQRCLRRMPAGTGP

Nucleotide sequence (minus strand):  SEQ ID NO.17

GTCCGCGGGCGACGGTTCGGCCGCGAATGCCGCCCGACCGCGCCGCCCGGTCCGGTTCCCG
CCGGCATGCCGCCGCAGGCACCCGTGCAGTTCCTGCGCCAGCGCCGACGCCGGCTTCCGGGCAGCGCG
CGAATCACCAGCCGGTCGGATGGTTCGAGTTCGCCGACGTCGACGGCCACGTGACGCAGCCGGGGCCACGCG
GTGTCGTTGCACCGCCGTCCCGACGGCCTTCCCGACGACCAGCCGCTGGGCCCGGATTCGTCGTCGGGTT
CGGAGTCGCGCCGGAGGTGGACGACGATGTCGGGCTTGCCGCCATGCGGCTTCACCGTCGCGTCAAACTCG
GTTGACCGGCGTCATGCGGTTGCGTGCGGAAGCACCGCGAAAGACCTGACGTGCGATCAGCAGGCAGAGAGCGGCGGCCG
ACCCTTGCGGCGCCGACC

Sequence origin: TIGR;

FIG. 5R

Staphylococcus aureus NCTC 8325 (117 aa)

Amino acid sequence:  SEQ ID NO. 37

MLLEKAYRIKKNADFQRIYKKGHSVANRQFVVYTCNNKEIDHFRLGISVSKKLGNAVLRNKIKRAIRENFKVHKSHI
LAKDIIVIARQPAKDMTLQIQNSLEHVLKIAKVFNKKIK

Nucleotide sequence (plus strand):  SEQ ID NO. 18

GTTATAAGCTCAATAGAAGTTTAAATATAGCTTCAAATAAAACGATAATAAGCGAGTGATGTTATTGAAAAAGC
TTACCGAATTAAAAAAATGCAGATTTTCAGAGAATATATAAAAAAGGTCATTCTGTAGCCAACAGACAATTTGTTG
TATACACTTGTAATAATAAAGAACCATTTCGCTTAGGTATTAGTGTTTCTAAAAAACTAGGTAATGCAGTG
TTAAGAAACAAGATTAAAAGAGCAATACGTGAAAATTTCAAAGTACATAAGTCGCATATATATTGGCCAAAGATATTAT
TGTAATAGCAAGACAGCCAGCTAAAGATATGACGACTTTACAAATACAGAATAGTCTTGAGCACGTACTTAAAATTG
CCAAAGTTTTTAAATAAAAAGATTAAGTAGGATAGGGTAGGGAAGGAAAAACATTAACCACTCAACACATCCCGAAG
TCTTACCTCAGA

Sequence origin: University of Oklahoma ACGT; Contig 561

FIG. 5S

*Staphylococcus aureus* COL (117 aa)
Amino acid sequence: SEQ ID NO. 38
MLLEKAYRIKKNADFQRIYKKGHSVANRQFVVYTCNNKEIDHFRLGISVSKKLGNAVLRNKIKRAIRENFKVHKSHI
LAKDIIVIARQPAKDMTTLQIQNSLEHVLKIAKVFNKKIK Nucleotide sequence (plus strand): SEQ ID NO. 19
GTTATAAGCTCAATAGAAGTTTAAATATAGCTTCAAATAAAACGATAAATAAGCGAGTGATGTTATTGGAAAAAGC
TTACCGAATTAAAAAGAATGCAGATTTTCAGAGAATATATAAAAAAGGTCATTCTGTAGCCAACAGACAATTTGTTG
TATACACTTGTAATAATAAAGAAATAGACCCATTTCGCTTAGGTATTAGTGTTTCTAAAAAACTAGGTAATGCAGTG
TAAGAAACAAGATTAAAAGAGCAATCGTGAAAATTCAAGTACATAAGTCGCATATATTGGCCAAAGATATTAT
TGTAATAGCAAGACAAGCCAGCTAAAGATATGACGACTTTACAAATACAGAATAGTCTTGAGCACGTACTTAAAATTG
CCAAAGTTTTTAATAAAAAGATTAAGTAAGGATAGGGTAGGGGAAGGAAAAACATTAACCACTCAACACATCCCGAAG
TCTTACCTCAGA Sequence origin: TIGR;

FIG. 6A

***Pasteurella multocida* PM70** (119 aa)

Amino acid sequence: SEQ ID NO. 50

VIKLNFSRELRLLTPLHFKYVFEQPFRASTPELTILARPNNLAHPRLGLTVAKKHLKKAHDRNRIKRLCRESFRLAQ
YKLPNCDFVIVAKQGIGKLDNRTLTQTLDKLWQRHIRLAQKS

Nucleotide sequence (plus strand): SEQ ID NO. 39

GTGATTAAGCTGAATTTTTCGAGGGAGTTACGTTTGTTAACTCCCCTTCATTTTAAATACGTCTTCGAACAGCCGTT
CCGTGCTAGTACACCTGAACTTACCATTCTTGCTCGTCCCAATAATCTCGCTCATCCTCGCTTAGGGTTAACTGTCG
CGAAAAAGCATTTAAAAAAAGCACATGATCGCAATCGCATCAAACGCTTATGCCGAGAAAGTTTCCGCCTAGCACAG
TATAAACTCCCCAATTGCGATTTTGTTATTGTGGCGAAACAGGGAATTGGTAAATTAGACAACAGGACACTCACACA
AACATTGGATAAATTATGGCAAAGACACATTCGCTTAGCTCAAAAATCTTGA

Sequence origin: University of Minnesota Computational Biology Center

FIG. 6B

***Haemophilus ducreyi* strain 35000HP** (123 aa)

Amino acid sequence: SEQ ID NO. 51

VNKLTFSRELRLLAPIQFKAVFEQPYRASTAELTILARQNCVNTPRLGLTVAKKHLKRAHDRNRIKRIVRESFRLKQ
HQLPNFDFVFVAKHGIGKLDNATLFATIDKLWTRHIRLSQQAQSKN

Nucleotide sequence (minus strand): SEQ ID NO. 40

TTAATTTTTGCTTTGTGCTTGTTGACTGAGGCGAATATGACGAGTCCATAATTTATCTATGGTTGCGAAAAGCGTAG
CATTATCTAGTTTACCAATCCCATGCTTGGCAACAAAGACAAAGTCAAAATTAGGTAATTGATGTTGTTTTAAACGG
AAGCTTTCCCGCACAATACGTTTGATCCGATTGCGATCGTGAGCACGTTTTAAATGCTTTTTAGCAACGGTTAACCC
AAGACGAGGCGTATTAACGCAATTTTGACGAGCAAGAATAGTAAGTTCAGCTGTGCTAGCACGATATGGTTGTTCAA
ACACGGCTTTGAATTGAATGGGAGCTAACAAACGTAGCTCCCGAGAAAACGTTAGCTTATTCAC

Sequence origin: HTSC (Washington University)

FIG. 6C

*Chlamydia muridarum* (119 aa)
Amino acid sequence: SEQ ID NO. 52
MHRLTLPKSARLLKRKQFVYVQRCGQYCRTDQATLRIVPSRHSNIRKVGVTVSKKFGKAHQRNRFKRIVREAFRHVR
PNLPACQVVVSPKGGTLPNFGKLSADLLKHIPEALPLVTSSK
Nucleotide sequence (plus strand): SEQ ID NO. 41
*GTG*CATCGGTTAACTCTACCTAAAAGTGCCCGCCTATTGAAACGTAAACAATTTGTTTACGTGCAGCGTTGTGGGCA
ATATTGTCGTACTGATCAGGCAACTTTACGAATAGTTCCTTCTCGTCATTCGAACATCCGTAAAGTAGGGGTTACTG
TTTCTAAAAAATTTGGGAAAGCCCATCAGCGCAATCGCTTTAAAAGAATTGTGCGAGAGGCTTTTAGGCATGTGCGA
CCAAATCTTCCCGCATGTCAAGTGGTAGTGTCTCCTAAAGGGGGCACTCTACCAAATTTTGGTAAACTATCCGCGGA
TCTTCTTAAGCATATTCCAGAGGCTTTGCCTCTCGTTACTTCTTCTAAGTAG
Sequence origin: TIGR

FIG. 6D

*Chlamydophila psittaci* (139 aa)
Amino acid sequence: SEQ ID NO. 53
VHRSTLPKYARVLKRKQFLYISRAGSHCQGSQVIFHVAPSRYSGCCKLGITVSKKFGKAHKRNYFKRIVREAFRKKR
HSLPACQIVVMPKNKQQPKFEDLLQDFAQQIPEALSSKLAKNKPTTGVEYSPKNEKCESVLP
Nucleotide sequence (plus strand): SEQ ID NO. 42
*GTG*CATCGATCAACCTTACCCAAATATGCTCGTGTGTtAAAGAGAAAGCAGTTTCTCTACATCTCGCGAGCGGGATC
TCACTGTCAAGGCAGTCAGGTTATTTTTCATGTTGCTCCATCTAGATATTCTGGATGTTGCAAGCTTGGGATAACTG
TCTCAAAAAAATTTGGGAAAGCGCATAAAAGAAATTATTTAAACGTATTGTGCGCGAGGCTTTTCGTAAAAAGCGT
CACTCTCTTCCTGCTTGTCAAATTGTTGTTATGCCTAAAAACAAGCAGCAACCTAAATTTGAAGATCTGCTTCAAGA
CTTTGCTCAGCAAATTCCAGAAGCACTCAGTAGCAAATTAGCAAAAAATAAGCCTACGACTGGTGTCGAATATAGTC
CAAAGAATGAGAAATGTGAGTCTGTACTTCCTTAG
Sequence origin: TIGR

FIG. 6E

*Treponema denticola* (118 aa)

Amino acid sequence:   SEQ ID NO. 54

VSNFTFSGEERLRDRSCIKAVFQKGLKLSLNGVSLLILPNGLEYNRFLCTFRRGFGSAVMRNRSRRISKEAYRHIKH
RLKTGNDILLLVFSEKDSYSLRLEQLTALFLKAKMYNDEAL

Nucleotide sequence (minus strand):   SEQ ID NO. 43

TCATAAAGCCTCATCATTATACATTTCGCTTTTAAAAGAGGCGGTAAGTTGTTCTAAACGAAGAGAATAAGAAT
CCTTTCTGAAAAACCAGCAGGATAATGTCGTTTCCCGTTTTAACCTATGTTTATGTCTATAGGCCTCTTTT
GATATTCTCCGAGACCTGTTCCGCATCACTGCGGAACCGAAACCTCGTCGAAAAGTACATAAGAATCGATTGTACTC
CAATCCATTAGGCAGGATTAACAAACTAACTCCGTTAAGCTAAGTTTAAGACCCTTTTGAAATACGGCCTTAATAC
ATGACCGATCCCTTAACCGTTCTTCACCGGAAAATGTAAAATTACTCAC

Sequence origin: TIGR

FIG. 6F

*Enterococcus faecalis* (118 aa)

Amino acid sequence:   SEQ ID NO. 55

MKKSYRVKKEKEFQQVFNKKQSCANRRFVVYVLEKPQQAHFRVGISVGKKIGNAVTRNAVKRKIRASLFQLKDRISP
EIDFIVIARPGLEKLSSEEVKANLTHVLNLAKILDVREGIE

Nucleotide sequence (minus strand):   SEQ ID NO. 44

CTACTCAATTCCCTCTCTTACATCTAATATTTAGCTAAACATGTGTTAAATTAGCTTTCACTTCTTCAG
ACGATAACTTTTCCAATCCTGGACGTGCAATCACGATAAAATCAATTCTGGAGAGATACGGTCTTTAATTGAAAT
AAACTCGCGCGGATTTCCGCTTCACAGCATTCTTGTGACCGCGTTTCCAATTTCTTCCAACAGAAATCCCCAC
TCGAAATGGGCTTGTGTGGTTTCTAAAACGTACACCACGAAACGACGATTTGCACAAGATTGTTTTTATTAA
ACACCTGTTGAAATTCTTTTTCTTCTTGACACGGTAGGACTTTTCAT

Sequence origin: TIGR

FIG. 6G

*Legionella pneumophila* (109 aa)

Amino acid sequence: SEQ ID NO. 56

QPHRLLKKNHFDFVFQSAKKIPTDDFIFLFRENKLGYARLGLALSKKMIAKAHDRNRIKRLLRESFRHTNLPAVDII
ILARPGLAKKTNLGINTKLNKTWEKLASCYGK

Nucleotide sequence (minus strand): *NO INITIATOR CODON BEFORE STOP* SEQ ID NO. 45

CTATTTGCCGTAGCATGAGGCTAATTTTTCCCATGTTTTATTTAATTTAGTATTTATACCTAAATTGGTTTTCTTTG
CTAGACCTGGTCTTGCCAAAATGATTATATCTACAGCAGGCAAGTTAGTATGACGAAAACTTTCTCTAAGTAGCCGT
TTAATGCGATTTCTGTCATGAGCCTTAGCTATCATTTTTTTGACAATGCTAAACCAAGGCGTGCATAGCCTAACTT
ATTTTCTCTGAAAAGGAAAATAAAGTCATCTGTAGGTATTTTTTTCGCGCTTTGAAACACGAAGTCAAAATGATTTT
TTTTTAATAAGCGGTGCGGCTG(STOP)

Sequence origin: Columbia Genome Center

FIG. 6H

*Staphylococcus epidermis* (115 aa)

Amino acid sequence: SEQ ID NO. 57

MEKAYRIKRNSDFQAIYKNGKSVANRQFVVYTYKNRDLKHFRLGISVSKKLGNAVTRNRIKRAIRENFKVHKQNIIA
KDIIVIARQPAKDMNTLEIQSSLEHVLKIAKVFNKKIK

Nucleotide sequence: SEQ ID NO. 46

CTACTTAATCTTTTTATTAAACACTTTTGCAATTTTAAGCACATGCTCTAAACTGCTTTGAATCTCCAGTGTATTCA
TATCTTTTGCTGGTTGCCTCGCAATAACTATAATATCTTTAGCGATAATATTTTGCTTATGCACTTTAAAATTCTCT
CTTATCGCTCTTTTAATTCTATTTCTTGTAACAGCGTTGCCCAGTTTTTTTGAGACACTTATTCCTAAGCGAAAATG
TTTTAAATCTCTATTTTTATAGGTATAGACAACAAATTGTCTATTTGCAACAGACTTCCCATTCTTGTATATCGCTT
GAAAGTCTGAATTTCTCTTAATACGATATGCTTTTTC*CAT*

Sequence origin: TIGR

FIG. 6I

*Mycobacterium smegmatis* (130 aa)

Amino acid sequence: SEQ ID NO. 58

VLPARNRMRRSAEFSVTVSRGVRAAQPDVVVHALRLESNAGNAGDDGDDGDANGPRIGLIVSKAVGNAVERHRVSRR
LRHVAKTFVSGLDPADLIVIRARPSSRDATSSRLERQLGQALERVSSKRRASP

Nucleotide sequence: SEQ ID NO. 47

TCATGGGGACGCCCTGCGCTTCGAGCTCACCCGCTCGAGCGCTTGACCCAACTGTCGTTCCAAACGGGACGACGTGG
CGTCACGACTGCTCGGCCTGGCCCGGATCACGATGAGATCGGCAGGGTCAAGACCGGATACGAACGTTTTGGCGACG
TGCCGCAGACGGCGGGACACGCGGTGACGCTCCACCGCGTTGCCGACGGCTTTGGACACGATCAGACCGATCCGCGG
CCCGTTCGCGTCGCCGTCATCGCCGTCATCGCCGGCATTGCCTGCGTTGCTTTCAAGGCGCAACGCGTGTACGACGA
CATCGGGTTGCGCGGCACGCACGCCGCGACTGACGGTGACACTGAACTCCGCGGACCGCCTCATCCGGTTTCGAGCC
GGAAG*CAC*

Sequence origin: TIGR

FIG. 6J

*Burkholderia pseudomallei* (97 aa)

Amino acid sequence: SEQ ID NO. 59

VRGSIPLQASAAFPKAARLLKTDEFSSVFRLRPWRRTAHFVIYGKPTGRDARLGLVIGKKYAARAVTRNLVKRLARE
AFRTRRAEFAGWDILLRLHA

Nucleotide sequence: SEQ ID NO. 48

CGCATGCAGGCGCAGCAGAATGTCCCAGCCGGCGAACTCGGCGCGACGCGTACGAAAC
GCCTCGCGGGCGAGCCGCTTGACCAGATTGCGCGTCACCGCACGCGCGGCGTACTTCTTG
CCGATGACGAGCCCAAGACGCGCATCGCGCCCCGTCGGCTTGCCGTAGATCACGAAGTGC
GCGGTGCGCCGCCAGGGACGCAAACGAAAAACGGATGAGAATTCATCCGTTTTCAGAAGT
CGCGCAGCTTTGGGGAAGGCGGCGGACGCTTGCAACGGAATCGAACCCCG*GAC*

Sequence origin: Sanger Center

FIG. 6K

Ureaplasma urealyticum (113 aa)
Amino acid sequence:      SEQ ID NO. 60
MANFISLKKNEDILDTIKKQQKIHSNQIVVYFRKTNLKNVRLAISISKKKFKLATQRNRIRRLIKAWFIAADIPIKS
YDIVVLVKPSFIDGSFVLNCNNLKIILQRIINKEKR Nucleotide sequence (minus strand):      SEQ ID NO. 49
TTATCTTTTTCTTTGTTAATAATTCGTTGAAGAATTATTTAAGATTATTACAATTAAAACAAAGAACCATCAA
TAAACGATGGTTCACTAAGACTACAATATCATAACTTTAAGTGGAATATCAGCAGCAATAAACCATGCTTAATC
AGGCGTCGAATTCGATTGCGTTGTGTTGCTAATTAAACTTTTTTTAGAAATGCTTATAGCTAAGCGAACATTTT
TAGATTGGTTTACGAAATAAACTACGATTTGATTAGAATGAATTTTTGTTGTTTCTTAATTGTATCAAGTATAT
CTTCATTTTTTTAGACTAATAAAATTAGCCAT Sequence origin: University of Alabama at Birmingham

SEQUENCE LISTING

<160> NUMBER OF SEQ ID NOS: 114

<210> SEQ ID NO 1
<211> LENGTH: 417
<212> TYPE: DNA
<213> ORGANISM: Streptococcus mutans UAB159

<400> SEQUENCE: 1

```
agattttttgg cttttctctca ttttatgata taatagtgat aatttaaata ttggagtcat    60
gttttgaaaa aagcctatcg cgttaaaagt gataaagatt ttcaggcaat ttttactgaa   120
ggacgaagtg ttgccaatcg gaaatttgtt gtctatagtt tagaaaaaga tcaaagtcac   180
tatcgtgttg gactttcagt tggaaaaaga ttaggaaatg ctgtcgttag aaatgcgatt   240
aaacgaaaat tgcgccatgt ccttatggaa cttggtcctt atttaggcac tcaagatttt   300
gttgttattg ctagaaaagg tgttgaggaa cttgattata gcacgatgaa aaaaaatctg   360
gttcatgttt taaaactggc taaactgtat caggaaggat ctattcgtga aaaagaa      417
```

<210> SEQ ID NO 2
<211> LENGTH: 477
<212> TYPE: DNA
<213> ORGANISM: Klebsiella pneumoniae M6H 78578

<400> SEQUENCE: 2

```
cgtcgtcgtg ctaaaggccg cgctcgtctg accgtttcca agtaataaag ctaaccctgc    60
gtggttaagc tcgcatttcc cagggagtta cgcttgttaa ctcccagtca tttcactttc   120
gtcttccagc agccacaacg ggctggcacg ccgcaaatca ccatcctcgg ccgcctgaat   180
tcgctggggc atccccgcat cggtctcacc gtcgccaaga aaaacgtgaa acgcgcacat   240
gaacgcaatc ggattaaacg tctgacgcgt gaaagttttc gtttgcgtca acatgaactc   300
ccgccaatgg atttcgtggt ggtggcgaaa agaggggttg ccgacctcga taaccgtgct   360
ctctcggaag cgttggaaaa attatggcgc cgccattgtc gcctggctcg cgggtcctga   420
tcggcctgat tcgagtttat cagcgcctga ttagtccgct actcgggccg cattgtc     477
```

<210> SEQ ID NO 3
<211> LENGTH: 455
<212> TYPE: DNA
<213> ORGANISM: Salmonella paratyphi A ATCC9150

<400> SEQUENCE: 3

```
ctgaccgttt ccaagtaata aagctaaccc ctgagtggtt aagctcgcat ttcccaggga    60
gttacgtttg ttaactcccg ctcatttcac attcgtcttc cagcaacctc aacgggctgc   120
acgccgcaaa tcaccatcct cggccgcctg aattcgctgg ggcatccccg tatcggtctt   180
accgtcgcca agaaaaatgt tcgacgtgcg catgaacgca accggattaa acgtctgacg   240
cgtgaaagct tccgtctgcg ccagcatgaa cttcctgcaa tggatttcgt ggtggtggcg   300
aaaaaagggg ttgccgacct cgataaccgt gctctctcgg aagcgttgga aaaattatgg   360
cgccgccact gtcgcctggc tcgcgggtcc tgatagccct tattcgggtc tatcaacgcc   420
tgatcagtcc gctgcttggg ccgcattgtc gtttc                              455
```

<210> SEQ ID NO 4
<211> LENGTH: 528
<212> TYPE: DNA
<213> ORGANISM: Pseudomonas aeruginosa PAO1

<400> SEQUENCE: 4

```
tctgtcgcgt cgtcgcgcca aaggccgtaa gcgtctgacc gtctgattta ccggtacgg      60
gtggtgagtc gggacttcga ccgggacaag cgtctactga cagcccggca attcagcgca    120
gtcttcgact ctccgaccgg caaggtcccc ggcaagcacg tcctgctgct ggcgcgcgag    180
aacggtctcg atcaccccg cctgggcctg gtgatcggca agaagaacgt caagctcgcc    240
gtccagcgca atcgcctcaa acgcctgatc cgcgaatcgt tccgccataa ccaggaaacc    300
ctggctggct gggatatcgt ggtgatcgcg cgcaaaggcc tgggcgaact ggaaaatccg    360
gagctgcacc agcagttcgg caagctctgg aaacgcctgt tgcgcaatcg acctcgcacg    420
gaaagccctg ctgacgcccc tggcgtggcc gacggtactc atgcataggt cgatgcccgc    480
gcatcccgat ccctgtagtg tcatccccc ttcgatgacc cggcaccg                 528
```

<210> SEQ ID NO 5
<211> LENGTH: 510
<212> TYPE: DNA
<213> ORGANISM: Corynebacterium diphtheriae

<400> SEQUENCE: 5

```
ccggtcgcgc aatcgtggct gcacgtcgta acaagggtcg taagagcctg accgcttaag     60
gtcactctta caagctcgaa tagaacgacg gtgctaccct cacagcacaa gctcagcaat    120
tccgaacagt tccgcgcaac gattcggaag ggcaagcgtg ctgggaggag caccgtcgtt    180
cttcatttt atgctgaggc gaccgcgggc aaccttgcaa ccgcaggcgg cccgcgattc    240
ggcctcgttg tgtccaaggc tgttggaaat gctgtgactc gtcaccgtgt tcgcggcag    300
ttaaggcacg tagtaatcgc tatgaaagac cagttcccag cgtcatccca tgttgttgtg    360
agggcgatac cgccagcggc gacagcaagt tatgaggagt tgcgggcaga tgtgcaggca    420
gcactcgaca agctcaaccg caagcgataa ggcggttact cgccctcgtg ggctggttag    480
tcgcgcattg tttgatgcgg tgcggttcta                                    510
```

<210> SEQ ID NO 6
<211> LENGTH: 504
<212> TYPE: DNA
<213> ORGANISM: Chlamydia trachomatis MoPn

<400> SEQUENCE: 6

```
gctacaaaaa gtggaagaaa tcttttaaat cgtcgtcgcc gtcacggcag acattcctta     60
attgatctct aagatctttc atttgtgcat cggttaactc tacctaaaag tgcccgccta    120
ttgaaacgta acaatttgt ttacgtgcag cgttgtgggc aatattgtcg tactgatcag    180
gcaactttac gaatagttcc ttctcgtcat tcgaacatcc gtaaagtagg ggttactgtt    240
tctaaaaaat ttgggaaagc ccatcagcgc aatcgcttta aaagaattgt gcgagaggct    300
tttaggcatg tgcgaccaaa tcttcccgca tgtcaagtgg tagtgtctcc taaaggggc    360
actctaccaa attttggtaa actatccgcg gatcttctta agcatattcc agaggctttg    420
cctctcgtta cttcttctaa gtagtttttt attttggtca aaaataaaa aaccattcca    480
cgctatagag gcatggaatg ggaa                                           504
```

<210> SEQ ID NO 7
<211> LENGTH: 492
<212> TYPE: DNA
<213> ORGANISM: Vibrio cholerae stereotype 01, Biotype E1

-continued

<400> SEQUENCE: 7

```
ggcagcgtgg gccgataagt ggactaataa accactggta aagttttaca ataccaatgg      60
ctaaccacga aagggcgag agaggcgttg ccatagtttg ccaagcaagt taaacagttc      120
ttcattgctc aaatcttgcg cgctctttt ggcgatgaca acaaaatctt tgttagccag      180
ttgattttga tgtaagcgaa agctttctct gcaaatacgt ttgaatcgat tacggccgac      240
ggcagttttg atctgctttt taggaaccgc gagtcccaaa cgaggatgag aaaggttatt      300
agcgcgagcg atgattgtga gatgaggaga accagcactg tgagcttgct ggaagacttt      360
ttgataatgt tcgggagtta acaaacgtaa ctcccgattg aatgcgtacg tactcaaaat      420
aattcgagat tattttgaca ggcgcttacg gccttttgca cgacgtgcat tcagaacttt      480
acgaccgttc gc                                                         492
```

<210> SEQ ID NO 8
<211> LENGTH: 492
<212> TYPE: DNA
<213> ORGANISM: Neisseria gonorrhoea FA 1090

<400> SEQUENCE: 8

```
atgttccttg tatgggaaac ccgttgccgt ctgaaccttg cctgcagggt accgttctga      60
tcatacctgt ttcccgcatc cggttgcggg gttgccgaac atgagttgtg ccagttccgc      120
ccttgcctgt tttgcggtag ccctgtcgaa tttccggcgg acgcgcacga cgaaatcctg      180
aggcggcagc cggttttgt tcaatctgaa ccagtcgcgg atgacgcgtt tcatatagtt      240
ccgctcgttg gcgcgtttgg cggttttttt gccgaccacc agaccgatgc ggggatggtc      300
cagcccgttg ccgtttgagc gcgaaacttg cagcaggtcg cggctgcggc ggtttctgaa      360
tgcaaaaacg gatgaaaat catccgtttt taacaagcgg tactgccttc gaagcggta      420
gtccaaaatt acactgccag gcgtttgcgg cctttggcac ggcgtgcggc caatactgcg      480
cgtccgccgc gt                                                         492
```

<210> SEQ ID NO 9
<211> LENGTH: 492
<212> TYPE: DNA
<213> ORGANISM: Neisseria meningitidis serogroup A strain Z 2491

<400> SEQUENCE: 9

```
tgttccttag tatgggaaac ccgttgccgt ctgaaccttg cctgcagagt accgttctga      60
tcatgcctgt ttcctgcatc cggttgcggg gttgccgaac atgagttgtg ccagttccgc      120
ccttgcctgt tttgcggtag ccctgtcgaa tttacgcgg acgcgcacga cgaaatcctg      180
cggcggcagc cggttttgt tcaatctgaa ccagtcgcgg atgacgcgct tcatataatt      240
tcgttcgttg gcgcgtttgg cggttttttt gccgaccacc agaccgatgc ggggatgatc      300
cagcccgttg ccgtttgaac gcgaaacttg cagcaggtcg cggctgcggc ggtttctgaa      360
tgcaaaaacg gatgaaaat catccgtttt caacaagcgg tactgccttc gaagcggta      420
gtccaaaatt acaccgccag gcgtttgcgg cctttggcgc gccgtgcggc caatactgcg      480
cgtccgccgc gc                                                         492
```

<210> SEQ ID NO 10
<211> LENGTH: 462
<212> TYPE: DNA
<213> ORGANISM: Streptococcus pyogenes M1

-continued

```
<400> SEQUENCE: 10
gttacctcac cacgaccaca ggccactaat aatagaacta aggggactat tcttgcaatt      60
ttaatgtttt tcttcactct caaaacctt ctcaagcaat tgtgctaact ttaaaacatg      120
atgtaaattt tgttgaagct cttgatactc caaagattcg acaccttac gggcaatcac      180 cacgaaatcc tctgacttca gctgatgccc taatgccatg ataacatgac gtatctttcg    240
tttgactgca tttctggtga ctgcatttcc tatttttta ccgacagaaa tacccacacg      300
gaagtggtct tggcctctat ttaaatgata aatgacaaat tttcgatttg ctgtacttt     360 tccatcctta aatatggctt ggaaatcttt ctcacgcttg acacgatagg tcttcttcaa    420
aatttaactc caatatctaa attattacca ttataccaca tc                        462

<210> SEQ ID NO 11
<211> LENGTH: 492
<212> TYPE: DNA
<213> ORGANISM: Bordetella pertussis Tohama I

<400> SEQUENCE: 11
ccacccaggg gctgaggaag taccggtaaa accggatcgg ggcgataagc agtctcctga     60
tcatcgcgct atccgtgtga agtgagcatc tacttcggcg cgcgccgagc gtttcagggc    120
cgtgaggctt gccggtgtca gcttgctgtg cagccgcacc acgtaatcct gggccggcag    180
ggcaagccgg cgagcccgga acgcttcgcg gatgacccgc ttcaaggtat tgcgcgtcac    240
ggcgcgggcg gcaaaacgct tggcgatcac caggcccagg cgcgcgcgcg ccggctggtc    300
atcagcaggg gcacagggcg aggcgctgac aataaagaaa gccctcgggg ccagtcgccg    360
gcctttgagg gcggcggcaa actcggaggg gcgatgcaat cgcgcctccg cagggagcgt    420
ggcgcgcggc atgggtgacg tgacggagac tggcgacggg gccggcggcg atgctcctgt    480
tacaggcaat cc                                                        492

<210> SEQ ID NO 12
<211> LENGTH: 534
<212> TYPE: DNA
<213> ORGANISM: Porphyromonas gingivalis W83

<400> SEQUENCE: 12
agaagaaaat ggggagcagt aagagttgca cgagaaaagc cttgatcagt cgcatcgtat     60
ttactcgttt ttcaaagccg atgaaggtac atttccggca attctgatca gactcttttg    120
catcgctctc tccactgtac gaaagtcagg aagttcatcc gatactacca taatgcaat    180 agtagcatag atctgtctct cttggaggac atcgttcagg aggtgtttgt tgagccgata    240
agcctccctg accaaacgct tgaccctatt gcgcttcacg gctcgcctaa accttttct    300 tgctacgctt accagcatgg aggaatatgc aactcgatgc tccgatccca gacggtagac    360
tacgcgtaga ggataaacga caaacgcctt gccttcgcca aagaccgtat tgatttcatc    420
gcgaagatag aggcgttcgc ttttggatag gccgaatgta ggcggagagg tcatttcccg    480
ttgaggtaat cctctaatgc catagccata gaaggatatt gctcggtcgg cgca          534

<210> SEQ ID NO 13
<211> LENGTH: 495
<212> TYPE: DNA
<213> ORGANISM: Streptococcus pneumoniae Type 4

<400> SEQUENCE: 13
tcgctagtta ccccattagt cgcacaggct gtcatgatta acagagacag tcctagcaaa     60
```

-continued

```
ctagtcaact ttagtttctt tttcactccc atttccttcc cggtaaatct ttgataatttt      120 taatacatgg agtagatttt tctccatctc tgcgtatccc aaggtttcga ctccttttcg      180
agcaatgaca acaaagtcga catcttctac cagactccct tttgcattct ggataatatg      240
ccgaatccgt cgcttaattt gatttctagt gacggcattc cccagttttt tgctaactga      300
tagacctact cgaaaacggt ttttctggtt ttctaattgg tagaccacaa atttgcgatt      360
agcaaaactt gtcccctcct tgaaaatcgc cttaaaatct ttctctcttt ttacacgaaa      420 gttttttcttc aaaactcaac tccatctatt aaattactac tattatacca tattttttcaa    480 aaaagccaat catag                                                      495
```

<210> SEQ ID NO 14
<211> LENGTH: 465
<212> TYPE: DNA
<213> ORGANISM: Clostridium difficile 630 (epidemic type x)

<400> SEQUENCE: 14

```
tcctttaata tataaattat tttattcaaa gtcattaacc tccatatttta tagcatacaa      60 ttaaatagaa atatccgttc ttttaactaa attttttata gacttgtcta tgtctttaaa     120
agtagcatcc ttactagata cccttgctat aaatactata tcatatccag gcttaatttt     180
ttcatcaata tttaatctgt aggcttcttt tattaatctt cttactctat tcctagtaat     240
agcttttcct acttttttg aaacagaaat acctactcta ctataatctg atttattttt     300
aagtatatat attactaaat atttgtttgc aaaagatttg ccgtgtttat atactttttct   360 aaaatcagag tcttttttca acccttttagt cctattaaag tccatagtta acctccataa    420
acacagctat gaatcgtaat tatttacaca aaaaggccac ctttg                     465
```

<210> SEQ ID NO 15
<211> LENGTH: 447
<212> TYPE: DNA
<213> ORGANISM: Camphylobacter jejuni NCTC

<400> SEQUENCE: 15

```
aagcagcggg ttttaaaggg cttaagaatt tctgataaaa acggagtatt tttaggcata      60
tcatttgaaa cattctagtt ttttcaatcc ccattttaga ttttttttcta acctagaaaa     120 agaaagttca gtgatttcat ttttagctac aaaaatatat ttgccatctt gaagatatct     180
ttcaaactta gcaaacaaag ctcttaaaat tcgttttgaa cgatttctaa ccactgctttt    240 tccaactttt ttactagcaa caactgctat ttttttttca taactattca gataaaaaat     300
gatcacacct tcgcaatgcc attttttgcc tactttatat acagatgaaa attcctcgtt     360
tgtgctaaat ttatcaaaat ttttcacaca gcaagtcttt ttctaccttt agcgcgtctt     420
gcattgatca ctttgcgacc attttta                                         447
```

<210> SEQ ID NO 16
<211> LENGTH: 480
<212> TYPE: DNA
<213> ORGANISM: Baccillus anthracis Ames

<400> SEQUENCE: 16

```
taaacctaat ttcttttttca aagcctactc ctccttgtat cggtatgtat atagtgtaat      60
tcatttcctt acgctacttt ttattctttt cataccagag cgtttaaaga catgaattaa     120
gcttttcttt aattcttcat atgtcatctc tgcacaaggc ttccttgcta ttataacaaa     180
```

| atcttttcca | gaatctatct | catcttttaa | ttctgtgatc | gactggcgaa | tcatacgttt | 240 |
| aattcggtta | cgcactactg | catttcctat | cttcttgctg | acagaaaggc | caatacgaaa | 300 |
| gtttggctgc | tcttctttat | ctagttgata | gacaacaaat | tgacgattcg | cattcgattt | 360 |
| tccttttga | aaaaccgtct | ggaattcatc | attctttttt | atacgatgtt | ttttcttcat | 420 |
| atcaattgac | actcctgtag | ttcatcagcg | gaaattcact | attattagaa | aaaaagacca | 480 |

<210> SEQ ID NO 17
<211> LENGTH: 480
<212> TYPE: DNA
<213> ORGANISM: Mycobacterium avium 104

<400> SEQUENCE: 17

| gtccgcgggc | gacggttcgg | ccggcgccgc | gaatggccgc | gcccgaccgc | gccggtccgg | 60 |
| tcacggcccg | gttcccgccg | gcatgcgccg | caggcaccgc | tgcagttcct | gcgccaggcg | 120 |
| cgccgacgac | gcgtccggc | ttccgggcag | cgcgcgaatc | accagccggt | cggatggttc | 180 |
| gagttcgccg | agcagggccc | gggccacgtg | acgcagccgg | cgggccacgc | ggtgtcgttg | 240 |
| caccgccgtc | ccgacggcct | tcccgacgac | cagcccgacc | cgtgggcccg | cggattcgtc | 300 |
| gtcgggttcg | gagtcgcgcc | ggaggtggac | gacgatgtcg | ggctgcgcca | tgcgggttcc | 360 |
| gtgcttcacc | gtcgcgtcaa | actcggttga | ccgcgtcatg | cggttgcgtg | cgggaagcac | 420 |
| cgcgaaagac | ctgacgtgcg | atcaggcaga | gagcgcgcgg | cgacccttgc | ggcgccgacc | 480 |

<210> SEQ ID NO 18
<211> LENGTH: 474
<212> TYPE: DNA
<213> ORGANISM: Staphylococcus aureus NCTC 8325

<400> SEQUENCE: 18

| gttataagct | caatagaagt | ttaaatatag | cttcaaataa | aaacgataaa | taagcgagtg | 60 |
| atgttattgg | aaaaagctta | ccgaattaaa | aagaatgcag | attttcagag | aatatataaa | 120 |
| aaaggtcatt | ctgtagccaa | cagacaattt | gttgtataca | cttgtaataa | taaagaaata | 180 |
| gaccattttc | gcttaggtat | tagtgtttct | aaaaaactag | gtaatgcagt | gttaagaaac | 240 |
| aagattaaaa | gagcaatacg | tgaaaatttc | aaagtacata | agtcgcatat | attggccaaa | 300 |
| gatattattg | taatagcaag | acagccagct | aaagatatga | cgactttaca | aatacagaat | 360 |
| agtcttgagc | acgtacttaa | aattgccaaa | gttttttaata | aaaagattaa | gtaaggatag | 420 |
| ggtaggggaa | ggaaaacatt | aaccactcaa | cacatcccga | agtcttacct | caga | 474 |

<210> SEQ ID NO 19
<211> LENGTH: 474
<212> TYPE: DNA
<213> ORGANISM: Staphylococcus aureus COL

<400> SEQUENCE: 19

| gttataagct | caatagaagt | ttaaatatag | cttcaaataa | aaacgataaa | taagcgagtg | 60 |
| atgttattgg | aaaaagctta | ccgaattaaa | aagaatgcag | attttcagag | aatatataaa | 120 |
| aaaggtcatt | ctgtagccaa | cagacaattt | gttgtataca | cttgtaataa | taaagaaata | 180 |
| gaccattttc | gcttaggtat | tagtgtttct | aaaaaactag | gtaatgcagt | gttaagaaac | 240 |
| aagattaaaa | gagcaatacg | tgaaaatttc | aaagtacata | agtcgcatat | attggccaaa | 300 |
| gatattattg | taatagcaag | acagccagct | aaagatatga | cgactttaca | aatacagaat | 360 |
| agtcttgagc | acgtacttaa | aattgccaaa | gttttttaata | aaaagattaa | gtaaggatag | 420 |

```
ggtagggaa ggaaaacatt aaccactcaa cacatcccga agtcttacct caga          474
```

<210> SEQ ID NO 20
<211> LENGTH: 119
<212> TYPE: PRT
<213> ORGANISM: Streptococcus mutans UAB159

<400> SEQUENCE: 20

```
Val Leu Lys Lys Ala Tyr Arg Val Lys Ser Asp Lys Asp Phe Gln Ala
 1               5                  10                  15

Ile Phe Thr Glu Gly Arg Ser Val Ala Asn Arg Lys Phe Val Val Tyr
            20                  25                  30

Ser Leu Glu Lys Asp Gln Ser His Tyr Arg Val Gly Leu Ser Val Gly
        35                  40                  45

Lys Arg Leu Gly Asn Ala Val Arg Asn Ala Ile Lys Arg Lys Leu
 50                  55                  60

Arg His Val Leu Met Glu Leu Gly Pro Tyr Leu Gly Thr Gln Asp Phe
 65                  70                  75                  80

Val Val Ile Ala Arg Lys Gly Val Glu Glu Leu Asp Tyr Ser Thr Met
                85                  90                  95

Lys Lys Asn Leu Val His Val Leu Lys Leu Ala Lys Leu Tyr Gln Glu
            100                 105                 110

Gly Ser Ile Arg Glu Lys Glu
        115
```

<210> SEQ ID NO 21
<211> LENGTH: 119
<212> TYPE: PRT
<213> ORGANISM: Klebsiella pneumoniae M6H 78578

<400> SEQUENCE: 21

```
Val Val Lys Leu Ala Phe Pro Arg Glu Leu Arg Leu Leu Thr Pro Ser
 1               5                  10                  15

His Phe Thr Phe Val Phe Gln Gln Pro Gln Arg Ala Gly Thr Pro Gln
            20                  25                  30

Ile Thr Ile Leu Gly Arg Leu Asn Ser Leu Gly His Pro Arg Ile Gly
        35                  40                  45

Leu Thr Val Ala Lys Lys Asn Val Lys Arg Ala His Glu Arg Asn Arg
    50                  55                  60

Ile Lys Arg Leu Thr Arg Glu Ser Phe Arg Leu Arg Gln His Glu Leu
 65                  70                  75                  80

Pro Pro Met Asp Phe Val Val Ala Lys Arg Gly Val Ala Asp Leu
                85                  90                  95

Asp Asn Arg Ala Leu Ser Glu Ala Leu Glu Lys Leu Trp Arg Arg His
            100                 105                 110

Cys Arg Leu Ala Arg Gly Ser
        115
```

<210> SEQ ID NO 22
<211> LENGTH: 110
<212> TYPE: PRT
<213> ORGANISM: Salmonella paratyphi A AATC 9150

<400> SEQUENCE: 22

```
Val Thr Phe Val Asn Ser Arg Ser Phe His Ile Arg Leu Pro Ala Thr
 1               5                  10                  15

Ser Thr Gly Cys Thr Pro Gln Ile Thr Ile Leu Gly Arg Leu Asn Ser
```

```
                  20                  25                  30
Leu Gly His Pro Arg Ile Gly Leu Thr Val Ala Lys Lys Asn Val Arg
         35                  40                  45

Arg Ala His Glu Arg Asn Arg Ile Lys Arg Leu Thr Arg Glu Ser Phe
 50                  55                  60

Arg Leu Arg Gln His Glu Leu Pro Ala Met Asp Phe Val Val Ala
 65                  70                  75                  80

Lys Lys Gly Val Ala Asp Leu Asp Asn Arg Ala Leu Ser Glu Ala Leu
                 85                  90                  95

Glu Lys Leu Trp Arg Arg His Cys Arg Leu Ala Arg Gly Ser
             100                 105                 110

<210> SEQ ID NO 23
<211> LENGTH: 135
<212> TYPE: PRT
<213> ORGANISM: Pseudomonas aeruginosa PAO1

<400> SEQUENCE: 23

Val Val Ser Arg Asp Phe Asp Arg Asp Lys Arg Leu Leu Thr Ala Arg
 1               5                  10                  15

Gln Phe Ser Ala Val Phe Asp Ser Pro Thr Gly Lys Val Pro Gly Lys
                 20                  25                  30

His Val Leu Leu Leu Ala Arg Glu Asn Gly Leu Asp His Pro Arg Leu
             35                  40                  45

Gly Leu Val Ile Gly Lys Lys Asn Val Lys Leu Ala Val Gln Arg Asn
         50                  55                  60

Arg Leu Lys Arg Leu Ile Arg Glu Ser Phe Arg His Asn Gln Glu Thr
 65                  70                  75                  80

Leu Ala Gly Trp Asp Ile Val Ile Ala Arg Lys Gly Leu Gly Glu
                 85                  90                  95

Leu Glu Asn Pro Glu Leu His Gln Gln Phe Gly Lys Leu Trp Lys Arg
             100                 105                 110

Leu Leu Arg Asn Arg Pro Arg Thr Glu Ser Pro Ala Asp Ala Pro Gly
         115                 120                 125

Val Ala Asp Gly Thr His Ala
         130                 135

<210> SEQ ID NO 24
<211> LENGTH: 129
<212> TYPE: PRT
<213> ORGANISM: Corynebacterium diphtheriae

<400> SEQUENCE: 24

Val Thr Leu Thr Ser Ser Asn Arg Thr Thr Val Leu Pro Ser Gln His
 1               5                  10                  15

Lys Leu Ser Asn Ser Glu Gln Phe Arg Ala Thr Ile Arg Lys Gly Lys
                 20                  25                  30

Arg Ala Gly Arg Ser Thr Val Val Leu His Phe Tyr Ala Glu Ala Thr
         35                  40                  45

Ala Gly Asn Leu Ala Thr Ala Gly Gly Pro Arg Phe Gly Leu Val Val
         50                  55                  60

Ser Lys Ala Val Gly Asn Ala Val Thr Arg His Arg Val Ser Arg Gln
 65                  70                  75                  80

Leu Arg His Val Val Ile Ala Met Lys Asp Gln Phe Pro Ala Ser Ser
                 85                  90                  95

His Val Val Val Arg Ala Ile Pro Pro Ala Ala Thr Ala Ser Tyr Glu
```

-continued

```
                    100                 105                 110
Glu Leu Arg Ala Asp Val Gln Ala Ala Leu Asp Lys Leu Asn Arg Lys
        115                 120                 125
Arg

<210> SEQ ID NO 25
<211> LENGTH: 119
<212> TYPE: PRT
<213> ORGANISM: Chlamydia trachomatis MoPn

<400> SEQUENCE: 25

Val His Arg Leu Thr Leu Pro Lys Ser Ala Arg Leu Leu Lys Arg Lys
  1               5                  10                  15

Gln Phe Val Tyr Val Gln Arg Cys Gly Gln Tyr Cys Arg Thr Asp Gln
             20                  25                  30

Ala Thr Leu Arg Ile Val Pro Ser Arg His Ser Asn Ile Arg Lys Val
         35                  40                  45

Gly Val Thr Val Ser Lys Lys Phe Gly Lys Ala His Gln Arg Asn Arg
     50                  55                  60

Phe Lys Arg Ile Val Arg Glu Ala Phe Arg His Val Arg Pro Asn Leu
 65                  70                  75                  80

Pro Ala Cys Gln Val Val Ser Pro Lys Gly Gly Thr Leu Pro Asn
                 85                  90                  95

Phe Gly Lys Leu Ser Ala Asp Leu Leu Lys His Ile Pro Glu Ala Leu
            100                 105                 110

Pro Leu Val Thr Ser Ser Lys
        115

<210> SEQ ID NO 26
<211> LENGTH: 122
<212> TYPE: PRT
<213> ORGANISM: Vibrio cholerae stereotype 01, Biotype El Tor

<400> SEQUENCE: 26

Ser Arg Ile Ile Leu Ser Thr Tyr Ala Phe Asn Arg Glu Leu Arg Leu
  1               5                  10                  15

Leu Thr Pro Glu His Tyr Gln Lys Val Phe Gln Gln Ala His Ser Ala
             20                  25                  30

Gly Ser Pro His Leu Thr Ile Ile Ala Arg Ala Asn Asn Leu Ser His
         35                  40                  45

Pro Arg Leu Gly Leu Ala Val Pro Lys Lys Gln Ile Lys Thr Ala Val
     50                  55                  60

Gly Arg Asn Arg Phe Lys Arg Ile Cys Arg Glu Ser Phe Arg Leu His
 65                  70                  75                  80

Gln Asn Gln Leu Ala Asn Lys Asp Phe Val Val Ile Ala Lys Lys Ser
                 85                  90                  95

Ala Gln Asp Leu Ser Asn Glu Glu Leu Phe Asn Leu Leu Gly Lys Leu
            100                 105                 110

Trp Gln Arg Leu Ser Arg Pro Ser Arg Gly
        115                 120

<210> SEQ ID NO 27
<211> LENGTH: 123
<212> TYPE: PRT
<213> ORGANISM: Neisseria gonorrhoea FA 1090

<400> SEQUENCE: 27
```

Val Ile Leu Asp Tyr Arg Phe Gly Arg Gln Tyr Arg Leu Leu Lys Thr
1               5                   10                  15

Asp Asp Phe Ser Ser Val Phe Ala Phe Arg Asn Arg Arg Ser Arg Asp
            20                  25                  30

Leu Leu Gln Val Ser Arg Ser Asn Gly Asn Gly Leu Asp His Pro Arg
        35                  40                  45

Ile Gly Leu Val Val Gly Lys Lys Thr Ala Lys Arg Ala Asn Glu Arg
    50                  55                  60

Asn Tyr Met Lys Arg Val Ile Arg Asp Trp Phe Arg Leu Asn Lys Asn
65                  70                  75                  80

Arg Leu Pro Pro Gln Asp Phe Val Val Arg Val Arg Arg Lys Phe Asp
                85                  90                  95

Arg Ala Thr Ala Lys Gln Ala Arg Ala Glu Leu Ala Gln Leu Met Phe
            100                 105                 110

Gly Asn Pro Ala Thr Gly Cys Gly Lys Gln Val
            115                 120

<210> SEQ ID NO 28
<211> LENGTH: 123
<212> TYPE: PRT
<213> ORGANISM: Neisseria meningitidis serotype A Strain Z 2491

<400> SEQUENCE: 28

Val Ile Leu Asp Tyr Arg Phe Gly Arg Gln Tyr Arg Leu Leu Lys Thr
1               5                   10                  15

Asp Asp Phe Ser Ser Val Phe Ala Phe Arg Asn Arg Arg Ser Arg Asp
            20                  25                  30

Leu Leu Gln Val Ser Arg Ser Asn Gly Asn Gly Leu Asp His Pro Arg
        35                  40                  45

Ile Gly Leu Val Val Gly Lys Lys Thr Ala Lys Arg Ala Asn Glu Arg
    50                  55                  60

Asn Tyr Met Lys Arg Val Ile Arg Asp Trp Phe Arg Leu Asn Lys Asn
65                  70                  75                  80

Arg Leu Pro Pro Gln Asp Phe Val Val Arg Val Arg Arg Lys Phe Asp
                85                  90                  95

Arg Ala Thr Ala Lys Gln Ala Arg Ala Glu Leu Ala Gln Leu Met Phe
            100                 105                 110

Gly Asn Pro Ala Thr Gly Cys Arg Lys Gln Ala
            115                 120

<210> SEQ ID NO 29
<211> LENGTH: 113
<212> TYPE: PRT
<213> ORGANISM: Streptococcus pyogenes M1

<400> SEQUENCE: 29

Val Lys Arg Glu Lys Asp Phe Gln Ala Ile Phe Lys Asp Gly Lys Ser
1               5                   10                  15

Thr Ala Asn Arg Lys Phe Val Ile Tyr His Leu Asn Arg Gly Gln Asp
            20                  25                  30

His Phe Arg Val Gly Ile Ser Val Gly Lys Lys Ile Gly Asn Ala Val
        35                  40                  45

Thr Arg Asn Ala Val Lys Arg Lys Ile Arg His Val Ile Met Ala Leu
    50                  55                  60

Gly His Gln Leu Lys Ser Glu Asp Phe Val Ile Ala Arg Lys Gly
65                  70                  75                  80

-continued

Val Glu Ser Leu Glu Tyr Gln Glu Leu Gln Gln Asn Leu His His Val
                85                  90                  95

Leu Lys Leu Ala Gln Leu Leu Glu Lys Gly Phe Glu Ser Glu Lys
            100                 105                 110

His

<210> SEQ ID NO 30
<211> LENGTH: 123
<212> TYPE: PRT
<213> ORGANISM: Bordetella pertussis Tohama I

<400> SEQUENCE: 30

Met Pro Arg Ala Thr Leu Pro Ala Glu Ala Arg Leu His Arg Pro Ser
  1               5                  10                  15

Glu Phe Ala Ala Ala Leu Lys Gly Arg Arg Leu Ala Arg Gly Ala Phe
                 20                  25                  30

Phe Ile Val Ser Ala Ser Pro Cys Ala Pro Ala Asp Asp Gln Pro Ala
             35                  40                  45

Arg Ala Arg Leu Gly Leu Val Ile Ala Lys Arg Phe Ala Ala Arg Ala
         50                  55                  60

Val Thr Arg Asn Thr Leu Lys Arg Val Ile Arg Glu Ala Phe Arg Ala
 65                  70                  75                  80

Arg Arg Leu Ala Leu Pro Ala Gln Asp Tyr Val Val Arg Leu His Ser
                 85                  90                  95

Lys Leu Thr Pro Ala Ser Leu Thr Ala Leu Lys Arg Ser Ala Arg Ala
            100                 105                 110

Glu Val Asp Ala His Phe Thr Arg Ile Ala Arg
            115                 120

<210> SEQ ID NO 31
<211> LENGTH: 137
<212> TYPE: PRT
<213> ORGANISM: Porphyromonas gingivalis W83

<400> SEQUENCE: 31

Met Thr Ser Pro Pro Thr Phe Gly Leu Ser Lys Ser Glu Arg Leu Tyr
  1               5                  10                  15

Leu Arg Asp Glu Ile Asn Thr Val Phe Gly Glu Gly Lys Ala Phe Val
                 20                  25                  30

Val Tyr Pro Leu Arg Val Val Tyr Arg Leu Gly Ser Glu His Arg Val
             35                  40                  45

Ala Tyr Ser Ser Met Leu Val Ser Val Ala Lys Lys Arg Phe Arg Arg
         50                  55                  60

Ala Val Lys Arg Asn Arg Val Lys Arg Leu Val Arg Glu Ala Tyr Arg
 65                  70                  75                  80

Leu Asn Lys His Leu Leu Asn Asp Val Leu Gln Glu Arg Gln Ile Tyr
                 85                  90                  95

Ala Thr Ile Ala Phe Met Val Val Ser Asp Glu Leu Pro Asp Phe Arg
            100                 105                 110

Thr Val Glu Arg Ala Met Gln Lys Ser Leu Ile Arg Ile Ala Gly Asn
            115                 120                 125

Val Pro Ser Ser Ala Leu Lys Asn Glu
            130                 135

<210> SEQ ID NO 32
<211> LENGTH: 124
<212> TYPE: PRT

<213> ORGANISM: Streptococcus pneumoniae Type4

<400> SEQUENCE: 32

```
Val Leu Lys Lys Asn Phe Arg Val Lys Arg Glu Lys Asp Phe Lys Ala
1               5                   10                  15
Ile Phe Lys Glu Gly Thr Ser Phe Ala Asn Arg Lys Phe Val Val Tyr
            20                  25                  30
Gln Leu Glu Asn Gln Lys Asn Arg Phe Arg Val Gly Leu Ser Val Ser
        35                  40                  45
Lys Lys Leu Gly Asn Ala Val Thr Arg Asn Gln Ile Lys Arg Arg Ile
50                  55                  60
Arg His Ile Ile Gln Asn Ala Lys Gly Ser Leu Val Glu Asp Val Asp
65                  70                  75                  80
Phe Val Val Ile Ala Arg Lys Gly Val Glu Thr Leu Gly Tyr Ala Glu
                85                  90                  95
Met Glu Lys Asn Leu Leu His Val Leu Lys Leu Ser Lys Ile Tyr Arg
            100                 105                 110
Glu Gly Asn Gly Ser Glu Lys Glu Thr Lys Val Asp
        115                 120
```

<210> SEQ ID NO 33
<211> LENGTH: 114
<212> TYPE: PRT
<213> ORGANISM: Clostridium difficile 630 (epidemic type X)

<400> SEQUENCE: 33

```
Met Asp Phe Asn Arg Thr Lys Gly Leu Lys Lys Asp Ser Asp Phe Arg
1               5                   10                  15
Lys Val Tyr Lys His Gly Lys Ser Phe Ala Asn Lys Tyr Leu Val Ile
            20                  25                  30
Tyr Ile Leu Lys Asn Lys Ser Asp Tyr Ser Arg Val Gly Ile Ser Val
        35                  40                  45
Ser Lys Lys Val Gly Lys Ala Ile Thr Arg Asn Arg Val Arg Arg Leu
50                  55                  60
Ile Lys Glu Ala Tyr Arg Leu Asn Ile Asp Glu Lys Ile Lys Pro Gly
65                  70                  75                  80
Tyr Asp Ile Val Phe Ile Ala Arg Val Ser Ser Lys Asp Ala Thr Phe
                85                  90                  95
Lys Asp Ile Asp Lys Ser Ile Lys Asn Leu Val Lys Arg Thr Asp Ile
            100                 105                 110
Ser Ile
```

<210> SEQ ID NO 34
<211> LENGTH: 108
<212> TYPE: PRT
<213> ORGANISM: Camphylobacter jejuni NCTC

<400> SEQUENCE: 34

```
Val Lys Asn Phe Asp Lys Phe Ser Thr Asn Glu Glu Phe Ser Ser Val
1               5                   10                  15
Tyr Lys Val Gly Lys Lys Trp His Cys Glu Gly Val Ile Ile Phe Tyr
            20                  25                  30
Leu Asn Ser Tyr Glu Lys Lys Ile Ala Val Val Ala Ser Lys Lys Val
        35                  40                  45
Gly Lys Ala Val Val Arg Asn Arg Ser Lys Arg Ile Leu Arg Ala Leu
50                  55                  60
```

-continued

Phe Ala Lys Phe Glu Arg Tyr Leu Gln Asp Gly Lys Tyr Ile Phe Val
 65                  70                  75                  80

Ala Lys Asn Glu Ile Thr Glu Leu Ser Phe Ser Arg Leu Glu Lys Asn
                 85                  90                  95

Leu Lys Trp Gly Leu Lys Lys Leu Glu Cys Phe Lys
            100                 105

<210> SEQ ID NO 35
<211> LENGTH: 119
<212> TYPE: PRT
<213> ORGANISM: Bacillus anthracis Ames

<400> SEQUENCE: 35

Met Lys Lys Lys His Arg Ile Lys Lys Asn Asp Glu Phe Gln Thr Val
  1               5                  10                  15

Phe Gln Lys Gly Lys Ser Asn Ala Asn Arg Gln Phe Val Val Tyr Gln
                 20                  25                  30

Leu Asp Lys Glu Glu Gln Pro Asn Phe Arg Ile Gly Leu Ser Val Ser
                 35                  40                  45

Lys Lys Ile Gly Asn Ala Val Val Arg Asn Arg Ile Lys Arg Met Ile
 50                  55                  60

Arg Gln Ser Ile Thr Glu Leu Lys Asp Glu Ile Asp Ser Gly Lys Asp
 65                  70                  75                  80

Phe Val Ile Ile Ala Arg Lys Pro Cys Ala Glu Met Thr Tyr Glu Glu
                 85                  90                  95

Leu Lys Lys Ser Leu Ile His Val Phe Lys Arg Ser Gly Met Lys Arg
                100                 105                 110

Ile Lys Ser Ser Val Arg Lys
            115

<210> SEQ ID NO 36
<211> LENGTH: 119
<212> TYPE: PRT
<213> ORGANISM: Mycobacterium avium IO4

<400> SEQUENCE: 36

Val Leu Pro Ala Arg Asn Arg Met Thr Arg Ser Thr Glu Phe Asp Ala
  1               5                  10                  15

Thr Val Lys His Gly Thr Arg Met Ala Gln Pro Asp Ile Val Val His
                 20                  25                  30

Leu Arg Arg Asp Ser Glu Pro Asp Asp Glu Ser Ala Gly Pro Arg Val
                 35                  40                  45

Gly Leu Val Val Gly Lys Ala Val Gly Thr Ala Val Gln Arg His Arg
 50                  55                  60

Val Ala Arg Arg Leu Arg His Val Ala Arg Ala Leu Leu Gly Glu Leu
 65                  70                  75                  80

Glu Pro Ser Asp Arg Leu Val Ile Arg Ala Leu Pro Gly Ser Arg Thr
                 85                  90                  95

Ala Ser Ser Ala Arg Leu Ala Gln Glu Leu Gln Arg Cys Leu Arg Arg
                100                 105                 110

Met Pro Ala Gly Thr Gly Pro
            115

<210> SEQ ID NO 37
<211> LENGTH: 117
<212> TYPE: PRT
<213> ORGANISM: Staphylococcus aureus NCTC 8325

```
<400> SEQUENCE: 37

Met Leu Leu Glu Lys Ala Tyr Arg Ile Lys Lys Asn Ala Asp Phe Gln
1               5                   10                  15

Arg Ile Tyr Lys Lys Gly His Ser Val Ala Asn Arg Gln Phe Val Val
            20                  25                  30

Tyr Thr Cys Asn Asn Lys Glu Ile Asp His Phe Arg Leu Gly Ile Ser
        35                  40                  45

Val Ser Lys Lys Leu Gly Asn Ala Val Leu Arg Asn Lys Ile Lys Arg
    50                  55                  60

Ala Ile Arg Glu Asn Phe Lys Val His Lys Ser His Ile Leu Ala Lys
65                  70                  75                  80

Asp Ile Ile Val Ile Ala Arg Gln Pro Ala Lys Asp Met Thr Thr Leu
                85                  90                  95

Gln Ile Gln Asn Ser Leu Glu His Val Leu Lys Ile Ala Lys Val Phe
            100                 105                 110

Asn Lys Lys Ile Lys
        115

<210> SEQ ID NO 38
<211> LENGTH: 117
<212> TYPE: PRT
<213> ORGANISM: Staphylococcus aureus COL

<400> SEQUENCE: 38

Met Leu Leu Glu Lys Ala Tyr Arg Ile Lys Lys Asn Ala Asp Phe Gln
1               5                   10                  15

Arg Ile Tyr Lys Lys Gly His Ser Val Ala Asn Arg Gln Phe Val Val
            20                  25                  30

Tyr Thr Cys Asn Asn Lys Glu Ile Asp His Phe Arg Leu Gly Ile Ser
        35                  40                  45

Val Ser Lys Lys Leu Gly Asn Ala Val Leu Arg Asn Lys Ile Lys Arg
    50                  55                  60

Ala Ile Arg Glu Asn Phe Lys Val His Lys Ser His Ile Leu Ala Lys
65                  70                  75                  80

Asp Ile Ile Val Ile Ala Arg Gln Pro Ala Lys Asp Met Thr Thr Leu
                85                  90                  95

Gln Ile Gln Asn Ser Leu Glu His Val Leu Lys Ile Ala Lys Val Phe
            100                 105                 110

Asn Lys Lys Ile Lys
        115

<210> SEQ ID NO 39
<211> LENGTH: 360
<212> TYPE: DNA
<213> ORGANISM: Pasteurella multocida PM70

<400> SEQUENCE: 39
gtgattaagc tgaattttc gagggagtta cgtttgttaa ctccccttca ttttaaatac      60
gtcttcgaac agccgttccg tgctagtaca cctgaactta ccattcttgc tcgtcccaat    120
aatctcgctc atcctcgctt agggttaact gtcgcgaaaa agcatttaaa aaaagcacat    180
gatcgcaatc gcatcaaacg cttatgccga gaaagtttcc gcctagcaca gtataaactc    240
cccaattgcg attttgttat tgtggcgaaa cagggaattg gtaaattaga caacaggaca    300
ctcacacaaa cattggataa attatggcaa agacacattc gcttagctca aaaatcttga    360
```

-continued

<210> SEQ ID NO 40
<211> LENGTH: 372
<212> TYPE: DNA
<213> ORGANISM: Haemophilus ducreyi strain 35000HP

<400> SEQUENCE: 40
ttaatttttg ctttgtgctt gttgactgag gcgaatatga cgagtccata atttatctat 60
ggttgcgaaa agcgtagcat tatctagttt accaatcctc atgcttggca acaaagacaa 120
agtcaatatt aggtaattga tgttgtttta aacggaagct ttcccgcaca atacgttgat 180
ccgattgcga tcgtgagcac gttttaaatg ctttttagca acggttaacc caagacgagg 240
cgtattaacg caattttgac gagcaagaat agtaagttca gctgtgctag cacgatatgg 300
ttgttcaaac acggctttga attgaatggg agctaacaaa cgtagctccc gagaaaacgt 360
tagcttattc ac 372

<210> SEQ ID NO 41
<211> LENGTH: 360
<212> TYPE: DNA
<213> ORGANISM: Chamydia muridarum

<400> SEQUENCE: 41
gtgcatcggt taactctacc taaaagtgcc cgcctattga aacgtaaaca atttgtttac 60
gtgcagcgtt gtgggcaata ttgtcgtact gatcaggcaa ctttacgaat agttccttct 120
cgtcattcga acatccgtaa agtaggggtt actgtttcta aaaaatttgg gaaagcccat 180
cagcgcaatc gctttaaaag aattgtgcga gaggctttta ggcatgtgcg accaaatctt 240
cccgcatgtc aagtggtagt gtctcctaaa gggggcactc taccaaattt tggtaaacta 300
tccgcggatc ttcttaagca tattccagag gctttgcctc tcgttacttc ttctaagtag 360

<210> SEQ ID NO 42
<211> LENGTH: 420
<212> TYPE: DNA
<213> ORGANISM: Chlamidophila psittaci

<400> SEQUENCE: 42
gtgcatcgat caaccttacc caaatatgct cgtgtgttaa agagaaagca gtttctctac 60
atctcgcgag cgggatctca ctgtcaaggc agtcaggtta tttttcatgt tgctccatct 120
agatattctg gatgttgcaa gcttgggata actgtctcaa aaaaatttgg gaaagcgcat 180
aaaagaaatt attttaaacg tattgtgcgc gaggcttttc gtaaaaagcg tcactctctt 240
cctgcttgtc aaattgttgt tatgcctaaa aacaagcagc aacctaaatt tgaagatctg 300
cttcaagact ttgctcagca aattccagaa gcactcagta gcaaattagc aaaaaataag 360
cctacgactg gtgtcgaata tagtccaaag aatgagaaat gtgagtctgt acttccttag 420

<210> SEQ ID NO 43
<211> LENGTH: 357
<212> TYPE: DNA
<213> ORGANISM: Treponema denticola

<400> SEQUENCE: 43
tcataaagcc tcatcattat acattttcgc ttttaaaaag agggcggtaa gttgttctaa 60
acgaagagaa taagaatcct tttctgaaaa aaccagcagg ataatgtcgt ttcccgtttt 120
taacctatgt tttatatgtc tataggcctc ttttgatatt ctccgagacc tgttccgcat 180
cactgcggaa ccgaaacctc gtcgaaaagt acataagaat cgattgtact ccaatccatt 240

```
aggcaggatt aacaaactaa ctccgtttaa gctaagttta agaccttttt gaaatacggc   300
cttaatacat gaccgatccc ttaaccgttc ttcaccggaa aatgtaaaat tactcac      357

<210> SEQ ID NO 44
<211> LENGTH: 357
<212> TYPE: DNA
<213> ORGANISM: Enterococcus faecalis

<400> SEQUENCE: 44
ctactcaatt ccctctctta catctaatat tttagctaaa tttaacacat gtgttaaatt   60
agctttcact tcttcagacg ataacttttc caatcctgga cgtgcaatca cgataaaatc  120
aatttctgga gagatacggt cttttaattg aaataaactc gcgcggattt tccgcttcac  180
agcatttctt gtgaccgcgt ttccaatttt cttcccaaca gaaatcccca ctcgaaaatg  240
ggcttgttgt ggtttctcta aaacgtacac cacgaaacga cgatttgcac aagattgttt  300
tttattaaac acctgttgaa attcttttc tttcttgaca cggtaggact ttttcat     357

<210> SEQ ID NO 45
<211> LENGTH: 330
<212> TYPE: DNA
<213> ORGANISM: Legionella pneumophila

<400> SEQUENCE: 45
ctatttgccg tagcatgagg ctaattttc ccatgtttta tttaatttag tatttatacc    60
taaattggtt ttctttgcta gacctggtct tgccaaaatg attatatcta cagcaggcaa  120
gttagtatga cgaaaacttt ctctaagtag ccgtttaatg cgatttctgt catgagcctt  180
agctatcatt ttttttgaca atgctaaacc aaggcgtgca tagcctaact tatttctct   240 gaaaaggaaa ataaagtcat ctgtaggtat tttttcgcg ctttgaaaca cgaagtcaaa   300
atgatttttt tttaataagc ggtgcggctg                                    330

<210> SEQ ID NO 46
<211> LENGTH: 348
<212> TYPE: DNA
<213> ORGANISM: Staphylococcus epidermis

<400> SEQUENCE: 46
ctacttaatc ttttttattaa acacttttgc aattttaagc acatgctcta aactgctttg   60
aatctccagt gtattcatat cttttgctgg ttgcctcgca ataactataa tatcttagc   120 gataatattt tgcttatgca ctttaaaatt ctctcttatc gctcttttaa ttctatttct  180
tgtaacagcg ttgcccagtt tttttgagac acttattcct aagcgaaaat gttttaaatc  240
tctattttta taggtataga caacaaattg tctatttgca acagacttcc cattcttgta   300
tatcgcttga aagtctgaat ttctcttaat acgatatgct ttttccat                348

<210> SEQ ID NO 47
<211> LENGTH: 392
<212> TYPE: DNA
<213> ORGANISM: Mycobacterium smegmatis

<400> SEQUENCE: 47
tcatggggac gccctgcgct tcgagctcac ccgctcgagc gcttgaccca actgtcgttc    60
caaacgggac gacgtggcgt cacgactgct cggcctggcc cggatcacga tgagatcggc  120
agggtcaaga ccggatacga acgttttggc gacgtgccgc agacggcggg acacgcggtg  180
acgctccacc gcgttgccga cggctttgga cacgatcaga ccgatccgcg gcccgttcgc  240
```

-continued

```
gtcgccgtca tcgccgtcat cgccggcatt gcctgcgttg ctttcaaggc gcaacgcgtg    300
tacgacgaca tcgggttgcg cggcacgcac gccgcgactg acggtgacac tgaactccgc    360
ggaccgctca tccggtttcg agccggaagc ac                                  392
```

<210> SEQ ID NO 48
<211> LENGTH: 291
<212> TYPE: DNA
<213> ORGANISM: Burkholderia pseudomallei

<400> SEQUENCE: 48

```
cgcatgcagg cgcagcagaa tgtcccagcc ggcgaactcg gcgcgacgcg tacgaaacgc    60
ctcgcgggcg agccgcttga ccagattgcg cgtcaccgca cgcgcggcgt acttcttgcc    120
gatgacgagc ccaagacgcg catcgcgccc cgtcggcttg ccgtagatca cgaagtgcgc    180
ggtgcgccgc cagggacgca aacgaaaaac ggatgagaat tcatccgttt tcagaagtcg    240
cgcagctttg gggaaggcgg cggacgcttg caacggaatc gaaccccgga c             291
```

<210> SEQ ID NO 49
<211> LENGTH: 342
<212> TYPE: DNA
<213> ORGANISM: Ureaplasma urealyticum

<400> SEQUENCE: 49

```
ttatcttttt tctttgttaa taattcgttg aagaattatt ttaagattat tacaatttaa    60
aacaaaagaa ccatcaataa acgatggttt cactaagact acaatatcat aactttaat     120 gggaatatca gcagcaataa accatgcttt aatcaggcgt cgaattcgat tgcgttgtgt    180
tgctaattta aactttttttt tagaaatgct tatagctaag cgaacatttt ttagattggt   240
tttacgaaaa taaactacga tttgattaga atgaattttt tgttgtttct taattgtatc    300
aagtatatct tcatttttttt ttagactaat aaaattagcc at                      342
```

<210> SEQ ID NO 50
<211> LENGTH: 119
<212> TYPE: PRT
<213> ORGANISM: Pasteurella multocida PM70

<400> SEQUENCE: 50

```
Val Ile Lys Leu Asn Phe Ser Arg Glu Leu Arg Leu Thr Pro Leu
  1               5                  10                  15

His Phe Lys Tyr Val Phe Glu Gln Pro Phe Arg Ala Ser Thr Pro Glu
                 20                  25                  30

Leu Thr Ile Leu Ala Arg Pro Asn Asn Leu Ala His Pro Arg Leu Gly
             35                  40                  45

Leu Thr Val Ala Lys Lys His Leu Lys Lys Ala His Asp Arg Asn Arg
         50                  55                  60

Ile Lys Arg Leu Cys Arg Glu Ser Phe Arg Leu Ala Gln Tyr Lys Leu
 65                  70                  75                  80

Pro Asn Cys Asp Phe Val Ile Val Ala Lys Gln Gly Ile Gly Lys Leu
                 85                  90                  95

Asp Asn Arg Thr Leu Thr Gln Thr Leu Asp Lys Leu Trp Gln Arg His
            100                 105                 110

Ile Arg Leu Ala Gln Lys Ser
        115
```

<210> SEQ ID NO 51

-continued

<211> LENGTH: 123
<212> TYPE: PRT
<213> ORGANISM: Haemophilus ducreyi strain 35000HP

<400> SEQUENCE: 51

Val Asn Lys Leu Thr Phe Ser Arg Glu Leu Arg Leu Leu Ala Pro Ile
1 5 10 15

Gln Phe Lys Ala Val Phe Glu Gln Pro Tyr Arg Ala Ser Thr Ala Glu
20 25 30

Leu Thr Ile Leu Ala Arg Gln Asn Cys Val Asn Thr Pro Arg Leu Gly
35 40 45

Leu Thr Val Ala Lys Lys His Leu Lys Arg Ala His Asp Arg Asn Arg
50 55 60

Ile Lys Arg Ile Val Arg Glu Ser Phe Arg Leu Lys Gln His Gln Leu
65 70 75 80

Pro Asn Phe Asp Phe Val Phe Val Ala Lys His Gly Ile Gly Lys Leu
85 90 95

Asp Asn Ala Thr Leu Phe Ala Thr Ile Asp Lys Leu Trp Thr Arg His
100 105 110

Ile Arg Leu Ser Gln Gln Ala Gln Ser Lys Asn
115 120

<210> SEQ ID NO 52
<211> LENGTH: 119
<212> TYPE: PRT
<213> ORGANISM: Chlamydia muridarum

<400> SEQUENCE: 52

Met His Arg Leu Thr Leu Pro Lys Ser Ala Arg Leu Leu Lys Arg Lys
1 5 10 15

Gln Phe Val Tyr Val Gln Arg Cys Gly Gln Tyr Cys Arg Thr Asp Gln
20 25 30

Ala Thr Leu Arg Ile Val Pro Ser Arg His Ser Asn Ile Arg Lys Val
35 40 45

Gly Val Thr Val Ser Lys Lys Phe Gly Lys Ala His Gln Arg Asn Arg
50 55 60

Phe Lys Arg Ile Val Arg Glu Ala Phe Arg His Val Arg Pro Asn Leu
65 70 75 80

Pro Ala Cys Gln Val Val Val Ser Pro Lys Gly Gly Thr Leu Pro Asn
85 90 95

Phe Gly Lys Leu Ser Ala Asp Leu Leu Lys His Ile Pro Glu Ala Leu
100 105 110

Pro Leu Val Thr Ser Ser Lys
115

<210> SEQ ID NO 53
<211> LENGTH: 139
<212> TYPE: PRT
<213> ORGANISM: Chlamydophila psittaci

<400> SEQUENCE: 53

Val His Arg Ser Thr Leu Pro Lys Tyr Ala Arg Val Leu Lys Arg Lys
1 5 10 15

Gln Phe Leu Tyr Ile Ser Arg Ala Gly Ser His Cys Gln Gly Ser Gln
20 25 30

Val Ile Phe His Val Ala Pro Ser Arg Tyr Ser Gly Cys Cys Lys Leu
35 40 45

```
Gly Ile Thr Val Ser Lys Lys Phe Gly Lys Ala His Lys Arg Asn Tyr
 50                  55                  60

Phe Lys Arg Ile Val Arg Glu Ala Phe Arg Lys Lys Arg His Ser Leu
 65                  70                  75                  80

Pro Ala Cys Gln Ile Val Val Met Pro Lys Asn Lys Gln Gln Pro Lys
                 85                  90                  95

Phe Glu Asp Leu Leu Gln Asp Phe Ala Gln Gln Ile Pro Glu Ala Leu
                100                 105                 110

Ser Ser Lys Leu Ala Lys Asn Lys Pro Thr Thr Gly Val Glu Tyr Ser
                115                 120                 125

Pro Lys Asn Glu Lys Cys Glu Ser Val Leu Pro
    130                 135
```

<210> SEQ ID NO 54
<211> LENGTH: 118
<212> TYPE: PRT
<213> ORGANISM: Treponema denticola

<400> SEQUENCE: 54

```
Val Ser Asn Phe Thr Phe Ser Gly Glu Glu Arg Leu Arg Asp Arg Ser
 1               5                  10                  15

Cys Ile Lys Ala Val Phe Gln Lys Gly Leu Lys Leu Ser Leu Asn Gly
                 20                  25                  30

Val Ser Leu Leu Ile Leu Pro Asn Gly Leu Glu Tyr Asn Arg Phe Leu
                 35                  40                  45

Cys Thr Phe Arg Arg Gly Phe Gly Ser Ala Val Met Arg Asn Arg Ser
 50                  55                  60

Arg Arg Ile Ser Lys Glu Ala Tyr Arg His Ile Lys His Arg Leu Lys
 65                  70                  75                  80

Thr Gly Asn Asp Ile Ile Leu Leu Val Phe Ser Lys Asp Ser Tyr
                 85                  90                  95

Ser Leu Arg Leu Glu Gln Leu Thr Ala Leu Phe Leu Lys Ala Lys Met
                100                 105                 110

Tyr Asn Asp Glu Ala Leu
        115
```

<210> SEQ ID NO 55
<211> LENGTH: 118
<212> TYPE: PRT
<213> ORGANISM: Enterococcus faecalis

<400> SEQUENCE: 55

```
Met Lys Lys Ser Tyr Arg Val Lys Lys Glu Lys Glu Phe Gln Gln Val
 1               5                  10                  15

Phe Asn Lys Lys Gln Ser Cys Ala Asn Arg Arg Phe Val Val Tyr Val
                 20                  25                  30

Leu Glu Lys Pro Gln Gln Ala His Phe Arg Val Gly Ile Ser Val Gly
                 35                  40                  45

Lys Lys Ile Gly Asn Ala Val Thr Arg Asn Ala Val Lys Arg Lys Ile
                 50                  55                  60

Arg Ala Ser Leu Phe Gln Leu Lys Asp Arg Ile Ser Pro Glu Ile Asp
 65                  70                  75                  80

Phe Ile Val Ile Ala Arg Pro Gly Leu Glu Lys Leu Ser Ser Glu Glu
                 85                  90                  95

Val Lys Ala Asn Leu Thr His Val Leu Asn Leu Ala Lys Ile Leu Asp
                100                 105                 110
```

-continued

Val Arg Glu Gly Ile Glu
        115

<210> SEQ ID NO 56
<211> LENGTH: 109
<212> TYPE: PRT
<213> ORGANISM: Legionella pneumophila

<400> SEQUENCE: 56

Gln Pro His Arg Leu Leu Lys Lys Asn His Phe Asp Phe Val Phe Gln
1               5                   10                  15

Ser Ala Lys Lys Ile Pro Thr Asp Asp Phe Ile Phe Leu Phe Arg Glu
            20                  25                  30

Asn Lys Leu Gly Tyr Ala Arg Leu Gly Leu Ala Leu Ser Lys Lys Met
        35                  40                  45

Ile Ala Lys Ala His Asp Arg Asn Arg Ile Lys Arg Leu Leu Arg Glu
    50                  55                  60

Ser Phe Arg His Thr Asn Leu Pro Ala Val Asp Ile Ile Leu Ala
65                  70                  75                  80

Arg Pro Gly Leu Ala Lys Lys Thr Asn Leu Gly Ile Asn Thr Lys Leu
                85                  90                  95

Asn Lys Thr Trp Glu Lys Leu Ala Ser Cys Tyr Gly Lys
            100                 105

<210> SEQ ID NO 57
<211> LENGTH: 115
<212> TYPE: PRT
<213> ORGANISM: Staphylococcus epidermis

<400> SEQUENCE: 57

Met Glu Lys Ala Tyr Arg Ile Lys Arg Asn Ser Asp Phe Gln Ala Ile
1               5                   10                  15

Tyr Lys Asn Gly Lys Ser Val Ala Asn Arg Gln Phe Val Val Tyr Thr
            20                  25                  30

Tyr Lys Asn Arg Asp Leu Lys His Phe Arg Leu Gly Ile Ser Val Ser
        35                  40                  45

Lys Lys Leu Gly Asn Ala Val Thr Arg Asn Arg Ile Lys Arg Ala Ile
    50                  55                  60

Arg Glu Asn Phe Lys Val His Lys Gln Asn Ile Ile Ala Lys Asp Ile
65                  70                  75                  80

Ile Val Ile Ala Arg Gln Pro Ala Lys Asp Met Asn Thr Leu Glu Ile
                85                  90                  95

Gln Ser Ser Leu Glu His Val Leu Lys Ile Ala Lys Val Phe Asn Lys
            100                 105                 110

Lys Ile Lys
        115

<210> SEQ ID NO 58
<211> LENGTH: 130
<212> TYPE: PRT
<213> ORGANISM: Myobacterium smegnatis

<400> SEQUENCE: 58

Val Leu Pro Ala Arg Asn Arg Met Arg Arg Ser Ala Glu Phe Ser Val
1               5                   10                  15

Thr Val Ser Arg Gly Val Arg Ala Ala Gln Pro Asp Val Val His
            20                  25                  30

Ala Leu Arg Leu Glu Ser Asn Ala Gly Asn Ala Gly Asp Asp Gly Asp

-continued

```
                 35                  40                  45
Asp Gly Asp Ala Asn Gly Pro Arg Ile Gly Leu Ile Val Ser Lys Ala
            50                  55                  60

Val Gly Asn Ala Val Glu Arg His Arg Val Ser Arg Arg Leu Arg His
 65                  70                  75                  80

Val Ala Lys Thr Phe Val Ser Gly Leu Asp Pro Ala Asp Leu Ile Val
                85                  90                  95

Ile Arg Ala Arg Pro Ser Ser Arg Asp Ala Thr Ser Ser Arg Leu Glu
            100                 105                 110

Arg Gln Leu Gly Gln Ala Leu Glu Arg Val Ser Ser Lys Arg Arg Ala
            115                 120                 125

Ser Pro
    130

<210> SEQ ID NO 59
<211> LENGTH: 97
<212> TYPE: PRT
<213> ORGANISM: Burkholderia pseudomallei

<400> SEQUENCE: 59

Val Arg Gly Ser Ile Pro Leu Gln Ala Ser Ala Ala Phe Pro Lys Ala
  1               5                  10                  15

Ala Arg Leu Leu Lys Thr Asp Glu Phe Ser Ser Val Phe Arg Leu Arg
             20                  25                  30

Pro Trp Arg Arg Thr Ala His Phe Val Ile Tyr Gly Lys Pro Thr Gly
             35                  40                  45

Arg Asp Ala Arg Leu Gly Leu Val Ile Gly Lys Lys Tyr Ala Ala Arg
         50                  55                  60

Ala Val Thr Arg Asn Leu Val Lys Arg Leu Ala Arg Glu Ala Phe Arg
 65                  70                  75                  80

Thr Arg Arg Ala Glu Phe Ala Gly Trp Asp Ile Leu Leu Arg Leu His
                 85                  90                  95

Ala

<210> SEQ ID NO 60
<211> LENGTH: 113
<212> TYPE: PRT
<213> ORGANISM: Ureaplasma urealyticum

<400> SEQUENCE: 60

Met Ala Asn Phe Ile Ser Leu Lys Lys Asn Glu Asp Ile Leu Asp Thr
  1               5                  10                  15

Ile Lys Lys Gln Gln Lys Ile His Ser Asn Gln Ile Val Val Tyr Phe
             20                  25                  30

Arg Lys Thr Asn Leu Lys Asn Val Arg Leu Ala Ile Ser Ile Ser Lys
             35                  40                  45

Lys Lys Phe Lys Leu Ala Thr Gln Arg Asn Arg Ile Arg Arg Leu Ile
         50                  55                  60

Lys Ala Trp Phe Ile Ala Ala Asp Ile Pro Ile Lys Ser Tyr Asp Ile
 65                  70                  75                  80

Val Val Leu Val Lys Pro Ser Phe Ile Asp Gly Ser Phe Val Leu Asn
                 85                  90                  95

Cys Asn Asn Leu Lys Ile Ile Leu Gln Arg Ile Ile Asn Lys Glu Lys
             100                 105                 110

Arg
```

<210> SEQ ID NO 61
<211> LENGTH: 71
<212> TYPE: PRT
<213> ORGANISM: Escherichia coli

<400> SEQUENCE: 61

Leu Arg Leu Leu Thr Pro Ser Gln Phe Thr Phe Val Phe Arg Ile Gly
1               5                   10                  15

Leu Thr Val Ala Lys Lys Asn Val Arg Arg Ala His Glu Arg Asn Arg
            20                  25                  30

Ile Lys Arg Leu Thr Arg Glu Ser Phe Arg Leu Arg Gln His Glu Leu
        35                  40                  45

Asp Phe Val Val Val Ala Lys Lys Gly Val Ala Asp Leu Asp Asn Arg
    50                  55                  60

Ala Leu Ser Glu Ala Leu Glu
65                  70

<210> SEQ ID NO 62
<211> LENGTH: 71
<212> TYPE: PRT
<213> ORGANISM: Proteus mirabilis

<400> SEQUENCE: 62

Leu Arg Leu Leu Thr Pro Lys His Phe Asn Phe Val Phe Arg Ile Gly
1               5                   10                  15

Leu Thr Ile Ala Lys Lys Asn Val Lys Arg Ala His Glu Arg Asn Arg
            20                  25                  30

Ile Lys Arg Leu Ala Arg Glu Tyr Phe Arg Leu His Gln His Gln Leu
        35                  40                  45

Asp Phe Val Val Leu Val Arg Lys Gly Val Ala Glu Leu Asp Asn His
    50                  55                  60

Gln Leu Thr Glu Val Leu Gly
65                  70

<210> SEQ ID NO 63
<211> LENGTH: 71
<212> TYPE: PRT
<213> ORGANISM: Haemophilus influenzae

<400> SEQUENCE: 63

Leu Arg Leu Leu Thr Pro Ile Gln Phe Lys Asn Val Phe Arg Leu Gly
1               5                   10                  15

Leu Thr Val Ala Lys Lys His Leu Lys Arg Ala His Glu Arg Asn Arg
            20                  25                  30

Ile Lys Arg Leu Val Arg Glu Ser Phe Arg Leu Ser Gln His Arg Leu
        35                  40                  45

Asp Phe Val Phe Val Ala Lys Asn Gly Ile Gly Lys Leu Asp Asn Asn
    50                  55                  60

Thr Phe Ala Gln Ile Leu Glu
65                  70

<210> SEQ ID NO 64
<211> LENGTH: 71
<212> TYPE: PRT
<213> ORGANISM: Pseudomonas putida

<400> SEQUENCE: 64

Lys Asn Leu Leu Thr Pro Arg His Phe Lys Ala Val Phe Arg Leu Gly
1               5                   10                  15

```
Leu Val Ile Gly Lys Lys Ser Val Lys Leu Ala Val Gln Arg Asn Arg
            20                  25                  30

Leu Lys Arg Leu Met Arg Asp Ser Phe Arg Leu Asn Gln Gln Leu Leu
        35                  40                  45

Asp Ile Val Ile Val Ala Arg Lys Gly Leu Gly Glu Ile Glu Asn Pro
    50                  55                  60

Glu Leu His Gln His Phe Gly
65                  70
```

<210> SEQ ID NO 65
<211> LENGTH: 71
<212> TYPE: PRT
<213> ORGANISM: Buchnera aphidicola

<400> SEQUENCE: 65

```
Ser Lys Leu Leu Lys Ser Thr Asn Phe Gln Tyr Val Phe Arg Leu Gly
1               5                   10                  15

Leu Ser Ile Ser Arg Lys Asn Ile Lys His Ala Tyr Arg Arg Asn Lys
            20                  25                  30

Ile Lys Arg Leu Ile Arg Glu Thr Phe Arg Leu Leu Gln His Arg Leu
        35                  40                  45

Asp Phe Val Val Ile Ala Lys Lys Asn Ile Val Tyr Leu Asn Asn Lys
    50                  55                  60

Lys Ile Val Asn Ile Leu Glu
65                  70
```

<210> SEQ ID NO 66
<211> LENGTH: 71
<212> TYPE: PRT
<213> ORGANISM: Salmonella typhi
<220> FEATURE:
<221> NAME/KEY: VARIANT
<222> LOCATION: 31
<223> OTHER INFORMATION: Xaa = Any Amino Acid.

<400> SEQUENCE: 66

```
Leu Arg Leu Leu Thr Pro Ala His Phe Thr Phe Val Phe Arg Ile Gly
1               5                   10                  15

Leu Thr Val Ala Lys Lys Asn Val Arg Arg Ala His Glu Arg Xaa Arg
            20                  25                  30

Ile Lys Arg Leu Thr Arg Glu Ser Phe Arg Leu Arg Gln His Glu Leu
        35                  40                  45

Asp Phe Val Val Ala Lys Lys Gly Val Ala Asp Leu Asp Asn Arg
    50                  55                  60

Ala Leu Ser Glu Ala Leu Glu
65                  70
```

<210> SEQ ID NO 67
<211> LENGTH: 71
<212> TYPE: PRT
<213> ORGANISM: Yersinia pestis

<400> SEQUENCE: 67

```
Leu Arg Leu Leu Thr Pro Ser His Phe

```
Asp Phe Val Val Leu Val Lys Lys Gly Val Ala Asp Leu Asp Asn Arg
    50                  55                  60

Ala Leu Thr Glu Ala Leu Glu
65                  70

<210> SEQ ID NO 68
<211> LENGTH: 71
<212> TYPE: PRT
<213> ORGANISM: Klebsiella pneumoniae

<400> SEQUENCE: 68

Leu Arg Leu Leu Thr Pro Ser His Phe Thr Phe Val Phe Arg Ile Gly
 1               5                  10                  15

Leu Thr Val Ala Lys Lys Asn Val Lys Arg Ala His Glu Arg Asn Arg
            20                  25                  30

Ile Lys Arg Leu Thr Arg Glu Ser Phe Arg Leu Arg Gln His Glu Leu
        35                  40                  45

Asp Phe Val Val Ala Lys Arg Gly Val Ala Asp Leu Asp Asn Arg
    50                  55                  60

Ala Leu Ser Glu Ala Leu Glu
65                  70

<210> SEQ ID NO 69
<211> LENGTH: 66
<212> TYPE: PRT
<213> ORGANISM: Salmonella paratyphi

<400> SEQUENCE: 69

Ile Arg Leu Pro Ala Thr Ser Thr Arg Ile Gly Leu Thr Val Ala Lys
 1               5                  10                  15

Lys Asn Val Arg Arg Ala His Glu Arg Asn Arg Ile Lys Arg Leu Thr
            20                  25                  30

Arg Glu Ser Phe Arg Leu Arg Gln His Glu Leu Asp Phe Val Val Val
        35                  40                  45

Ala Lys Lys Gly Val Ala Asp Leu Asp Asn Arg Ala Leu Ser Glu Ala
    50                  55                  60

Leu Glu
65

<210> SEQ ID NO 70
<211> LENGTH: 71
<212> TYPE: PRT
<213> ORGANISM: Vibrio cholerae

<400> SEQUENCE: 70

Leu Arg Leu Leu Thr Pro Glu His Tyr Gln Lys Val Phe Arg Leu Gly
 1               5                  10                  15

Leu Ala Val Pro Lys Lys Gln Ile Lys Thr Ala Val Gly Arg Asn Arg
            20                  25                  30

Phe Lys Arg Ile Cys Arg Glu Ser Phe Arg Leu His Gln Asn Gln Leu
        35                  40                  45

Asp Phe Val Val Ile Ala Lys Lys Ser Ala Gln Asp Leu Ser Asn Glu
    50                  55                  60

Glu Leu Phe Asn Leu Leu Gly
65                  70

<210> SEQ ID NO 71
<211> LENGTH: 71
```

-continued

<212> TYPE: PRT
<213> ORGANISM: Pseudomonas aeruginosa

<400> SEQUENCE: 71

```
Lys Arg Leu Leu Thr Ala Arg Gln Phe Ser Ala Val Phe Arg Leu Gly
 1               5                  10                  15

Leu Val Ile Gly Lys Lys Asn Val Lys Leu Ala Val Gln Arg Asn Arg
            20                  25                  30

Leu Lys Arg Leu Ile Arg Glu Ser Phe Arg His Asn Gln Glu Thr Leu
        35                  40                  45

Asp Ile Val Val Ile Ala Arg Lys Gly Leu Gly Glu Leu Glu Asn Pro
    50                  55                  60

Glu Leu His Gln Gln Phe Gly
65                  70
```

<210> SEQ ID NO 72
<211> LENGTH: 71
<212> TYPE: PRT
<213> ORGANISM: Shewanella putrefaciens

<400> SEQUENCE: 72

```
Leu Arg Leu Leu Thr Pro Ala Gln Phe Lys Ser Val Phe Arg Leu Gly
 1               5                  10                  15

Leu Thr Val Ala Lys Arg Tyr Val Lys Arg Ala Asn Gln Arg Asn Arg
            20                  25                  30

Ile Lys Arg Val Ile Arg Asp Ser Phe Arg Leu Asn Gln His Asn Ile
        35                  40                  45

Asp Ile Val Val Leu Val Arg Asn Gly Val Met Glu Met Glu Asn Ala
    50                  55                  60

Glu Leu Asn Gly Leu Ile Glu
65                  70
```

<210> SEQ ID NO 73
<211> LENGTH: 71
<212> TYPE: PRT
<213> ORGANISM: Coxiella burnetii

<400> SEQUENCE: 73

```
Trp Arg Ile Arg Thr Thr Ala Glu Phe Arg Arg Ile Tyr Arg Leu Gly
 1               5                  10                  15

Val Val Ala Ser Lys Arg Asn Val Arg Lys Ala Val Trp Arg Asn Arg
            20                  25                  30

Val Arg Arg Val Val Lys Glu Ala Phe Arg Ile Arg Lys Lys Asp Leu
        35                  40                  45

Asp Ile Val Val Val Ala Lys Ala Ser Ser Val Glu Ala Asp Asn Lys
    50                  55                  60

Glu Leu Tyr Glu Cys Ile Asn
65                  70
```

<210> SEQ ID NO 74
<211> LENGTH: 70
<212> TYPE: PRT
<213> ORGANISM: Rickettsia prowazekii

<400> SEQUENCE: 74

```
Thr Ser Leu Lys Asn Gln Lys Glu Phe Glu Leu Ile Asn Leu Gly Ile
 1               5                  10                  15

Lys Val Ser Arg Lys Leu Asn Lys Lys Ala Val Val Arg Asn Lys Ile
            20                  25                  30

```
Lys Arg Arg Ile Arg His Leu Met Arg Ile Ile Val Asn Asp Ser Ala
            35                  40                  45

Ile Ile Ile Ile Pro Lys Lys Gly Phe Glu Ile Asn Phe Ser His
    50                  55                  60

Leu Gln Tyr Glu Leu Ser
65                  70

<210> SEQ ID NO 75
<211> LENGTH: 73
<212> TYPE: PRT
<213> ORGANISM: Caulobacter crescentus

<400> SEQUENCE: 75

Glu Arg Leu Arg Lys Arg Pro Asp Phe Leu Leu Ala Ala Arg Val Gly
1               5                   10                  15

Phe Thr Ala Thr Lys Lys Ile Gly Gly Ala Val Glu Arg Asn Arg Ala
            20                  25                  30

Lys Arg Arg Leu Arg Glu Ala Ala Arg Leu Val Leu Pro Leu Asp Tyr
            35                  40                  45

Val Phe Ile Ala Arg Gly Gly Thr Gly Thr Arg Glu Trp Ala Arg Leu
    50                  55                  60

Leu Asp Asp Val Lys Thr Ala Leu Ile
65                  70

<210> SEQ ID NO 76
<211> LENGTH: 74
<212> TYPE: PRT
<213> ORGANISM: Helicobacter pylori 26695

<400> SEQUENCE: 76

Asp Ser Leu Lys Asn Lys Ser Glu Phe Asp Arg Val Tyr Lys Leu Gly
1               5                   10                  15

Leu Ser Val Ser Lys Lys Val Gly Asn Ala Val Lys Arg Asn Leu Ile
            20                  25                  30

Lys Arg Arg Leu Arg Ser Leu Thr Leu Lys His Ala Ala Leu Cys Ala
            35                  40                  45

Leu Val Phe Val Pro Arg Ser Asp Cys Tyr His Leu Asp Phe Trp Ala
    50                  55                  60

Leu Glu Lys His Phe Leu Glu Met Leu Thr
65                  70

<210> SEQ ID NO 77
<211> LENGTH: 74
<212> TYPE: PRT
<213> ORGANISM: Helicobacter pylori J99

<400> SEQUENCE: 77

Asp Ser Leu Lys Asn Lys Ser Glu Phe Asp Arg Val Tyr Lys Leu Gly
1               5                   10                  15

Leu Ser Val Ser Lys Lys Val Gly Asn Ala Val Lys Arg Asn Leu Ile
            20                  25                  30

Lys Arg Arg Leu Arg Ser Leu Val Thr Arg His Ala Ala Leu Cys Ala
            35                  40                  45

Leu Val Phe Val Pro Arg Ser Asp Cys Tyr His Leu Asp Phe Trp Ala
    50                  55                  60

Leu Glu Lys His Phe Leu Glu Met Leu Thr
65                  70
```

<210> SEQ ID NO 78
<211> LENGTH: 74
<212> TYPE: PRT
<213> ORGANISM: Camphylobacter jejuni

<400> SEQUENCE: 78

Asp Lys Phe Ser Thr Asn Glu Glu Phe Ser Val Tyr Lys Ile Ala
1               5                   10                  15

Val Val Ala Ser Lys Lys Val Gly Lys Ala Val Val Arg Asn Arg Ser
            20                  25                  30

Lys Arg Ile Leu Arg Ala Leu Phe Ala Lys Phe Glu Arg Tyr Leu Lys
        35                  40                  45

Tyr Ile Phe Val Ala Lys Asn Glu Ile Thr Glu Leu Ser Phe Ser Arg
    50                  55                  60

Leu Glu Lys Asn Leu Lys Trp Gly Leu Lys
65                  70

<210> SEQ ID NO 79
<211> LENGTH: 71
<212> TYPE: PRT
<213> ORGANISM: Neisseria gonorrhoeae

<400> SEQUENCE: 79

Tyr Arg Leu Leu Lys Thr Asp Asp Phe Ser Ser Val Phe Arg Ile Gly
1               5                   10                  15

Leu Val Val Gly Lys Lys Thr Ala Lys Arg Ala Asn Glu Arg Asn Tyr
            20                  25                  30

Met Lys Arg Val Ile Arg Asp Trp Phe Arg Leu Asn Lys Asn Arg Leu
        35                  40                  45

Asp Phe Val Val Arg Val Arg Arg Lys Phe Asp Arg Ala Thr Ala Lys
    50                  55                  60

Gln Ala Arg Ala Glu Leu Ala
65                  70

<210> SEQ ID NO 80
<211> LENGTH: 71
<212> TYPE: PRT
<213> ORGANISM: Neisseria meningitidis

<400> SEQUENCE: 80

Tyr Arg Leu Leu Lys Thr Asp Asp Phe Ser Ser Val Phe Arg Ile Gly
1               5                   10                  15

Leu Val Val Gly Glu Lys Thr Ala Lys Arg Ala Asn Glu Arg Asn Tyr
            20                  25                  30

Met Lys Arg Val Ile Arg Asp Trp Phe Arg Leu Asn Lys Asn Arg Leu
        35                  40                  45

Asp Phe Val Val Arg Val Arg Arg Lys Phe Asp Arg Ala Thr Ala Lys
    50                  55                  60

Gln Ala Arg Ala Glu Leu Ala
65                  70

<210> SEQ ID NO 81
<211> LENGTH: 75
<212> TYPE: PRT
<213> ORGANISM: Bordetella pertussis

<400> SEQUENCE: 81

Ala Arg Leu His Arg Pro Ser Glu Phe Ala Ala Ala Leu Arg Leu Gly
1               5                   10

Leu Val Ile Ala Lys Arg Phe Ala Arg Ala Val Thr Arg Asn Thr
            20                  25                  30

Leu Lys Arg Val Ile Arg Glu Ala Phe Arg Ala Arg Leu Ala Leu
        35                  40                  45

Asp Tyr Val Val Arg Leu His Ser Lys Leu Thr Pro Ala Ser Leu Thr
    50                  55                  60

Ala Leu Lys Arg Ser Ala Arg Ala Glu Val Asp
65                  70                  75

<210> SEQ ID NO 82
<211> LENGTH: 70
<212> TYPE: PRT
<213> ORGANISM: Thiobacillus ferooxidans

<400> SEQUENCE: 82

Asp Arg Leu Arg Gln Lys Val Ala Ile Gln Arg Thr Leu Arg Leu Gly
1               5                   10                  15

Leu Ala Val Ser Arg Lys Val Gly Asn Ala Val Arg Asn Arg Ile
            20                  25                  30

Lys Arg Arg Leu Arg Glu Ala Phe Arg Gln Gln Ser Val Arg Thr Asp
        35                  40                  45

Val Leu Val Val Ala Arg Pro Ser Ala Arg Gln Leu Ser Met Arg Ala
    50                  55                  60

Met Gly Ala Tyr Leu Gln
65                  70

<210> SEQ ID NO 83
<211> LENGTH: 70
<212> TYPE: PRT
<213> ORGANISM: Streptomyces bikiniensis

<400> SEQUENCE: 83

Asn Arg Leu Arg Arg Arg Glu Asp Phe Ala Thr Ala Val Arg Ala Gly
1               5                   10                  15

Phe Val Val Ser Lys Ala Val Gly Gly Ala Val Val Arg Asn Gln Val
            20                  25                  30

Lys Arg Arg Leu Lys His Leu Val Cys Asp Arg Leu Ser Ala Leu Leu
        35                  40                  45

Val Val Val Arg Ala Leu Pro Gly Ala Gly Asp Ala Asp His Ala Gln
    50                  55                  60

Leu Ala Arg Asp Leu Asp
65                  70

<210> SEQ ID NO 84
<211> LENGTH: 70
<212> TYPE: PRT
<213> ORGANISM: Streptomyces coelicolor

<400> SEQUENCE: 84

Asn Arg Leu Arg Arg Arg Glu Asp Phe Ala Thr Ala Val Arg Ala Gly
1               5                   10                  15

Phe Val Val Ser Lys Ala Val Gly Val Ala Val Val Arg Asn Lys Val
            20                  25                  30

Lys Arg Arg Leu Arg His Leu Met Arg Asp Arg Ile Asp Leu Leu Leu
        35                  40                  45

Val Val Val Arg Ala Leu Pro Gly Ala Gly Asp Ala Asp His Ala Gln
    50                  55                  60

```
Leu Ala Arg Asp Leu Asp
 65                  70

<210> SEQ ID NO 85
<211> LENGTH: 74
<212> TYPE: PRT
<213> ORGANISM: Micrococcus luteus

<400> SEQUENCE: 85

Arg Arg Val Arg Thr Pro Ala Glu Phe Arg His Leu Gly Arg Ala Gly
 1               5                  10                  15

Phe Val Val Ser Lys Ala Val Gly Asn Ala Val Thr Arg Asn Arg Val
            20                  25                  30

Lys Arg Arg Leu Arg Ala Val Val Ala Glu Gln Met Arg Leu Val Leu
        35                  40                  45

Val Gln Val Arg Ala Leu Pro Ala Ala Glu Ala Asp Tyr Ala Leu
    50                  55                  60

Leu Arg Arg Glu Thr Val Gly Ala Leu Gly
 65                  70

<210> SEQ ID NO 86
<211> LENGTH: 71
<212> TYPE: PRT
<213> ORGANISM: Mycobacterium tuberculosis

<400> SEQUENCE: 86

Asn Arg Met Arg Arg Ser Ala Asp Phe Glu Thr Thr Val Arg Val Gly
 1               5                  10                  15

Leu Ile Ile Ala Lys Ser Val Gly Ser Ala Val Glu Arg His Arg Val
            20                  25                  30

Ala Arg Arg Leu Arg His Val Ala Gly Ser Ile Val Lys Glu Leu Asp
        35                  40                  45

His Val Val Ile Arg Ala Leu Pro Ser Ser Arg His Val Ser Ser Ala
    50                  55                  60

Arg Leu Glu Gln Gln Leu Arg
 65                  70

<210> SEQ ID NO 87
<211> LENGTH: 71
<212> TYPE: PRT
<213> ORGANISM: Mycobacterium leprae

<400> SEQUENCE: 87

Asn Arg Met Arg Arg Ser Ser Glu Phe Asp Ala Thr Val His Val Gly
 1               5                  10                  15

Leu Ile Ile Ala Lys Thr Val Gly Ser Ala Val Glu Arg His Arg Val
            20                  25                  30

Ala Arg Arg Leu Arg His Val Ala Arg Thr Met Leu Gly Glu Leu Asp
        35                  40                  45

Gln Val Val Ile Arg Ala Leu Pro Ser Ser Arg Asn Val Ser Ser Ala
    50                  55                  60

Trp Leu Ala Gln Gln Leu Arg
 65                  70

<210> SEQ ID NO 88
<211> LENGTH: 71
<212> TYPE: PRT
<213> ORGANISM: Mycobacterium bovis

<400> SEQUENCE: 88
```

```
Asn Arg Met Arg Arg Ser Ala Asp Phe Glu Thr Thr Val Arg Val Gly
  1               5                  10                 15

Leu Ile Ile Ala Lys Ser Val Gly Ser Ala Val Glu Arg His Arg Val
             20                  25                 30

Ala Arg Arg Leu Arg His Val Ala Gly Ser Ile Val Lys Glu Leu Asp
         35                  40                  45

His Val Val Ile Arg Ala Leu Pro Ser Ser Arg His Val Ser Ser Ala
     50                  55                  60

Arg Leu Glu Gln Gln Leu Arg
 65                  70

<210> SEQ ID NO 89
<211> LENGTH: 71
<212> TYPE: PRT
<213> ORGANISM: Mycobacterium avium

<400> SEQUENCE: 89

Asn Arg Met Thr Arg Ser Thr Glu Phe Asp Ala Thr Val Arg Val Gly
  1               5                  10                 15

Leu Val Val Gly Lys Ala Val Gly Thr Ala Val Gln Arg His Arg Val
             20                  25                 30

Ala Arg Arg Leu Arg His Val Ala Arg Ala Leu Leu Gly Glu Leu Asp
         35                  40                  45

Arg Leu Val Ile Arg Ala Leu Pro Gly Ser Arg Thr Ala Ser Ser Ala
     50                  55                  60

Arg Leu Ala Gln Glu Leu Gln
 65                  70

<210> SEQ ID NO 90
<211> LENGTH: 50
<212> TYPE: PRT
<213> ORGANISM: Corynebacterium diphtheriae

<400> SEQUENCE: 90

His Lys Leu Ser Gln Phe Arg Ala Thr Ile Arg Phe Gly Leu Val Val
  1               5                  10                 15

Ser Lys Ala Val Gly Asn Ala Val Thr Arg His Arg Val Ser Arg Gln
             20                  25                 30

Leu Arg His Phe His Val Val Glu Leu Arg Ala Asp Val Gln Ala Ala
         35                  40                  45

Leu Asp
    50

<210> SEQ ID NO 91
<211> LENGTH: 3
<212> TYPE: PRT
<213> ORGANISM: Artificial Sequence
<220> FEATURE:
<223> OTHER INFORMATION: Synthetic

<400> SEQUENCE: 91

Lys Asn Glu
 1

<210> SEQ ID NO 92
<211> LENGTH: 70
<212> TYPE: PRT
<213> ORGANISM: Bacillus subtilis

<400> SEQUENCE: 92
```

```
Asn Arg Leu Lys Arg Ser Asp Asp Phe Arg Lys Val Phe Arg Val Gly
 1               5                  10                 15

Leu Ser Val Ser Lys Lys Ile Gly Asn Ala Val Met Arg Asn Arg Ile
             20                  25                 30

Lys Arg Leu Ile Arg Gln Phe Phe Gln Glu His Glu Gln Ala Leu Asp
         35                  40                 45

Tyr Ile Ile Ile Ala Arg Lys Pro Ala Ala Asp Met Thr Tyr Glu Glu
     50                  55                 60

Thr Lys Lys Ser Leu Gln
 65              70
```

<210> SEQ ID NO 93
<211> LENGTH: 69
<212> TYPE: PRT
<213> ORGANISM: Bacillus halodurans

<400> SEQUENCE: 93

```
His Arg Ile Lys Lys Asn Asp Glu Phe Ser Arg Val Phe Arg Val Leu
 1               5                  10                 15

Ser Val Ser Lys Lys Ile Gly Asn Ala Val Thr Arg Asn Arg Val Lys
             20                  25                 30

Arg Leu Ile Arg Thr Ser Ile Thr Glu Leu Lys Asp Glu Ile Asp Tyr
         35                  40                 45

Val Ile Ile Ala Arg Lys Pro Cys Ala Glu Met Thr Tyr Glu Gln Val
     50                  55                 60

Lys Gly Ser Leu Trp
 65
```

<210> SEQ ID NO 94
<211> LENGTH: 70
<212> TYPE: PRT
<213> ORGANISM: Bacillus anthracis

<400> SEQUENCE: 94

```
His Arg Ile Lys Lys Asn Phe Glu Phe Gln Thr Val Phe Arg Ile Gly
 1               5                  10                 15

Leu Ser Val Ser Lys Lys Ile Gly Asn Ala Val Val Arg Asn Arg Ile
             20                  25                 30

Lys Arg Met Ile Arg Gln Ile Leu Lys Gln Asn Ile Ser Glu Ile Asp
         35                  40                 45

Phe Val Ile Leu Val Arg Lys Ser Val Leu Glu Leu Lys Tyr Ala Glu
     50                  55                 60

Leu Lys Lys Ser Leu Ile
 65              70
```

<210> SEQ ID NO 95
<211> LENGTH: 70
<212> TYPE: PRT
<213> ORGANISM: Mycoplasma capricolum

<400> SEQUENCE: 95

```
Arg Val Ile Lys Asp Arg Lys Glu Phe Gln Glu Ile Ile Lys Tyr Gly
 1               5                  10                 15

Ile Ser Val Gly Lys Lys Ile Gly Asn Ala Val Ile Arg Asn Lys Val
             20                  25                 30

Lys Arg Gln Ile Arg Met Ile Met Arg Glu Gln Phe Cys Asn Ile Asp
         35                  40                 45
```

```
Ile Ile Ile Ile Ile Asn Gln Gly Phe Leu Glu Leu Thr Phe Lys Thr
 50                  55                  60

Leu Ser Lys Leu Leu Ile
 65              70

<210> SEQ ID NO 96
<211> LENGTH: 71
<212> TYPE: PRT
<213> ORGANISM: Mycoplasma pneumoniae

<400> SEQUENCE: 96

His His Leu Arg Glu Arg Lys Val Phe Ala Ala Leu Leu Arg Ala Ala
 1               5                  10                  15

Val Ser Ile Ser Lys Thr Lys Tyr Lys Leu Ala Val Glu Arg Asn Leu
             20                  25                  30

Ile Arg Arg Gln Val Lys Ala Ile Phe Gln Gln Ile Ser Asn Asn Leu
         35                  40                  45

Asp Val Leu Val Ile Val Asn Lys Gly Phe Ile Glu Leu Thr Phe Lys
     50                  55                  60

Glu Lys Gln Thr Ile Phe Leu
 65              70

<210> SEQ ID NO 97
<211> LENGTH: 71
<212> TYPE: PRT
<213> ORGANISM: Mycoplasma genitalium

<400> SEQUENCE: 97

His Ser Leu Arg Arg Glu Lys Val Phe Thr Thr Ile Leu Arg Val Ala
 1               5                  10                  15

Ile Ser Ile Ala Lys Thr Lys Tyr Lys Leu Ala Val Gln Arg Asn Leu
             20                  25                  30

Ile Lys Arg Gln Ile Arg Ser Val Ile Met Ala Leu Gly His Gln Leu
         35                  40                  45

Asp Ile Leu Val Ile Ala Arg Lys Gly Val Glu Ser Leu Glu Tyr Gln
     50                  55                  60

Glu Lys Gln Lys Leu Phe Leu
 65              70

<210> SEQ ID NO 98
<211> LENGTH: 68
<212> TYPE: PRT
<213> ORGANISM: Streptococcus pyogenes

<400> SEQUENCE: 98

Val Lys Ser Asp Lys Asp Phe Gln Ala Ile Phe Arg Val Gly Ile Ser
 1               5                  10                  15

Val Gly Lys Lys Ile Gly Asn Ala Val Thr Arg Asn Ala Val Lys Arg
             20                  25                  30

Lys Ile Arg His Val Leu Met Glu Leu Gly Pro Tyr Leu Asp Phe Val
         35                  40                  45

Val Ile Ala Arg Lys Gly Val Glu Glu Leu Asp Tyr Ser Glu Leu Gln
     50                  55                  60

Gln Asn Leu His
 65

<210> SEQ ID NO 99
<211> LENGTH: 70
<212> TYPE: PRT
```

```
<213> ORGANISM: Streptococcus mutans

<400> SEQUENCE: 99

Tyr Arg Val Lys Arg Glu Lys Asp Phe Gln Ala Ile Phe Arg Val Gly
  1               5                  10                  15

Leu Ser Val Gly Lys Arg Leu Gly Asn Ala Val Val Arg Asn Ala Ile
             20                  25                  30

Lys Arg Lys Leu Arg His Ile Ile Gln Asn Ala Lys Gly Ser Leu Asp
         35                  40                  45

Phe Val Val Ile Ala Arg Lys Gly Val Glu Thr Leu Gly Tyr Ala Thr
     50                  55                  60

Met Lys Lys Asn Leu Val
 65                  70

<210> SEQ ID NO 100
<211> LENGTH: 70
<212> TYPE: PRT
<213> ORGANISM: Streptococcus pneumoniae

<400> SEQUENCE: 100

Phe Arg Val Lys Lys Asn Ala Asp Phe Lys Ala Ile Phe Arg Val Gly
  1               5                  10                  15

Leu Ser Val Ser Lys Lys Leu Gly Asn Ala Val Thr Arg Asn Gln Ile
             20                  25                  30

Lys Arg Arg Ile Arg His Asn Phe Lys Val His Lys Ser His Leu Asp
         35                  40                  45

Phe Val Val Ile Ala Arg Gln Pro Ala Lys Asp Met Thr Thr Leu Glu
     50                  55                  60

Met Glu Lys Asn Leu Leu
 65                  70

<210> SEQ ID NO 101
<211> LENGTH: 70
<212> TYPE: PRT
<213> ORGANISM: Staphylococcus aureus NCTC

<400> SEQUENCE: 101

Tyr Arg Ile Lys Lys Asn Ala Asp Phe Gln Arg Ile Tyr Arg Leu Gly
  1               5                  10                  15

Ile Ser Val Ser Lys Lys Leu Gly Asn Ala Val Leu Arg Asn Lys Ile
             20                  25                  30

Lys Arg Ala Ile Arg Glu Asn Phe Lys Val His Lys Ser His Ile Asp
         35                  40                  45

Ile Ile Val Ile Ala Arg Gln Pro Ala Lys Asp Met Thr Thr Leu Gln
     50                  55                  60

Ile Gln Asn Ser Leu Glu
 65                  70

<210> SEQ ID NO 102
<211> LENGTH: 70
<212> TYPE: PRT
<213> ORGANISM: Staphylococus aureus COL

<400> SEQUENCE: 102

Tyr Arg Ile Lys Lys Asp Ser Asp Phe Gln Arg Ile Tyr Arg Leu Gly
  1               5                  10                  15

Ile Ser Val Ser Lys Lys Leu Gly Asn Ala Val Leu Arg Asn Lys Ile
             20                  25                  30
```

```
Lys Arg Ala Ile Arg Glu Ala Tyr Arg Leu Asn Ile Asp Glu Lys Ile
            35                  40                  45

Asp Ile Ile Val Ile Ala Arg Val Ser Ser Lys Asp Ile Asp Lys Gln
 50                  55                  60

Ile Gln Asn Ser Leu Glu
 65                  70

<210> SEQ ID NO 103
<211> LENGTH: 70
<212> TYPE: PRT
<213> ORGANISM: Clostridium difficile

<400> SEQUENCE: 103

Lys Gly Leu Lys Asn Ser Glu Asp Phe Arg Lys Val Tyr Arg Val Gly
 1               5                  10                  15

Ile Ser Val Ser Lys Lys Val Gly Lys Ala Ile Thr Arg Asn Arg Val
            20                  25                  30

Arg Arg Leu Ile Lys Glu Val Val Ile Ala Met Lys Asp Gln Ile Asp
            35                  40                  45

Ile Val Phe Val Arg Ala Ile Pro Pro Ala Ala Thr Ala Ser Tyr Glu
 50                  55                  60

Ser Ile Lys Asn Leu Val
 65                  70

<210> SEQ ID NO 104
<211> LENGTH: 71
<212> TYPE: PRT
<213> ORGANISM: Synechocystis PCC6803

<400> SEQUENCE: 104

Leu Arg Leu Lys His Trp Gln Asp Phe Gln Thr Val Tyr Arg Phe Gly
 1               5                  10                  15

Ile Thr Val Ser Gln Lys Val Ser Lys Lys Ala Thr Val Arg Asn Arg
            20                  25                  30

Leu Lys Arg Gln Ile Arg Ala Val Ile Asn His Phe Gln Pro Gln Ile
            35                  40                  45

Asp Val Val Ile Ile Val Leu Pro Gln Gly Ile Gly Cys Asn Tyr Glu
 50                  55                  60

Arg Phe Leu Arg Glu Leu Glu
 65                  70

<210> SEQ ID NO 105
<211> LENGTH: 71
<212> TYPE: PRT
<213> ORGANISM: Pseudanabaena PCC6903

<400> SEQUENCE: 105

Asn Arg Leu Arg Arg Arg Glu Asp Phe Ala Lys Val Tyr Arg Ile Gly
 1               5                  10                  15

Ile Val Val Ser Lys Lys Val Ser Lys Leu Ala Val Thr Arg Asn Arg
            20                  25                  30

Phe Lys Arg Gln Leu Arg Ala Ile Phe Arg Gln Leu Leu Ser Gln Leu
            35                  40                  45

Gln Ile Val Val Thr Val Thr Thr Val Ala Ser Lys Pro Asn Tyr Gln
 50                  55                  60

Glu Leu Gly Asp Asp Leu Lys
 65                  70
```

```
<210> SEQ ID NO 106
<211> LENGTH: 70
<212> TYPE: PRT
<213> ORGANISM: Borrelia burgdorferi

<400> SEQUENCE: 106

Ile Ser Leu Lys Ser Lys Ile Glu Ile Gln Lys Ile Phe Arg Ile Leu
1               5                   10                  15
Val Thr Phe Ser Lys Gly Phe Arg Gly Ser Val Lys Arg Asn Arg Ile
            20                  25                  30
Arg Arg Leu Phe Lys Glu Ala Phe Arg Lys Arg Leu Glu Leu Leu Asp
        35                  40                  45
Ile Ile Phe Val Val Ser Tyr Gly Lys Leu Thr Leu Thr Tyr Phe Ser
    50                  55                  60
Ile Glu Ser Leu Met Lys
65                  70

<210> SEQ ID NO 107
<211> LENGTH: 71
<212> TYPE: PRT
<213> ORGANISM: Treponema pallidum

<400> SEQUENCE: 107

Glu Arg Leu Arg Gly Ser Cys Arg Val Arg Ala Val Phe Arg Phe Leu
1               5                   10                  15

Ala Thr Phe Arg Arg Gly Tyr Gly Lys Ala Val Ala Arg Asn Arg Ala
            20                  25                  30

Arg Arg Leu Ser Lys Glu Ala Tyr Arg Ala Leu Lys Ser Ser Leu Asp
        35                  40                  45

Leu Val Leu Leu Val Ser Val Val Glu Asp Ser Leu Ala Ala Tyr Gln
    50                  55                  60

Arg Leu Leu Cys Val Leu Cys
65                  70

<210> SEQ ID NO 108
<211> LENGTH: 73
<212> TYPE: PRT
<213> ORGANISM: Chlamydia trachomatis

<400> SEQUENCE: 108

Ala Arg Leu Leu Lys Arg Lys Gln Phe Val Tyr Val Gln Lys Val Gly
1               5                   10                  15

Ile Thr Val Ser Lys Lys Phe Gly Lys Ala His Gln Arg Asn Arg Phe
            20                  25                  30

Lys Arg Ile Val Arg Glu Ala Phe Arg His Val Arg Pro Asn Leu Gln
        35                  40                  45

Val Val Ile Ser Pro Arg Gly Asn Ser Gln Pro Asp Phe Leu Lys Leu
    50                  55                  60

Ser Glu Glu Leu Leu Gln Arg Ile Pro
65                  70

<210> SEQ ID NO 109
<211> LENGTH: 73
<212> TYPE: PRT
<213> ORGANISM: Chlamydia trachomatis MoPn

<400> SEQUENCE: 109

Ala Arg Leu Leu Lys Arg Lys Gln Phe Val Tyr Val Gln Lys Val Gly
1               5                   10                  15

Val Thr Val Ser Lys Lys Phe Gly Lys Ala His Gln Arg Asn Arg Phe
            20                  25                  30

Lys Arg Ile Val Arg Glu Ala Phe Arg His Val Arg Pro Asn Leu Gln
```

```
                35                  40                  45
Val Val Val Ser Pro Lys Gly Gly Thr Leu Pro Asn Phe Gly Lys Leu
        50                  55                  60

Ser Ala Asp Leu Leu Lys His Ile Pro
65                  70

<210> SEQ ID NO 110
<211> LENGTH: 74
<212> TYPE: PRT
<213> ORGANISM: Chlamydia pneumoniae

<400> SEQUENCE: 110

Ser Arg Val Leu Lys Arg Lys Gln Phe Leu Tyr Ile Thr Arg Met Gly
1               5                   10                  15

Ile Thr Val Ser Lys Lys Phe Gly Lys Ala His Glu Arg Asn Ser Phe
                20                  25                  30

Lys Arg Val Val Arg Glu Val Phe Arg His Val Arg His Gln Leu Gln
            35                  40                  45

Ile Val Val Phe Pro Lys Gly His Lys Gln Arg Pro Val Phe Ser Lys
        50                  55                  60

Leu Leu Gln Asp Phe Ile Asn Gln Ile Pro
65                  70

<210> SEQ ID NO 111
<211> LENGTH: 74
<212> TYPE: PRT
<213> ORGANISM: Thermotoga maritima

<400> SEQUENCE: 111

Glu Arg Leu Arg Leu Arg Arg Asp Phe Leu Leu Ile Phe Arg Leu Gly
1               5                   10                  15

Ile Val Val Lys Arg Lys Phe Gly Lys Ala Thr Arg Arg Asn Lys Leu
                20                  25                  30

Lys Arg Trp Val Arg Glu Ile Phe Arg Arg Asn Lys Gly Val Ile Asp
            35                  40                  45

Ile Val Val Ile Pro Arg Lys Lys Leu Ser Glu Glu Phe Glu Arg Val
        50                  55                  60

Asp Phe Trp Thr Val Arg Glu Lys Leu Leu
65                  70

<210> SEQ ID NO 112
<211> LENGTH: 78
<212> TYPE: PRT
<213> ORGANISM: Porphyromonas gingivalis

<400> SEQUENCE: 112

Glu Arg Leu Tyr Leu Arg Asp Glu Ile Asn Thr Val Phe Ser Met Leu
1               5                   10                  15

Val Ser Val Ala Lys Lys Arg Phe Arg Arg Ala Val Lys Arg Asn Arg
                20                  25                  30

Val Arg Arg Leu Val Arg Glu Ala Tyr Arg Leu Asn Lys His Leu Leu
            35                  40                  45

Asp Val Leu Gln Glu Arg Gln Ile Tyr Ala Thr Ile Ala Phe Met Val
        50                  55                  60

Val Ser Asp Glu Leu Pro Asp Phe Arg Thr Val Glu Arg Ala
65                  70                  75

<210> SEQ ID NO 113
```

```
<211> LENGTH: 77
<212> TYPE: PRT
<213> ORGANISM: Deinococcus radiodurans

<400> SEQUENCE: 113

Leu Arg Gly Glu Arg Glu Phe Arg Lys Val Arg Arg Ile Gly Leu Val
  1               5                  10                  15

Val Ser Lys Lys Thr Leu Lys His Ala Val Lys Arg Asn Arg Ala Arg
             20                  25                  30

Arg Arg Val Arg Glu Ala Leu Arg Thr Met Pro Pro Glu Leu Arg Ala
         35                  40                  45

Ile Leu Met Leu Asn Pro Gly Val Leu Thr Val Pro Phe Pro Glu Leu
     50                  55                  60

Gln Ala Ala Leu Ala Gln Ala Leu Gln Arg Gly Ala Gly
 65                  70                  75

<210> SEQ ID NO 114
<211> LENGTH: 75
<212> TYPE: PRT
<213> ORGANISM: Chlorobium tepidum

<400> SEQUENCE: 114

Ala Arg Leu Lys Gly Gly Phe Leu Leu Leu Ile Arg Val Leu Phe Thr
  1               5                  10                  15

Val Gly Lys Lys Leu Val Pro Arg Ala Val Asp Arg Asn Arg Ile Lys
             20                  25                  30

Arg Leu Met Arg Glu Ala Tyr Arg Leu Glu Lys Asn Ile Leu Asp His
         35                  40                  45

Gln Val Met Leu Ala Phe Leu Tyr Arg Ala Arg Ala Asp Ala Ile Pro
     50                  55                  60

Ser Leu Glu Arg Phe Arg Ala Ile Arg His Met
 65                  70                  75
```

INHIBITORS OF RNASE P PROTEINS AS ANTIBACTERIAL COMPOUNDS

CROSS-REFERENCE TO RELATED APPLICATIONS

This application claims benefit of priority from U.S. Provisional Application No. 60/323,853, filed Sep. 21, 2001, hereby incorporated by reference.

BACKGROUND OF THE INVENTION

This invention relates to inhibitors of bacterial ribonuclease P holoenzymes. Such inhibitors are useful as antibacterial agents.

Ribonuclease P (RNase P) is an endoribonuclease that cleaves the 5'-terminal leader sequences of precursor tRNAs. RNase P has been characterized in a representative number of species.

In bacteria, the structure of the RNase P holoenzyme is composed of a catalytic RNA subunit (350–450 nucleotides; encoded by the rnp B gene) and a single protein subunit (110–160 amino acids; encoded by the rnp A gene); both are essential for in vivo activity. In *Escherichia coli* (*E. coli*), the RNA subunit is termed M1 and the protein subunit is C5. The C5 protein engages in specific interactions with the M1 RNA to stabilize certain M1 RNA conformations. Through these interactions with M1, C5 plays a critical role in the recognition/binding of some substrates.

Comparison of RNase P protein subunits between bacterial species reveals that their primary structures have only a moderate degree of identity. For example, the protein subunits of *Bacillus subtilis* (*B. subtilis*) and *E. coli* are 30% identical. The functional significance of some conserved amino acid residues has been confirmed by mutagenesis studies which have shown that these conserved amino acids play a significant role in the catalytic function of the RNase P holoenzyme.

The tertiary structure of the RNase P protein subunit expressed in *B. subtilis* has been determined by X-ray crystallography. The overall topology of α-helices and β-sheets is α1 β2 β3 α2 β4 α3, with an uncommon β3α2β4 cross-over connection that may confer specific functional consequences. Another functional aspect of the protein is the long loop connecting β2 to β3, termed the metal binding loop, which binds $Zn^{2+}$ ions and mediates interlattice contacts. In addition, the crystal structure reveals an overall fold that is similar to the ribosomal protein S5, translational elongation factor EF-G (domain IV), and DNA gyrase.

Many pathogens exist for which there are few effective treatments, and the number of strains resistant to available drugs is continually increasing. Thus, improved methods are needed for the treatment and prevention of infections caused by a number of bacteria. Desirably, these treatments kill pathogenic bacteria without harming the tissues of the infected patient.

SUMMARY OF THE INVENTION

The present invention features compounds useful for inhibiting RNase P activity. These compounds can be used as therapeutics for treating or preventing a variety of bacterial infections.

In one aspect, the invention features a compound having the chemical structure of formula I:

$$Y-(NR')_k-U_1-(NR'')_l-A-(NR^1)_m-U_2-(NR^2)_n-Z \quad I$$

or a derivative, salt, racemic mixture, mixture of E/Z isomers, or mixture of diastereomers thereof, wherein $U_1$ and $U_2$ are independently carbonyl, thiocarbonyl, or sulfonyl; k, l, m, and n are independently 0 or 1; A is a linker of 1, 2, 3, 4, 5, 6, 7, or 8 atoms that is optionally substituted with a group selected from alkyl, heteroalkyl, alkene, heteroalkene, alkyne, heteroalkyne, aryl, alkaryl, and heteroaryl; and R', R'', $R^1$, and $R^2$ are independently H, alkyl, heteroalkyl, alkene, heteroalkene, alkyne, heteroalkyne, aryl, or heteroaryl. In certain compounds of the invention, A is $-CH_2CH_2-$, and k and n are 0. In one embodiment, Y is a group of formulas II, III, IV, V, VI, VII, VIII, IX, or X; and Z is a substituted phenyl group or a group of formulas II, III, IV, V, VI, VII, VIII, IX, X, or XI, wherein said substituted phenyl group comprises hydroxy, alkoxy, aryloxy, sulfhydryl, alkylthio, arylthio, halogen, fluoroalkyl, carboxyl, carboxyalkyl, amino, aminoalkyl, monosubstituted amino, disubstituted amino, quaternary amino, nitro, alkyl, heteroalkyl, alkene, heteroalkene, alkyne, heteroalkyne, aryl, or heteroaryl. Y and Z may be groups of the same or different formulas. In another embodiment, when A is propylene or substituted phenylene, k and n are both 1, and l and m are both 0, Z and Y are not both formula II. Y may also be a group of formulas II, V, VI, VII, or VIII, or Y may be a group of formulas V, VI, VII, or VIII.

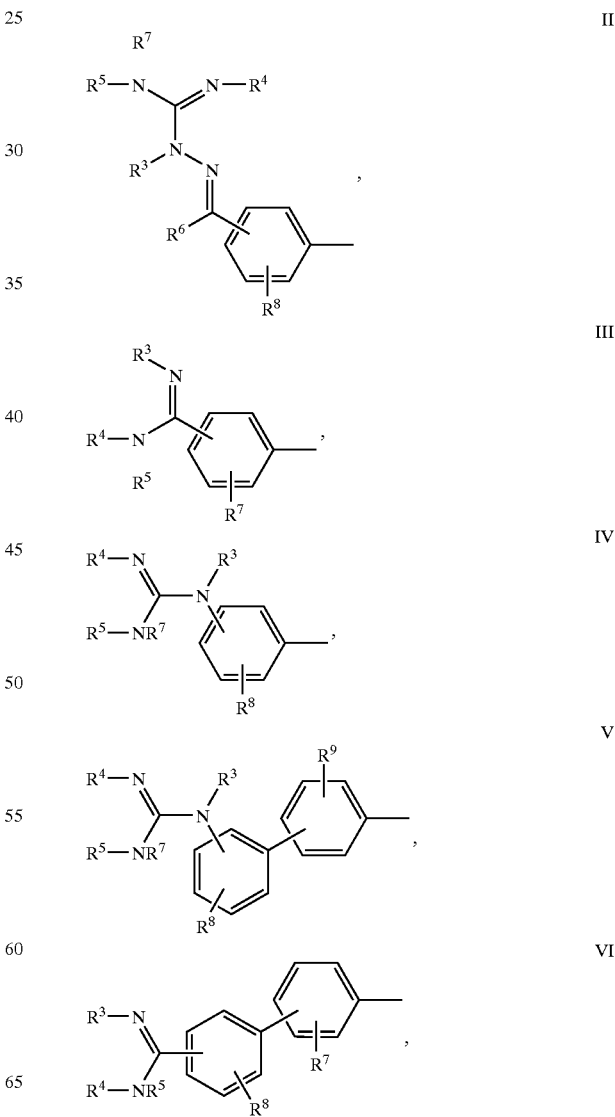

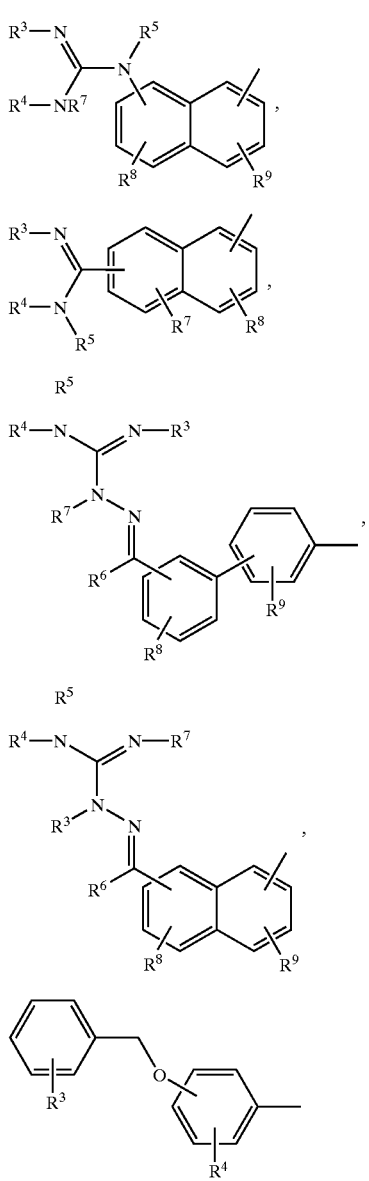

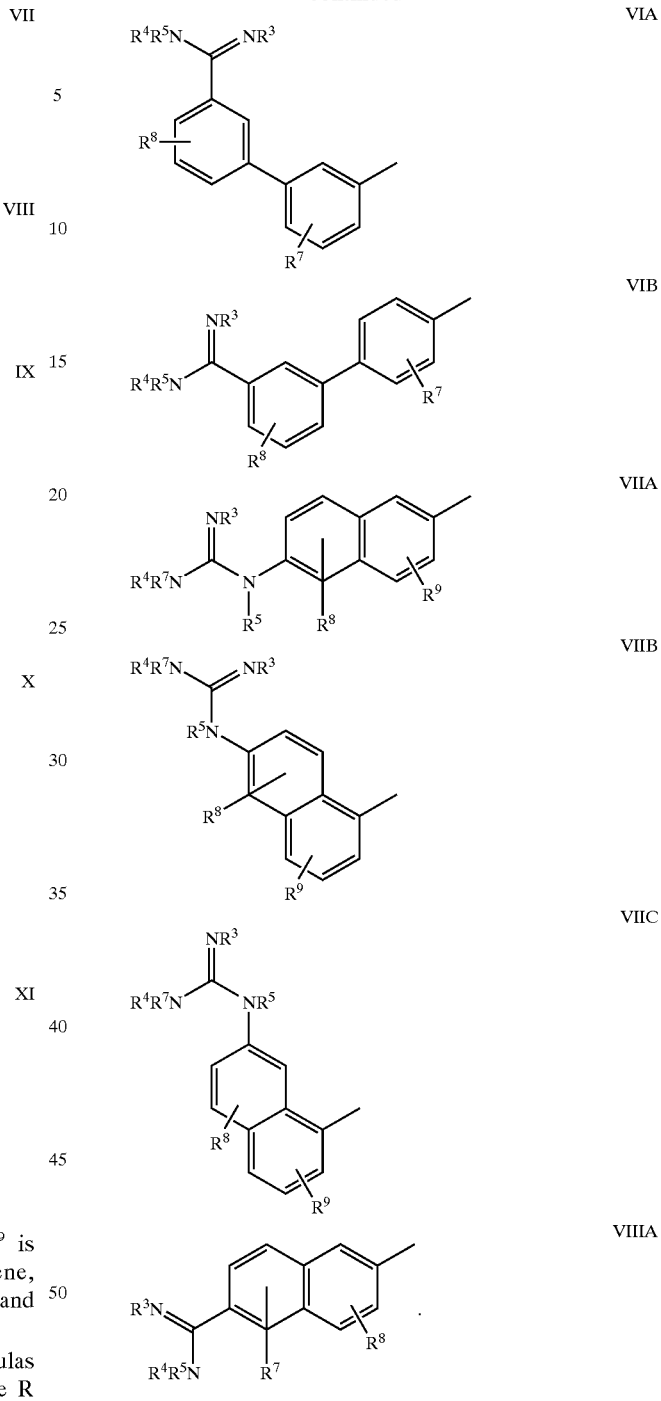

For formulas II–XI, each $R^3$, $R^4$, $R^5$, $R^7$, $R^8$, or $R^9$ is independently H, alkyl, aralkyl, heteroalkyl, alkene, heteroalkene, alkyne, heteroalkyne, aryl, or heteroaryl; and each $R^6$ is H, or alkyl.

Alternatively, Y may be selected from groups of formulas VA, VIA, VIB, VIIA, VIIB, VIIC, or VIIIA, with the R groups as defined for formula V, VI, VII, and VIII above.

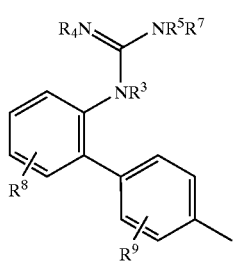

In other embodiments, Z is

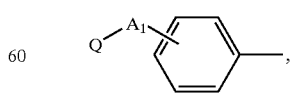

wherein $A_1$ is a bond or a linker of 1 or 2 atoms, and Q is aryl or heteroaryl. Alternatively, Z maybe selected from a group of formulas XII, XIII, XIV XV, and XVI:

XII
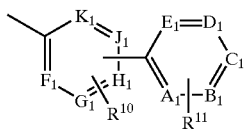

XIII
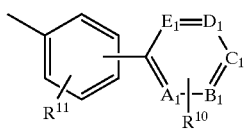

XIV
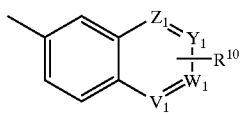

XV
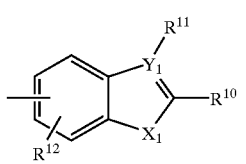

XVI
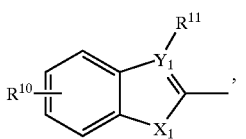

wherein $A_1$, $B_1$, $C_1$, $D_1$, $E_1$, $F_1$, $G_1$, $H_1$, $J_1$, $K_1$, $V_1$, $W_1$, and $Z_1$ are independently C, $CR^{13}$, or $NR^{14}$; $X_1$ is $CR^{15}$, $NR^{16}$, O, or S; $Y_1$ is C or N; and $R^{10}$, $R^{11}$, $R^{12}$, $R^{13}$, $R^{14}$, $R^{15}$, and $R^{16}$ are independently H, alkyl, aryl, amino, alkylamino, dialkylamino, hydroxy, alkoxy, nitro, or halogen.

A compound of formula I may have the formula:

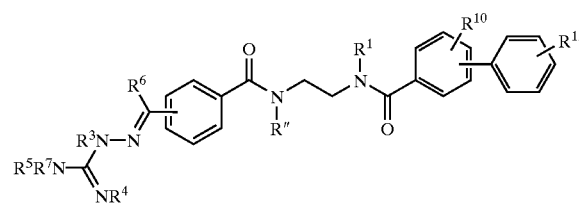

or a derivative, salt, racemic mixture, mixture of E/Z isomers, or mixture of diastereomers thereof with the R groups as defined for formulas I and XII. In certain embodiments, $R^1$, $R^3$, $R^4$, $R^5$, $R^7$, and R" are independently H, alkyl, aralkyl, heteroalkyl, or aryl; $R^6$ is H or alkyl; and $R^{10}$ and $R^{11}$ are independently H, halogen, hydroxy, alkoxy, amino, alkylamino, dialkylamino, alkyl, or nitro. In alternative embodiments, $R^6$ is methyl.

A compound of formula I may the formula:

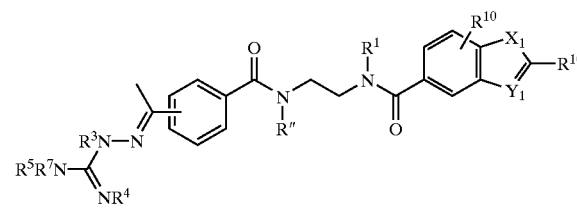

or a derivative, salt, racemic mixture, mixture of E/Z isomers, or mixture of diastereomers thereof, with the R groups as defined for formulas I and XV. In one embodiment, $R^1$, $R^3$, $R^4$, $R^5$, and R" are independently H, alkyl, aralkyl, heteroalkyl, or aryl; $R^7$ is H, halogen, hydroxy, alkoxy, amino, alkylamino, dialkylamino, alkyl, or nitro; $X_1$ is $CR^{15}$, $NR^{16}$, O or S; and $Y_1$ is CH or N; and $R^{10}$, $R^{12}$, $R^{15}$, and $R^{16}$ are independently H, alkyl, or aryl.

In another embodiment, the compound of formula I has the formula:

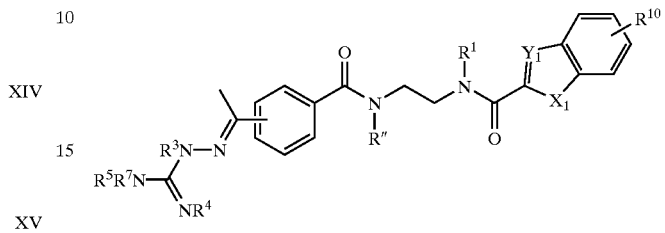

or a derivative, salt, racemic mixture, mixture of E/Z isomers, or mixture of diastereomers thereof with the R groups as defined for formulas I and XVI. In various embodiments, $R^1$, $R^3$, $R^4$, $R^5$, $R^7$, and R" are independently H, alkyl, aralkyl, heteroalkyl, or aryl; $R^{10}$ is H, halogen, hydroxy, alkoxy, amino, alkylamino, dialkylamino, alkyl, nitro, aryl, or heteroaryl; $X_1$ is O, S, or $NR^{16}$; $Y_1$ is N or $CR^{11}$, where $R^{11}$ and $R^{16}$ are independently H, alkyl, or aryl.

Exemplary compounds of formula I include:

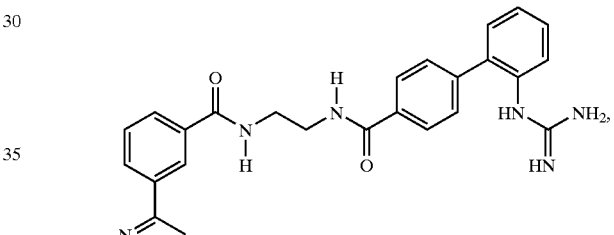

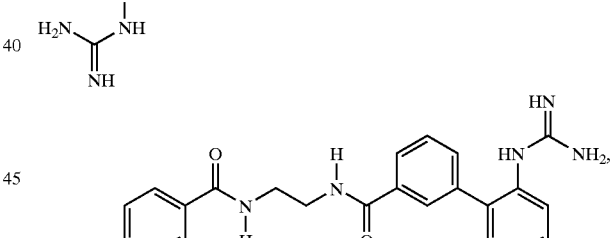

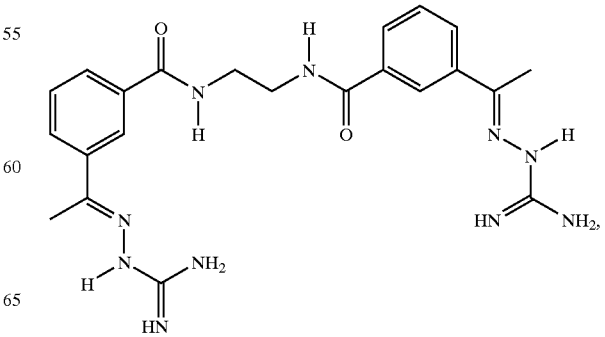

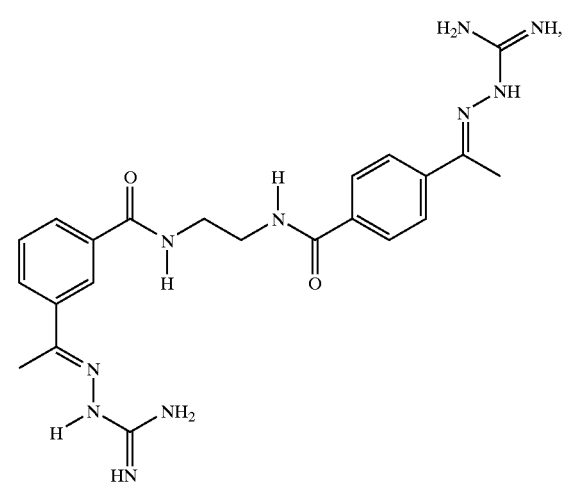
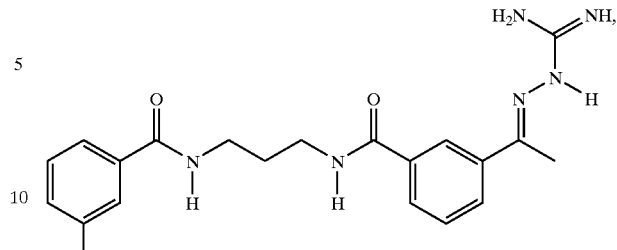
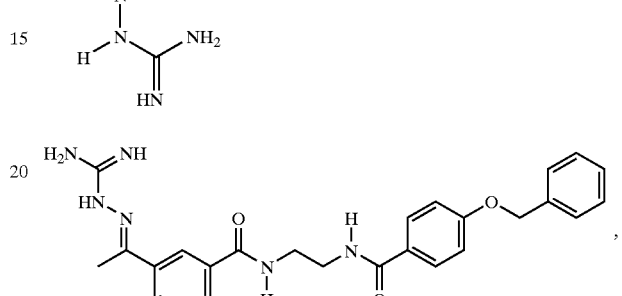
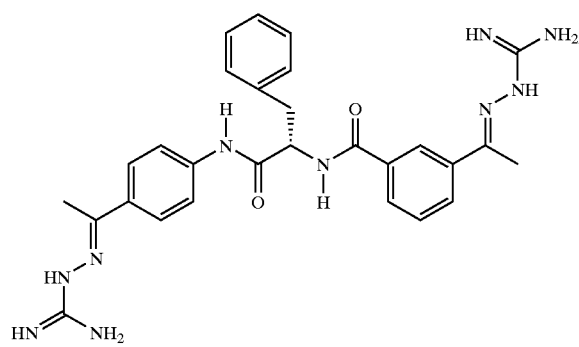
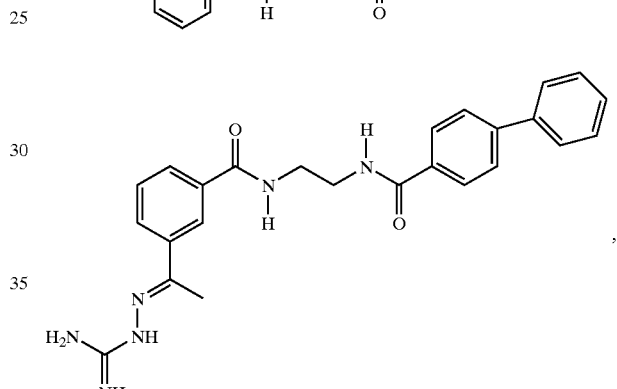
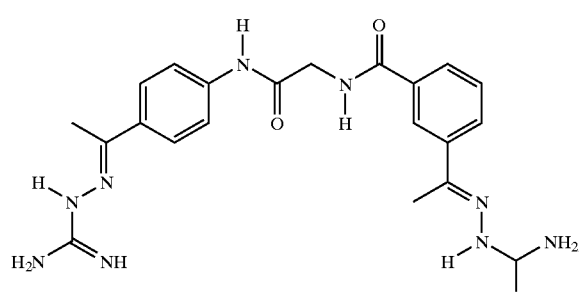
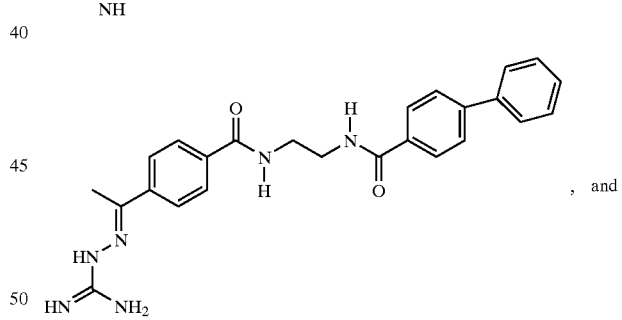
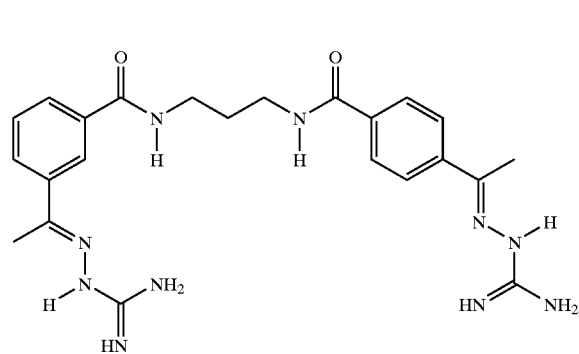
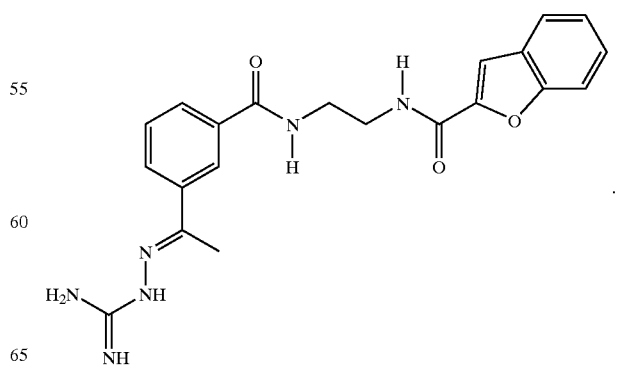

Additional compounds of claim 1 include:
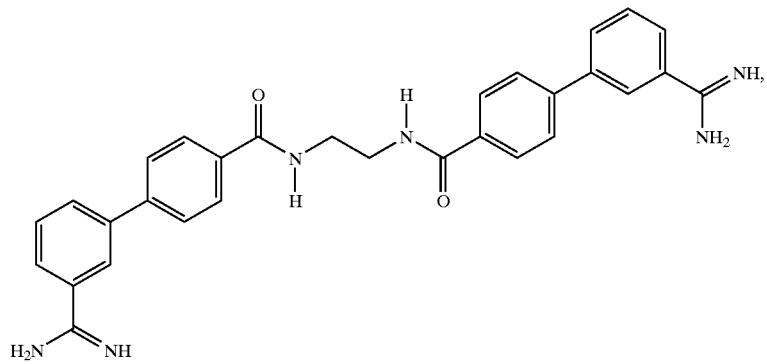
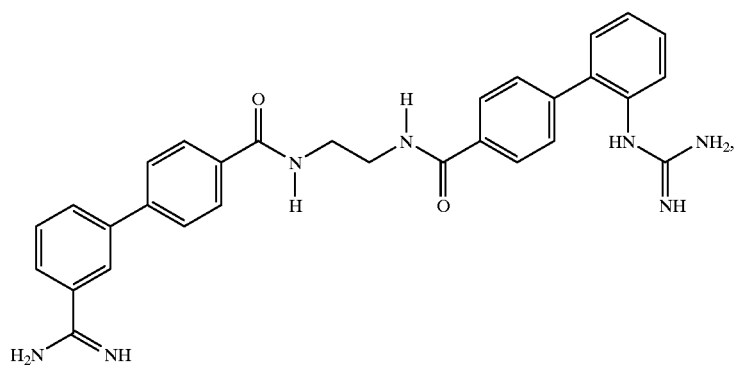
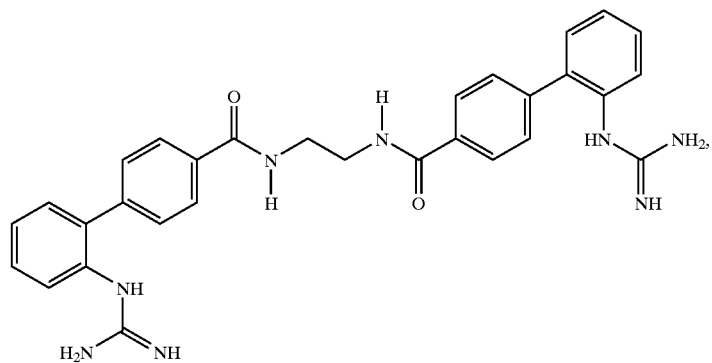
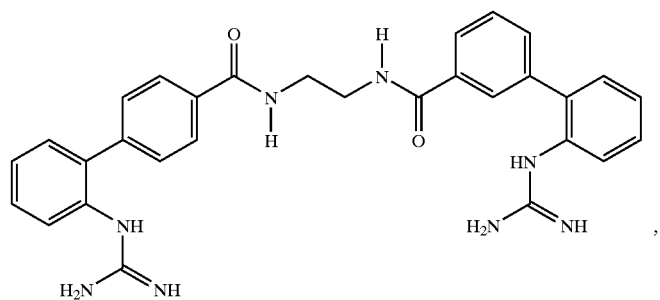

-continued
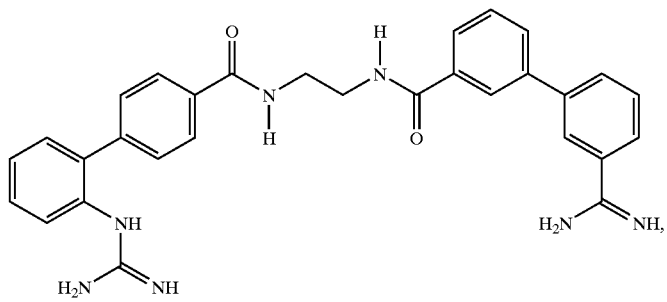
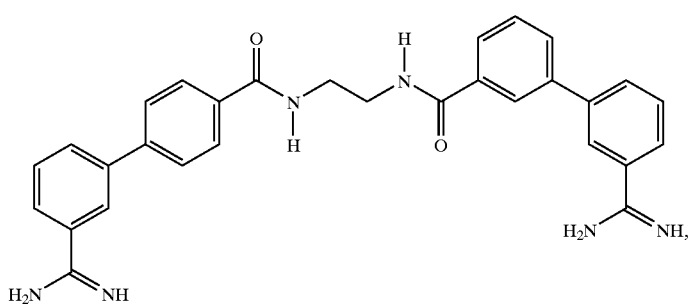
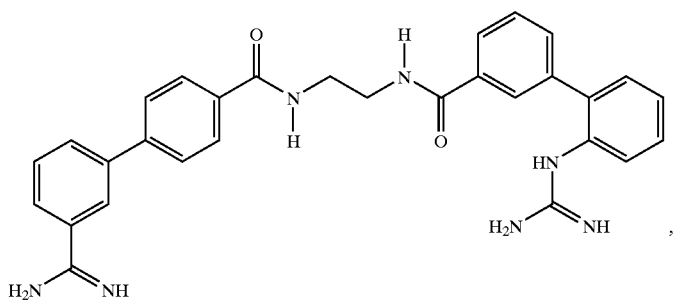
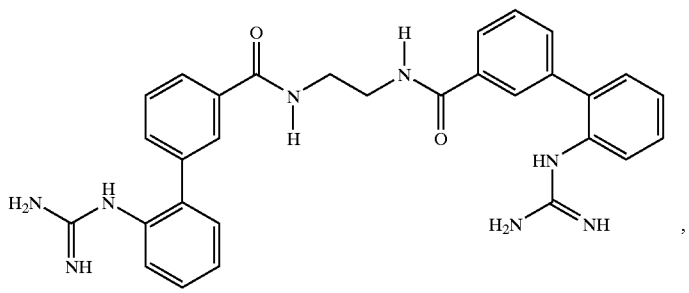
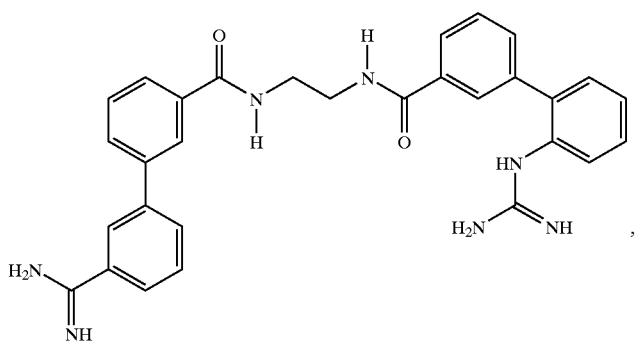

-continued
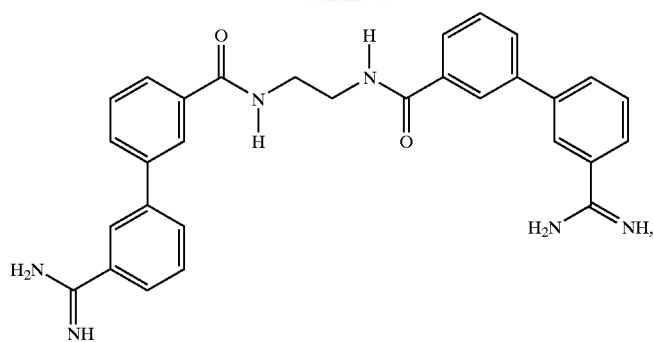
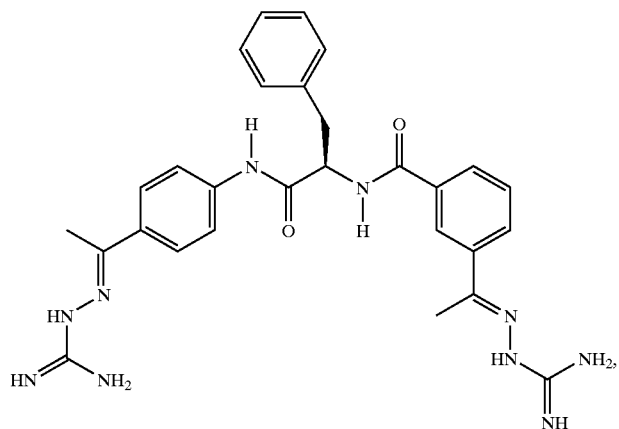
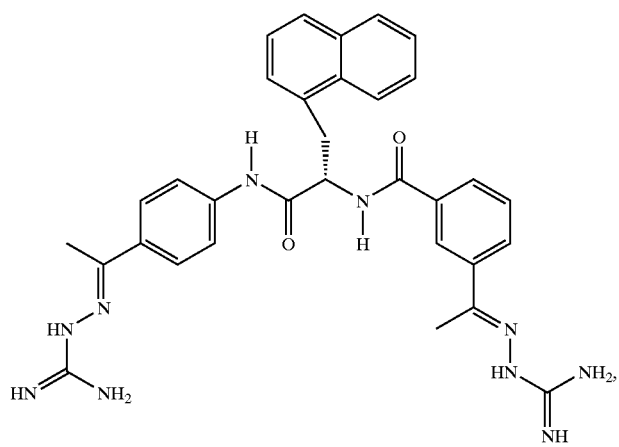
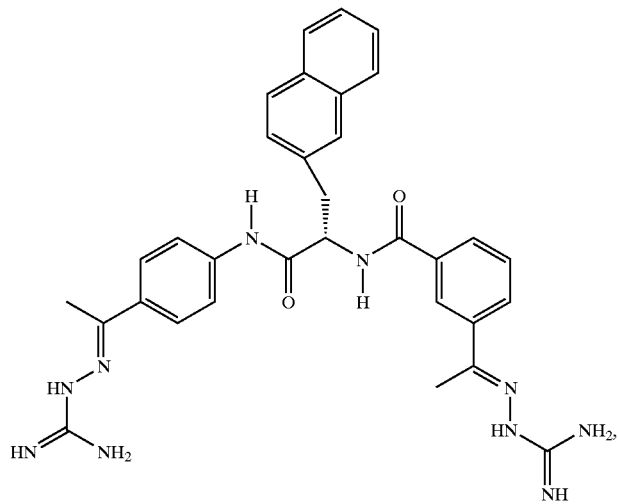

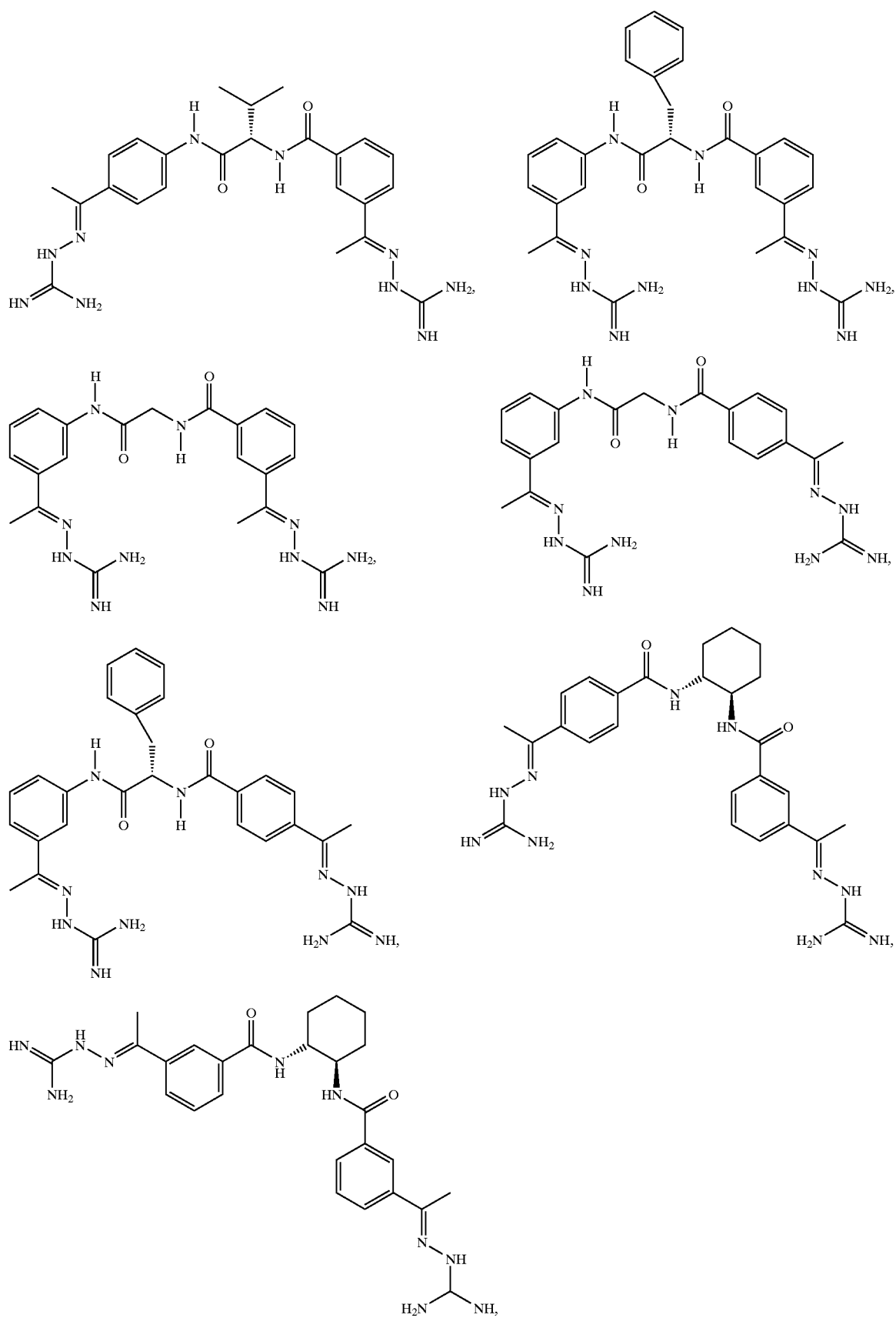

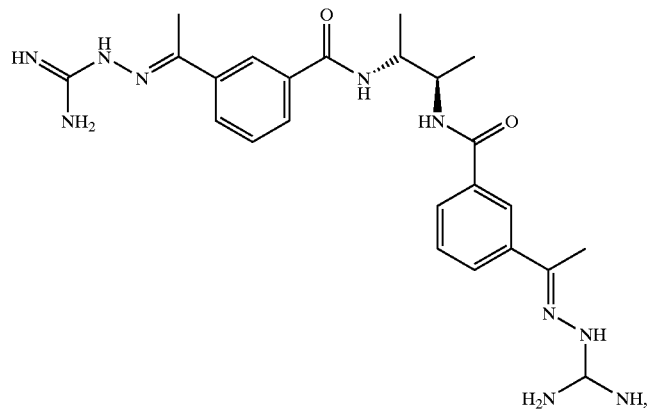
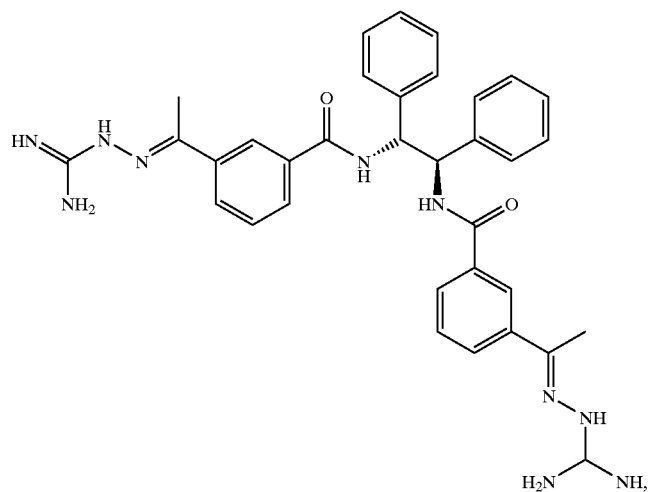
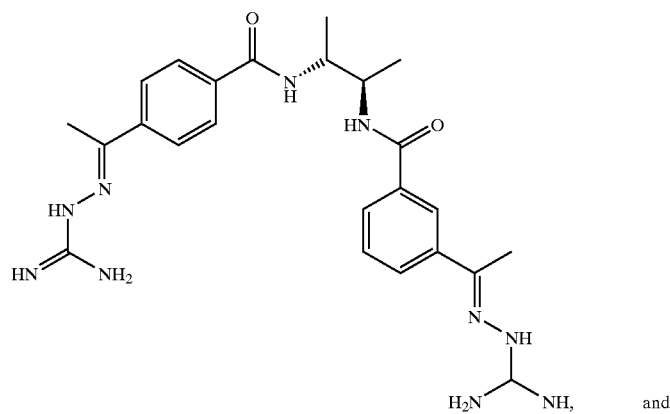
and

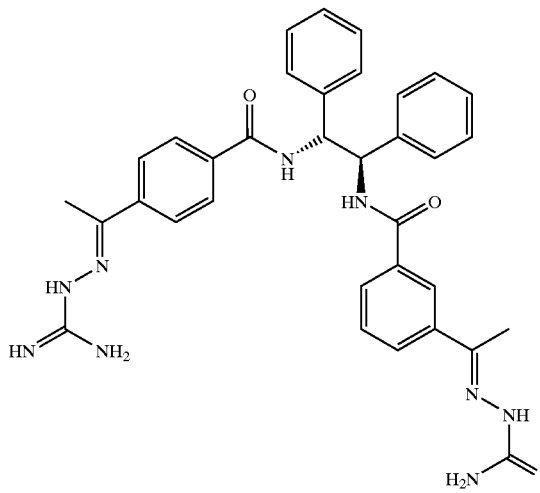

or racemic mixtures or mixtures of diastereomers thereof.

In another aspect, the invention features a guanylhydrazone compound of formula XVII:

XVII

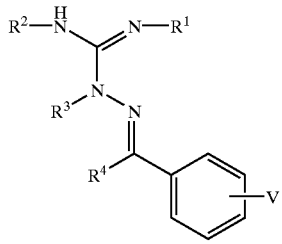

where V is selected from H, hydroxy, alkoxy, aryloxy, sulfhydryl, alkylthio, arylthio, halogen, fluoroalkyl, carboxyl, carboxyalkyl, amino, aminoalkyl, monosubstituted amino, disubstituted amino, quaternary amino, nitro, alkyl, heteroalkyl, alkene, heteroalkene, alkyne, heteroalkyne, aryl, and heteroaryl; $R^1$, $R^2$, and $R^3$ are independently H, alkyl, heteroalkyl, alkene, heteroalkene, alkyne, heteroalkyne, aryl, or heteroaryl; and $R^4$ is alkyl.

An exemplary compound of formula XVII is:

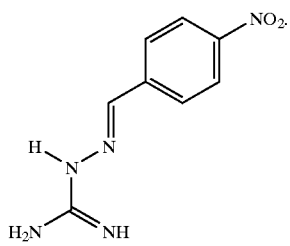

The invention further features a compound of formula XVIII:

XVIII

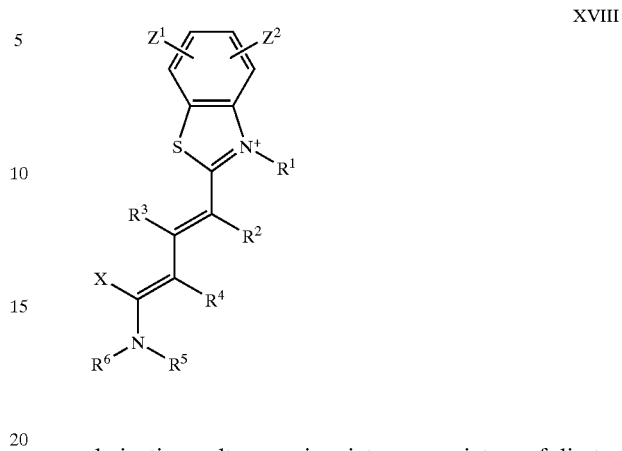

or a derivative, salt, racemic mixture, or mixture of diastereomers thereof, wherein $R^1$ and $R^5$ are independently lower alkyl; $R^2$, $R^3$, and $R^4$, are independently H or lower alkyl; $R^6$ is aryl, heteroaryl or $C(O)R^7$, wherein $R^7$ is alkyl, aryl, or substituted allyl; X is $OR^8$, $SR^9$, or $NR^{10}R^{11}$, wherein $R^8$, $R^9$, $R^{10}$, and $R^{11}$ are alkyl, alkenyl, or aryl, or X and $R^6$ taken together are a heterocyclic ring; and $Z^1$ and $Z^2$ are independently alkyl, aryl, alkenyl, alkynyl, halogen, cyano, nitro, or $OR^{12}$, wherein $R^{12}$ is alkyl, alkenyl, or aryl, or $SR^{13}$, where $R^{13}$ is alkyl, alkenyl, aryl, or $NR^{14}R^{15}$, where $R^{14}$ and $R^{15}$ are independently alkyl, alkenyl, or aryl, or $Z^1$ and $Z^2$ taken together form a ring that is optionally substituted.

An exemplary compound of formula XVIII is

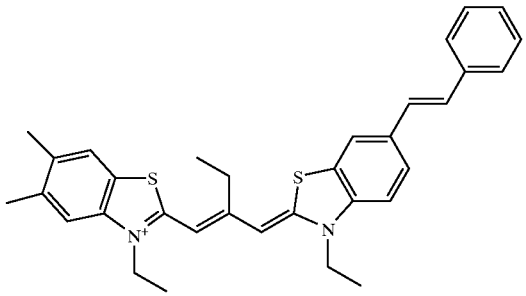

and

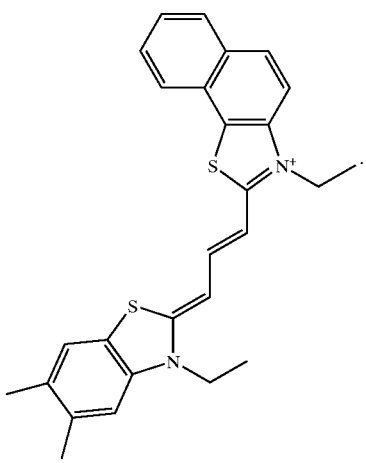

In another aspect, the invention features a compound of formula XIX:

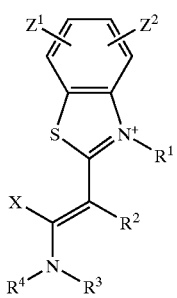

XIX or a derivative, salt, racemic mixture, or mixture of diastereomers thereof, wherein $R^1$ and $R^3$ are independently lower alkyl; $R^2$ is H or lower alkyl; $R^4$ is aryl, heteroaryl or $C(O)R^5$, wherein $R^5$ is alkyl, aryl, or substituted allyl; X is $OR^6$, $SR^7$, or $NR^8R^9$, wherein $R^6$, $R^7$, $R^8$, and $R^9$ are independently alkyl, alkenyl or aryl or X and $R^4$ taken together form a heterocyclic ring; and $Z^1$ and $Z^2$ are independently alkyl, aryl, alkenyl, alkynyl, halogen, cyano, nitro, or $OR^{10}$, where $R^{10}$ is alkyl, alkenyl, aryl, or $SR^{11}$, where $R^{11}$ is alkyl, alkenyl, aryl, or $NR^{12}R^{13}$, where $R^{12}$ and $R^{13}$ are independently alkyl, alkenyl, or aryl, or $Z^1$ and $Z^2$ taken together form a ring that is optionally substituted.

Exemplary compounds of formula XIX include:

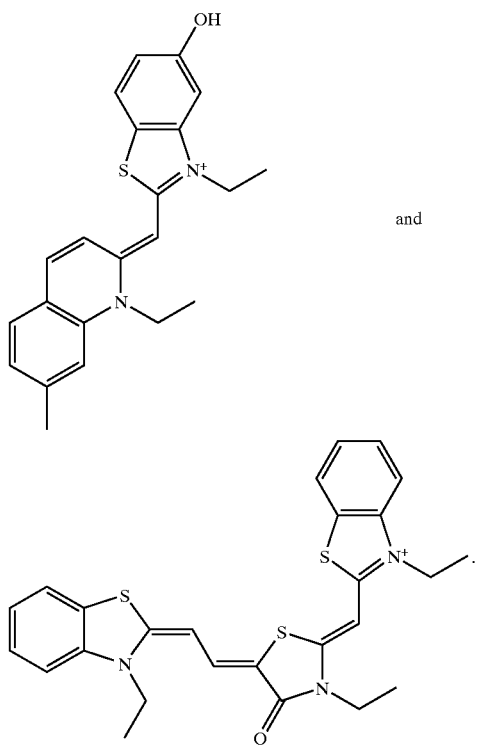

and

In another aspect the invention features a pharmaceutical composition included a pharmaceutically acceptable carrier and any one or more of the compounds of invention.

In yet another aspect, the invention features a method of killing or inhibiting the growth of bacteria that includes contacting bacteria or a site susceptible to bacterial growth with a pharmaceutical composition comprising a pharmaceutically acceptable carrier and an effective amount of one or more compounds of the invention. In various embodiment, the contacting is administering the pharmaceutical composition to a mammal, e.g., a human. The pharmaceutical composition is, for example, administered to the skin, hair, oral cavity, a mucous membrane, a wound, a bruise, a tooth, or an eye. The site susceptible bacterial growth may be, for example, an in-dwelling device in a patient, a medical device, a food, beverage, cosmetic, deodorant, contact lens product, food ingredient, enzyme compositions, a hard surface, or laundry. In various embodiments, the compound in the pharmaceutical composition inhibits a bacterial RNase P enzyme.

In desirable embodiments of any of the above aspects, the compound inhibits RNase P activity in vitro or in vivo, e.g., by at least 10%, 20%, 30%, 40%, 50%, 60%, 70%, 80%, 90%, 95%, 98% or 100%. Desirably, the RNase P that is inhibited is an RNase P holoenzyme described herein. In various embodiments, the compound specifically inhibits one RNase P holoenzyme or inhibits multiple RNase P holoenzymes from different bacterial genera or species. In one embodiment, the compound inhibits the activity of RNase P from one bacterial species by at least 2, 5, 10, 20, 50, 100, 500, or 1000 fold more than it inhibits the activity of RNase P from another species of bacteria.

In an embodiment of any of the above aspects, the step of contacting bacteria or a site susceptible to bacterial growth with the compound includes using one or more compounds of the invention as an antibacterial ingredient wherever such an ingredient is needed. For example, a compound of the invention can be used for the preservation of food, beverages, cosmetics, deodorants, contact lens products, food ingredients or enzyme compositions. Alternatively, a compound of the invention can be used as a disinfectant for use, e.g., on human or animal skin, hair, oral cavity, mucous membranes, wounds, bruises, or in the eye. In other embodiments, the compound is used for killing bacterial cells in laundry; or is incorporated into cleaning compositions or disinfectants for hard surface cleaning or for water treatment.

Accordingly, in further aspects, the invention provides a method of inhibiting bacteria present in laundry by treating the laundry with a soaking, washing or rinsing liquor that includes a compound of the invention; a method of inhibiting bacterial growth on a hard surface by contacting the surface with a compound of the invention; a method of inhibiting bacterial growth present in an industrial water line by contacting the water line with a compound of the invention; and a method of killing bacterial cells on human or animal skin, mucous membranes, teeth, wounds, bruises or in the eye or inhibiting the growth thereof by administering a compound of the invention to the relevant site on or in the animal.

In a further embodiment of any of the above aspects, the step of contacting bacteria or a site susceptible to bacterial growth with the compound includes contacting an in-dwelling device with the compound prior to, concurrent with, or following the administration of the in-dwelling device to a patient. In-dwelling devices include, but are not limited to, surgical implants, prosthetic devices, and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

In another embodiment of any of the above aspects, the method is used to treat, stabilize or prevent a bacterial infection in a mammal. In this method, the step of contacting bacteria or a site susceptible to bacterial infection (e.g., a site in or on the body of mammal) with the compound includes administering to the mammal the compound in an amount sufficient to treat, stabilize, or prevent the bacterial infection in the mammal.

In various embodiments of the invention, the mammal is a human, an animal of veterinary interest (e.g., cow, horse, dog, pig, sheep, or cat), or any other mammalian species.

In the desirable embodiments, the bacterial RNase P to be targeted by a compound of the invention is taken from a bacterium selected from the group consisting of *Chlamydophila pneumoniae, C. psittaci, C. abortus, Chlamydia trachomatis, Simkania negevensis, Parachlamydia acanthamoebae, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Salmonella typhimurium, S. typhi, S. paratyphi, S. enteritidis, Shigella dysenteriae, S. flexneri, S. sonnei, Enterobacter cloacae, E. aerogenes, Klebsiella pneumoniae, K. oxytoca, Serratia marcescens, Francisella tularensis, Morganella morganii, Proteus mirabilis, Proteus vulgaris, Providencia alcalifaciens, P. rettgeri, P. stuartii, Acinetobacter calcoaceticus, A. haemolyticus, Yersinia enterocolitica, Y. pestis, Y. pseudotuberculosis, Y. intermedia, Bordetella pertussis, B. parapertussis, B. bronchiseptica, Haemophilus influenzae, H. parainfluenzae, H. haemolyticus, H. parahaemolyticus, H. ducreyi, Pasteurella multocida, P. haemolytica, Branhamella catarrhalis, Helicobacter pylori, Campylobacter fetus, C. jejuni, C. coli, Borrelia burgdorferi, V. cholerae, V. parahaemolyticus, Legionella pneumophila, Listeria monocytogenes, Neisseria gonorrhea, N. meningitidis, Kingella dentrificans, K. kingae, K. oralis, Moraxella catarrhalis, M. atlantae, M. lacunata, M. nonliquefaciens, M. osloensis, M. phenylpyruvica, Gardnerella vaginalis, Bacteroides fragilis, Bacteroides distasonis, Bacteroides 3452A homology group, Bacteroides vulgatus, B. ovalus, B. thetaiotaomicron, B. uniformis, B. eggerthii, B. splanchnicus, Clostridium difficile, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis, Mycobacterium tuberculosis, M. avium, M. intracellulare, M. leprae, Streptococcus pneumoniae, S. agalactiae, S. pyogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Staphylococcus aureus, S. epidermidis, S. saprophyticus, S. intermedius, S. hyicus, S. haemolyticus, S. hominis,* and *S. saccharolyticus.* Accordingly, the invention discloses a method of treating infections by the bacteria above, among others.

In another aspect, the invention features a pharmaceutical composition that includes a compound described herein in any pharmaceutically acceptable form, including isomers such as E/Z isomers, diastereomers, and enantiomers, salts, solvates, and polymorphs thereof. In various embodiments, the composition includes a compound of the invention along with a pharmaceutically acceptable carrier or diluent.

By a "derivative" is meant a structural derivative having a chemical modification that enhances the bioavailability, solubility, stability, or potency of a compound in vivo or in vitro or that reduces the toxicity of a compound in vivo or in vitro. Desirably, the inhibition of RNase P activity by the derivative is at least 10%, 30%, 40%, 50%, 75%, 90%, 95%, or 100% of that by the compound from which the derivative was derived. Such modifications are known to those skilled in the field of medicinal chemistry.

By "alkyl" is meant a branched or unbranched saturated hydrocarbon group, desirably having from 1 to 20 or 1 to 50 carbon atoms. An alkyl may optionally include monocyclic, bicyclic, or tricyclic rings, in which each ring desirably has three to six members. The alkyl group may be substituted or unsubstituted. Exemplary substituents include alkoxy, aryloxy, sulfhydryl, alkylthio, arylthio, halogen, hydroxy, fluoroalkyl, perfluoroalkyl, amino, aminoalkyl, disubstituted amino, quaternary amino, hydroxyalkyl, carboxyalkyl, aryl, and carboxyl groups.

In various embodiments of the invention the alkyl group is of 1 to 5, 1 to 10, 1 to 15, 1 to 20, 1 to 50, 5 to 10, 5 to 15, 5 to 50, 10 to 15, 10 to 35, or 10 to 50 carbon atoms. Exemplary examples include methyl; ethyl; n-propyl; isopropyl; n-butyl; iso-butyl; sec-butyl; tert-butyl; pentyl; cyclopropyl; cyclobutyl; cyclopentyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; hexyl; heptyl; cyclohexyl; cycloheptyl; and cyclooctyl.

By "alkene" is meant a branched or unbranched hydrocarbon group containing one or more double bonds, desirably having from 2 to 20 or 2 to 50 carbon atoms. An alkene may optionally include monocyclic, bicyclic, or tricyclic rings, in which each ring desirably has five or six members. The alkene group may be substituted or unsubstituted. Exemplary substituents include alkoxy, aryloxy, sulfhydryl, alkylthio, arylthio, halogen, hydroxy, fluoroalkyl, perfluoroalkyl, amino, aminoalkyl, disubstituted amino, quaternary amino, hydroxyalkyl, carboxyalkyl, and carboxyl groups.

In various embodiments of the invention the alkene group is of 2 to 5, 2 to 10, 2 to 15, 2 to 20, 2 to 50, 5 to 10, 55to 15, 5to 50, 10 to 15, 10to 35, or 10 to 50 carbon atoms. Exemplary examples include vinyl; allyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

By "alkyne" is meant a branched or unbranched hydrocarbon group containing one or more triple bonds, desirably having from 2 to 20 or 2 to 50 carbon atoms. An alkyne may optionally include monocyclic, bicyclic, or tricyclic rings, in which each ring desirably has five or six members. The alkyne group may be substituted or unsubstituted. Exemplary substituents include alkoxy, aryloxy, sulfhydryl, alkylthio, arylthio, halogen, hydroxy, fluoroalkyl, perfluoroalkyl, amino, aminoalkyl, disubstituted amino, quaternary amino, hydroxyalkyl, carboxyalkyl, and carboxyl groups.

In various embodiments of the invention the alkyne group is of 2 to 5, 2 to 10, 2 to 15, 2 to 20, 2 to 50, 5 to 10, 5 to 15, 5 to 50, 10 to 15, 10 to 35, or 10 to 50 carbon atoms. Exemplary examples include ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl; 2-hexynyl, 3-hexynyl, 4-hexynyl, 5-hexynyl; 1-methyl-2-propynyl; 1-methyl-2-butynyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "heteroalkyl" is meant a branched or unbranched group, having from 1 to 50 atoms selected from the group consisting of carbon, nitrogen, oxygen, sulfur, or phosphorous. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halogen, hydroxy, fluoroalkyl, perfluoroalkyl, amino, aminoalkyl, disubstituted amino, quaternary amino, hydroxyalkyl, carboxyalkyl, and carboxyl groups By "heteroalkene" is meant a branched or unbranched group containing one or more double bonds, desirably having from 2 to 20 or 2 to 50 atoms selected from the group consisting of carbon, nitrogen, oxygen, sulfur, and phosphorous. A heteroalkene may optionally include monocyclic, bicyclic, or tricyclic rings, in which each ring desirably has five or six members. The heteroalkene group may be substituted or unsubstituted. Exemplary substituents include alkoxy, aryloxy, sulfhydryl, alkylthio, arylthio, halogen, hydroxy, fluoroalkyl, perfluoroalkyl, amino, aminoalkyl, disubstituted amino, quaternary amino, hydroxyalkyl, carboxyalkyl, and carboxyl groups.

By "heteroalkyne" is meant a branched or unbranched group containing one or more triple bonds, desirably having from 2 to 50 atoms selected from the group consisting of carbon, nitrogen, oxygen, sulfur, and phosphorous. A heteroalkyne may optionally include monocyclic, bicyclic, or tricyclic rings, in which each ring desirably has five or six members. The alkyne group may be substituted or unsubstituted. Exemplary substituents include alkoxy, aryloxy, sulfhydryl, alkylthio, arylthio, halogen, hydroxy, fluoroalkyl, perfluoroalkyl, amino, aminoalkyl, disubstituted amino quaternary amino, hydroxyalkyl, carboxyalkyl, and carboxyl groups.

By "aryl" is meant an aromatic group having a ring system comprised of carbon atoms with conjugated π electrons (e.g., phenyl). The ring of the aryl group is desirably 6 to 18 atoms. Aryl groups may optionally include monocyclic, bicyclic, or tricyclic rings, in which each ring desirably has five or six members. The aryl group may be substituted or unsubstituted. Exemplary subsituents include alkyl, hydroxy, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino groups.

By "heteroaryl" is meant an aromatic group having a ring system with conjugated π electrons (e.g., imidazole). The ring of the heteroaryl group is desirably 5 to 18 atoms selected from the group consisting of carbon, nitrogen, oxygen, sulfur, and phosphorous. Heteroaryl groups may optionally include monocyclic, bicyclic, or tricyclic rings, in which each ring desirably has five or six members. The heteroaryl group may be substituted or unsubstituted. Exemplary substituents include alkyl, hydroxy, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is an alkyl group.

By "hydroxyalkyl" is meant a chemical moiety with the formula —(R)—OH, wherein R is an alkyl group.

By "alkoxy" is meant a chemical substituent of the formula —OR, wherein R is an alkyl group.

By "aryloxy" is meant a chemical substituent of the formula —OR, wherein R is an aryl group.

By "alkylthio" is meant a chemical substituent of the formula —SR, wherein R is an alkyl group.

By "arylthio" is meant a chemical substituent of the formula —SR, wherein R is an aryl group.

By "quaternary amino" is meant a chemical substituent of the formula —(R)—N(R')(R'')(R''')$^+$, wherein R, R', R'', and R''' are each independently an alkyl, alkene, alkyne, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

By a "linker of" 1, 2, 3, 4, 5, 6, 7, or 8 "atoms" is meant a divalent radical having 1, 2, 3, 4, 5, 6, 7, or 8 atoms in a direct line between the sites of binding to other groups or a divalent cyclic structure having 3, 4, 5, 6, 7, or 8 atoms in the ring (or fused ring). It will be understood that additional atoms, e.g., H, may be present in the linker to satisfy the valency requirements of the constituent atoms. An exemplary linker is —CH$_2$CH$_2$—, which a linker of 2 atoms.

By "inhibiting bacterial growth" is meant preventing, reducing the rate or extent of, or stabilizing bacterial replication. By "stabilizing bacterial replication" is meant maintaining a bacterial population at an approximately constant level.

By inhibiting "RNase P activity" is meant decreasing the amount of an activity of an RNase P enzyme. For example, the amount of 5' terminal leader sequences that are cleaved from precursor tRNA's may be decreased. In various embodiments, the amount of an RNase P substrate (e.g., ptRNA$^{Gln}$) that is hydrolyzed in vitro or in vivo is decreased by at least 10%, 20%, 30%, 40%, 50%, 60%, 70%, 80%, 90%, 95%, or 100% relative to a corresponding control without an RNase P inhibitor. In other embodiments, the percentage of fluorescence in the presence of a candidate compound in comparison to the absence of the candidate compound is less than 90%, 80%, 70%, 60%, 50%, 40%, 30%, 20%, 10%, 5% or 2%, as calculated using equation 1, with solutions prepared as described in Example 10. In this equation, f is the fluorescence in counts per second; (f.enzyme+probe) is the fluorescence observed when enzymatic activity is uninhibited; (f.probe) is the fluorescence observed without enzymatic activity; and (f.compound+ enzyme+probe) is the fluorescence observed when the enzymatic activity is modulated by a compound of the invention. In other embodiments, the level of RNase P activity is at least 2, 5, 10, or 20 fold lower in the presence of a candidate inhibitor than in the absence of the candidate inhibitor. In another embodiment, a compound decreases RNase P activity by inhibiting assembly of the RNase P holoenzyme. In still other embodiments, a compound decreases RNase P activity by inhibiting the binding of RNase P (RNA subunit, or protein subunit, or holoenzyme) to another molecule (e.g., a substrate); or the enzymatic activity of an RNase P holoenzyme, as measured using standard assays such as these described herein or any other standard assay (see, for example, Ausubel et al., Current Protocols in Molecular Biology, Wiley: New York, 2000). An exemplary assay is described in Example 23. In this example, the cleavage of ptRNA$^{Gln}$ by the enzyme N. Gonorrhea RNase P is monitored in the presence and absence of a candidate compound, and the progress of the RNase P-mediated cleavage reaction is assessed by measuring the fluorescence polarization level of a TAMRA moiety hybridized to the cleaved substrate.

$$\left[1 - \left(\frac{(f \cdot compound + enzyme + probe) - (f \cdot enzyme + probe)}{(f \cdot probe) - (f \cdot enzyme + probe)}\right)\right] \times 100 \quad \text{Eq 1.}$$

By "treating" is meant administering a pharmaceutical composition for prophylactic and/or therapeutic purposes. To "prevent disease" refers to prophylactic treatment of a subject who is not yet infected, but who is susceptible to, or otherwise at risk of, a particular infection. To "treat disease" or use for "therapeutic treatment" refers to administering treatment to a subject already suffering from an infection to improve the subject's condition.

By "effective amount" is meant an amount of a compound sufficient to kill bacteria or inhibit bacterial growth. This amount may vary from compound to compound and may depend on the route of administration.

By "bacterial infection" is meant the invasion of a host animal, e.g., a mammal, by pathogenic bacteria. For example, the infection may include the excessive growth of bacteria that are normally present in or on the body of a mammal or growth of bacteria that are not normally present in or on the mammal. More generally, a bacterial infection can be any situation in which the presence of a bacterial population(s) is damaging to a host mammal. Thus, a mammal is "suffering" from a bacterial infection when an excessive amount of a bacterial population is present in or on the mammal's body, or when the presence of a bacterial population(s) is damaging the cells or other tissue of the mammal. In one embodiment, the number of a particular genus or species of bacteria is at least 2, 4, 6, or 8 times the number normally found in the mammal. The bacterial infection may be due to gram positive and/or gram negative bacteria or any other class of bacteria.

By "administration" or "administering" is meant a method of giving one or more unit doses of an antibacterial pharmaceutical composition to an animal, e.g., a mammal (e.g., topical, oral, intravenous, intraperitoneal, or intramuscular administration). The method of administration may vary depending on various factors, e.g., the components of the pharmaceutical composition, site of the potential or actual bacterial infection, bacteria involved, and severity of the actual bacterial infection.

By "nucleic acid" is meant a combination of two or more covalently bonded nucleotides. Exemplary nucleic acids include mRNA, cDNA, genomic DNA, complementary antisense nucleic acids capable of decreasing RNase P activity, naturally occurring nucleic acids and synthetic (e.g., chemically synthesized) nucleic acids. The nucleic acid may be double-stranded or single-stranded. Where single-stranded, the nucleic acid may be a sense strand or an antisense strand.

By "isolated nucleic acid" is meant a DNA or RNA that is separated from the coding sequences with which it is naturally contiguous (one on the 5' end and one on the 3' end) in the genome of the organism from which it is derived. Thus, in one embodiment, an isolated nucleic acid includes some or all of the 5' and/or 3' non-coding (e.g., promoter) sequences which are immediately contiguous to the coding sequence. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "isolated polypeptide" is meant a preparation which is at least 60% by weight (dry weight) the polypeptide of interest. Desirably the preparation is at least 75%, more desirably at least 90%, and most desirably at least 99%, by weight the polypeptide of interest. Purity can be measured by any appropriate standard method, e.g., column chromatography, polyacrylamide gel electrophoresis, or HPLC analysis.

Moreover, an "isolated" nucleic acid or polypeptide is meant to include fragments which are not naturally occurring as fragments and would not be found in the natural state.

By "a polypeptide containing RNase P activity" is meant a polypeptide that, when combined with an RNA subunit to form an RNase P holoenzyme, has 20%, 50%, 75%, or even 100% or more, of the enzymatic activity of an E. coli or B. subtilis RNase P holoenzyme. Desirably, the RNA subunit is from the same species when activity is tested. The enzymatic activity can be assessed, for example, by measuring hydrolysis of an RNase P substrate. Standard methods for conducting such hydrolysis assays are described herein and in the literature (see, for example, Altman and Kirsebom, Ribonuclease P, The RNA World, 2nd Ed., Cold Spring Harbor Laboratory Press: Cold Spring Harbor, N.Y., 1999; Pascual and Vioque, Proc. Natl. Acad. Sci. 96: 6672, 1999; Geurrier-Takada et al., Cell 35: 849, 1983; Tallsjö and Kirsebom, Nucleic Acids Research 21: 51, 1993; Peck-Miller and Altman, J. Mol. Biol. 221: 1, 1991; Gopalan et al., J. Mol. Biol. 267: 818, 1997; and WO 99/11653).

By "RNase P substrate" is meant a molecule which is cleaved by an RNase P holoenzyme.

By "identity" is meant the relationship between two or more polypeptide sequences or two or more nucleic acid sequences, as determined by comparing the degree of sequence relatedness. "Identity" can be readily calculated by known methods, including but not limited to those described in Computational Molecular Biology, Lesk, A. M., ed., Oxford University Press: New York, 1988; Biocomputing: Informatics and Genome Projects, Smith, D. W., ed., Academic Press: New York, 1993; Computer Analysis of Sequence Data, Part I, Griffin, A. M., and Griffin, H. G., eds., Humana Press: New Jersey, 1994; von Heinje Sequence Analysis in Molecular Biology, Academic Press: 1987; Sequence Analysis Primer, Gribskov, and Devereux, eds., M. Stockton Press: New York, 1991; and Carillo and Lipman, SIAM J. Applied Math. 48: 1073, 1988. Methods to determine identity are designed to give the largest match between the sequences tested. Moreover, methods to determine identity are available in publicly available computer programs.

Computer program methods to determine identity between two sequences include, but are not limited to, the GCG program package (Devereux et al., Nucleic Acids Research 12(1): 387, 1984), BLASTP, BLASTN, and FASTA (Altschul et al., J. Mol. Biol. 215: 403 (1990). The well known Smith Waterman algorithm may also be used to determine identity. The BLAST program is publicly available from NCBI and other sources (*BLAST Manual*, Altschul, et al., NCBI NLM NIH Bethesda, Md. 20894).

As an illustration of percent identity, if a test nucleic acid sequence (TN) has 95% identity to a reference nucleic acid sequence (RN) at the specified bases, then TN is identical to RN at the specified bases, except that TN may include point mutations in 5% of the total number of nucleic acids present in RN. Thus, 5% of nucleic acids found in RN may be deleted or substituted with another nucleic acid. In addition, the sequence of TN may contain, as compared to the specified RN bases, insertions of nucleic acids totaling up to 5% of the nucleic acids present in RN. These mutations, as compared to the RN sequence, may occur at the 5' or 3' terminal positions or anywhere between those terminal positions, interspersed either individually among the specified nucleic acids or in one or more contiguous groups of specified nucleic acids. As in the present invention, for nucleic acids encoding proteins, trinucleotide sequences encoding the same amino acid may optionally be treated as identical.

Analogously, a test polypeptide (TP) has an amino acid sequence 95% identical to a reference amino acid sequence (RP) if TP is identical to RP at the specified amino acids, except that TP contains amino acid alterations totaling 5% of the total number of specified amino acids in RP. These alterations include deletions of amino acids or substitutions with one or more other specified amino acids. In addition, the alterations include insertions of other amino acids totaling up to 5% of the total amino acids present in the specified RP amino acids. The alterations in the TP amino acid sequence as compared to the RP sequence may occur at the amino or carboxy terminal positions, or anywhere between those terminal positions, interspersed either individually among residues or in one or more contiguous groups.

By "an RNase P consensus sequence" is meant a sequence which, when aligned to the *E. coli* RNase P sequence using the ClustalW program and performing a comparison of the specified amino acid sequences, shows conservation of at least nine of the following specified 20 amino acid residues in the *E. coli* RNase P protein subunit: R11, L12, F18, R46, G48, V51, K53, K54, A59, V60, R62, N63, K66, R67, R70, L80, D84, V86, L101, and L105. Desirably, the consensus sequence conserves at least 13 of the 20 residues. It is also desired that the aligned consensus sequence contain at least seven of the following subset of nine amino acid residues in the *E. coli* RNase P protein: F18, R46, K53, A59, R62, N63, K66, R67, R70, more desirably, at least eight of the amino acids, and, most desirably, all nine amino acids of the above subset. For the purpose of determining identity in the present invention, identity of amino acids other than those for which the amino acid is specified in the consensus sequence are ignored in the comparison when calculating identity of nucleic acids encoding an RNase P consensus sequence, and degenerate codons encoding the designated amino acid are treated as identical.

A "substantially identical" RNase P sequence is one which has or encodes a polypeptide having at least 95% identity, desirably 100% identity, to the twenty amino acids provided from the sequence of *E. coli* RNase P hereinbefore above.

By "transformation" or "transfection" is meant any method for introducing foreign molecules, such as nucleic acids, into a cell. Lipofection, DEAE-dextran-mediated transfection, microinjection, protoplast fusion, calcium phosphate precipitation, retroviral delivery, electroporation, and biolistic transformation are just a few of the methods known to those skilled in the art which may be used. These techniques may be applied for the transformation or transfection of a wide variety of cell types and intact tissues including, without limitation, intracellular organelles (e.g., and mitochondria and chloroplasts), bacteria, yeast, fungi, algae, animal tissue, and cultured cells.

By "transgenic host cell" is meant a cell (or a descendent of a cell) transformed or transfected with a heterologous nucleic acid sequence comprising a coding sequence operably linked to one or more sequence elements, e.g., a promoter, which directs transcription and/or translation such that the heterologous coding sequence is expressed in said host cell. The transgenic host cells may be, either stably or transiently transfected.

By "operably linked" is meant that a selected nucleic acid is positioned adjacent to one or more sequence elements, e.g., a promoter, which directs transcription and/or translation of the selected nucleic acid.

By an "antibody that specifically binds" is meant an antibody that recognizes and binds to a full length RNase P protein or subfragment, for example, any one of SEQ ID NOS: 20–38 or 50–60, but which does not substantially recognize and bind to other molecules in a sample, including other RNase P proteins.

The compounds of the invention that inhibit RNase P activity have a variety of advantages. For example, the inhibitors may provide a selective antibacterial treatment that reduces the adverse side effects associated with killing nonpathogenic bacteria. Use of such selective inhibitors also reduces the risk of producing a wide range of resistant bacterial strains.

Other features and advantages of the invention will be apparent from the following detailed description and from the claims.

BRIEF DESCRIPTION OF THE DRAWINGS

FIG. 3 is a table of RNase P inhibition data, bacterial growth inhibition data, and cell toxicity data for some compounds of the invention. The data was collected as described in Example 23 (RNase P inhibition), Example 24 (bacterial growth inhibition), and Example 25 (cell toxicity). The experimental value is given as a percentage of the control experiment.

FIGS. 4A–4C are depictions of the alignment of previously known bacterial RNase P protein subunits (SEQ ID NOS: 61–114) aligned using the ClustalW alignment program (Thompson et al., Nucleic Acids Research 22:4673, 1994) and the alignment of the RNase P sequences disclosed in U.S. Ser. No. 09/798,635 filed Mar. 1, 2000. The aligned fragments of the RNase P sequences are designated by (*).

FIGS. 5A–5S are listings of the nucleic acid sequences (SEQ ID NOS: 1–19) encoding the amino acid sequences (SEQ ID NOS: 20–38) of the bacterial RNase P polypeptides disclosed in U.S. Ser. No. 09/798,635 filed Mar. 1, 2000. The nucleic acid and amino acid sequences were derived from the following pathogenic bacterial species: *Streptococcus mutans* (FIG. 5A; SEQ ID NOS: 1 and 20, respectively); *Klebsiella pneumoniae* (FIG. 5B; SEQ ID NOS: 2 and 21, respectively); *Salmonella paratyphi* A (FIG. 5C; SEQ ID NOS: 3 and 22, respectively); *Pseudomonas aeruginosa* (FIG. 5D; SEQ ID NOS: 4 and 23, respectively); *Corynebacterium diphtheriae* (FIG. 5E; SEQ ID NOS: 5 and 24, respectively); *Chlamydia trachomatis* (FIG. 5F; SEQ ID NOS: 6 and 25, respectively); *Vibrio cholerae* Serotype 01, Biotype E1 Tor, Strain N16961 (FIG. 5G; SEQ ID NOS: 7 and 26, respectively); *Neisseria gonorrhoea* FA 1090 (FIG. 5H; SEQ ID NOS: 8 and 27, respectively); *Neisseria meningitidis* Serogroup A, Strain Z2491 (FIG. 5I; SEQ ID NOS: 9 and 28, respectively); *Streptococcus pyogenes* M1 (FIG. 5J; SEQ ID NOS: 10 and 29, respectively); *Bordetella pertussis* Tohama I (FIG. 5K; SEQ ID NOS: 11 and 30, respectively); *Porphyromonas gingivalis* W83 (FIG. 5L; SEQ ID NOS: 12 and 31, respectively); *Streptococcus pneumoniae* Type 4 (FIG. 5M; SEQ ID NOS: 13 and 32, respectively); *Clostridium difficile* 630 (FIG. 5N; SEQ ID NOS: 14 and 33, respectively); *Camphylobacter jejuni* NCTC (FIG. 5O; SEQ ID NOS: 15 and 34, respectively); *Bacillus anthracis* Ames (FIG. 5P; SEQ ID NOS: 16 and 35, respectively); *Mycobacterium avium* 104 (FIG. 5Q; SEQ ID NOS: 17 and 36, respectively); *Staphylococcus aureus* NCTC 8325 (FIG. 5R; SEQ ID NOS: 18 and 37, respectively); and *Staplylococcus aureus* COL (FIG. 5S; SEQ ID NOS: 19 and 38, respectively).

FIGS. 6A–6K are listings of the nucleic acid sequences (SEQ ID NOS: 39–49) encoding the amino acid sequences (SEQ ID NOS: 50–60) of additional bacterial RNase P polypeptides disclosed in U.S. Ser. No. 09/798,635 filed Mar. 1, 2000. The nucleic acid and amino acid sequences were derived from the following pathogenic bacterial species: *Pasteurella multocida* PM70 (FIG. 6A; SEQ ID NOS: 39 and 50, respectively); *Haemophilus ducreyi* strain 35000HP (FIG. 6B; SEQ ID NOS: 40 and 51, respectively); *Chlamydia muridarum* (FIG. 6C; SEQ ID NOS: 41 and 52, respectively); *Chlamydophila psittaci* (FIG. 6D; SEQ ID NOS: 42 and 53, respectively); *Treponema denticola* (FIG. 6E; SEQ ID NOS: 43 and 54, respectively); *Enterococcus faecalis* (FIG. 6F; SEQ ID NOS: 44 and 55, respectively); *Legionella pneumophila* (FIG. 6G; SEQ ID NOS: 45 and 56, respectively); *Staphylococcus epidermis* (FIG. 6H; SEQ ID NOS: 46 and 57, respectively); *Mycobacterium smegmatis* (FIG. 6I; SEQ ID NOS: 47 and 58, respectively); *Burkholderia pseudomallei* (FIG. 6J; SEQ ID NOS: 48 and 59, respectively); and *Ureaplasma urealyticum* (FIG. 6K; SEQ ID NOS: 49 and 60, respectively).

DETAILED DESCRIPTION OF THE INVENTION

Figure 1A:
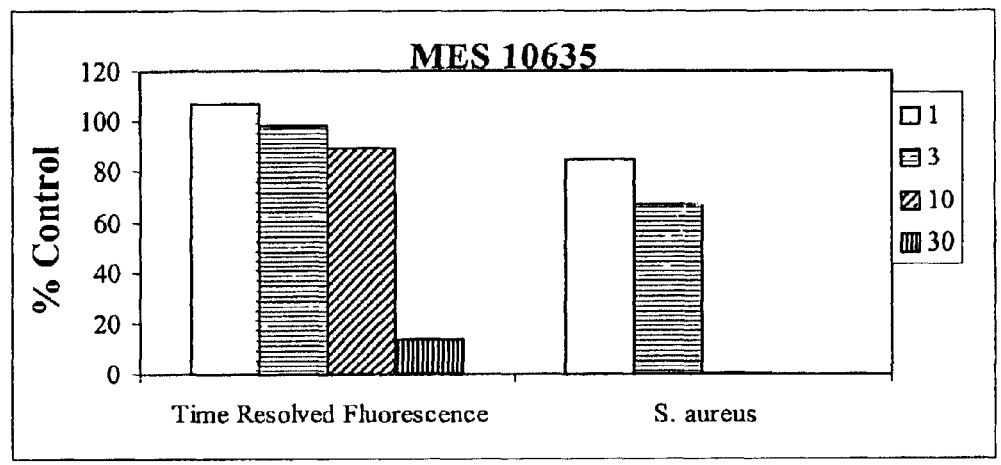
FIGS. 1A and 1B are bar graphs illustrating the activity of MES 10635 and MES 10636. The fluorescence data illustrates that these compounds can inhibit a representative RNase P (*N. gonorrhoeae*). The *S. aureus* data illustrates that these compounds can inhibit bacterial growth. Doses are in $\mu$M.

We have identified compounds that inhibit RNase P activity and that are useful for killing bacteria or inhibiting bacterial growth, e.g., to treat or prevent infection. The compounds of the invention include guanylhydrazones (e.g., mono or bis), guanylhydrazone mimetics (i.e., compounds that mimic the charge and geometry of a guanylhydrazone), and benzothiazolium compounds.

Some inhibitors of RNase P activity that we have identified have the chemical structure of formula I:

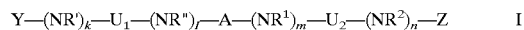

where $U_1$ and $U_2$ are independently carbonyl, thiocarbonyl, or sulfonyl; k, l, m, and n are independently 0 or 1; A is a linker of 1, 2, 3, 4, 5, 6, 7, or 8 atoms that is optionally substituted with a group selected from alkyl, heteroalkyl, alkene, heteroalkene, alkyne, heteroalkyne, aryl, alkaryl, and heteroaryl, the R groups are independently H, alkyl, heteroalkyl, alkene, heteroalkene, alkyne, heteroalkyne, aryl, or heteroaryl, and Y and Z can be various phenyl groups substituted with a guanylhydrazone or other substituent as described herein.

Additional guanylhydrazone compound of the invention have the chemical structure of formula XVII:

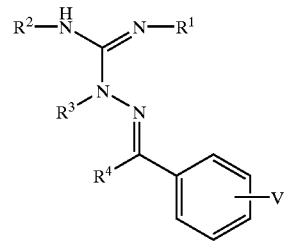

where V is selected from H, hydroxy, alkoxy, aryloxy, sulfhydryl, alkylthio, arylthio, halogen, fluoroalkyl, carboxyl, carboxyalkyl, amino, aminoalkyl, monosubstituted amino, disubstituted amino, quaternary amino, nitro, alkyl, heteroalkyl, alkene, heteroalkene, alkyne, heteroalkyne, aryl, and heteroaryl; $R^1$, $R^2$, and $R^3$ are independently H, alkyl, heteroalkyl, alkene, heteroalkene, alkyne, heteroalkyne, aryl, or heteroaryl; and $R^4$ is alkyl.

Benzothiazolium compounds of the invention can be represented by formulas XVIII and XIX:

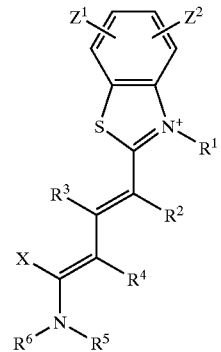

-continued

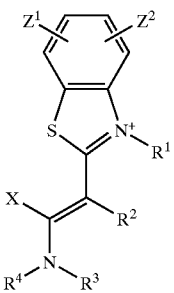

For formula XVIII, $R^1$ and $R^5$ are independently lower alkyl; $R^2$, $R^3$, and $R^4$, are independently H or lower alkyl; $R^6$ is aryl, heteroaryl or $C(O)R^7$, wherein $R^7$ is alkyl, aryl, or substituted allyl; X is $OR^8$, $SR^9$, or $NR^{10}R^{11}$, wherein $R^8$, $R^9$, $R^{10}$, and $R^{11}$ are alkyl, alkenyl, or aryl, or X and $R^6$ taken together are a heterocyclic ring; and $Z^1$ and $Z^2$ are independently alkyl, aryl, alkenyl, alkynyl, halogen, cyano, nitro, or $OR^{12}$, wherein $R^{12}$ is alkyl, alkenyl, or aryl, or $SR^{13}$, where $R^{13}$ is alkyl, alkenyl, aryl, or $NR^{14}R^{15}$, where $R^{14}$ and $R^{15}$ are independently alkyl, alkenyl, or aryl, or $Z^1$ and $Z^2$ taken together form a ring that is optionally substituted. For formula XIX $R^1$ and $R^3$ are independently lower alkyl; $R^2$ is H or lower alkyl; $R^4$ is aryl, heteroaryl or $C(O)R^5$, wherein $R^5$ is alkyl, aryl, or substituted allyl; X is $OR^6$, $SR^7$, or $NR^8R^9$, wherein $R^6$, $R^7$, $R^8$, and $R^9$ are independently alkyl, alkenyl or aryl or X and $R^4$ taken together form a heterocyclic ring; and $Z^1$ and $Z^2$ are independently alkyl, aryl, alkenyl, alkynyl, halogen, cyano, nitro, or $OR^{10}$, where $R^{10}$ is alkyl, alkenyl, aryl, or $SR^{11}$, where $R^{11}$ is alkyl, alkenyl, aryl, or $NR^{12}R^{13}$, where $R^{12}$ and $R^{13}$ are independently alkyl, alkenyl, or aryl, or $Z^1$ and $Z^2$ taken together form a ring that is optionally substituted.

Examples of the compounds of the invention are shown in Tables 1 and 2. Data illustrating the ability of these compounds to inhibit RNase P activity and bacterial growth are provided in FIGS. 1–3, 7, and 8.

TABLE 1

Guanylhydrazones

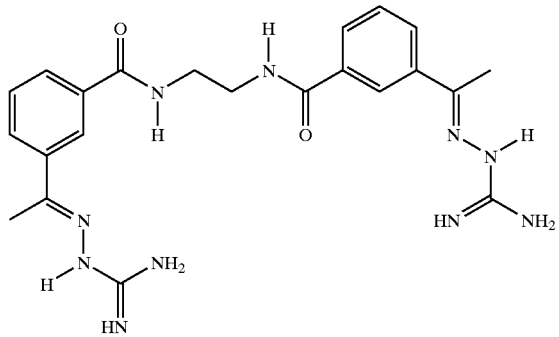

MES 10609

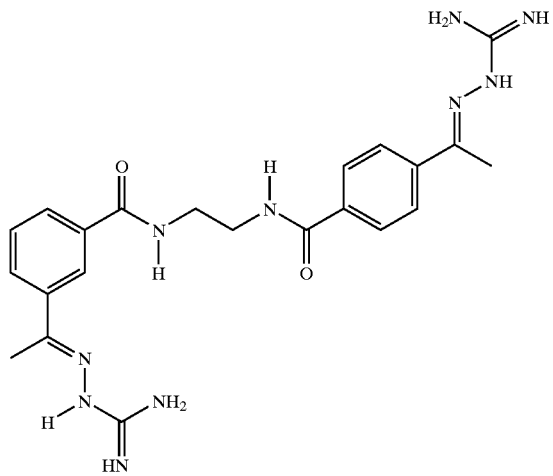

MES 10608

TABLE 1-continued
Guanylhydrazones
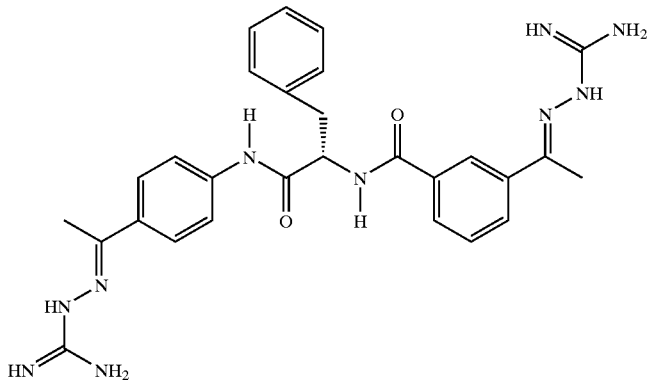
MES 10636
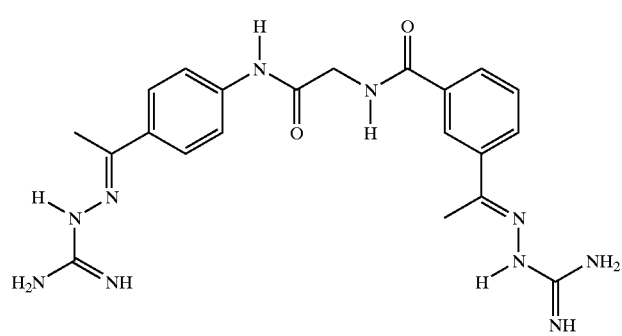
MES 10635
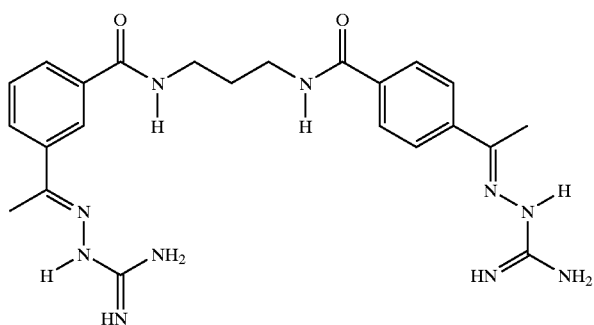
MES 10623
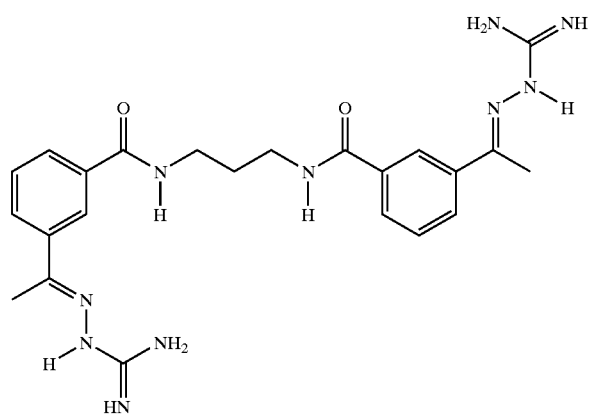

TABLE 1-continued
Guanylhydrazones
MES10624
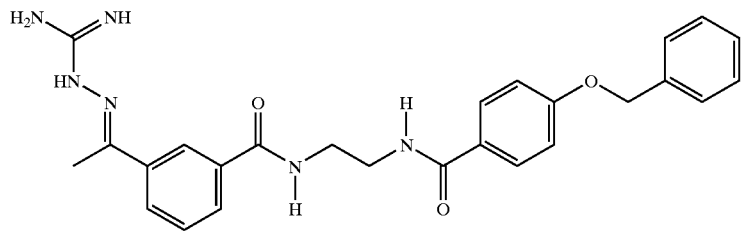
MES 10629
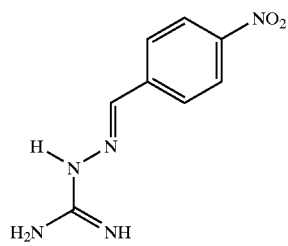
MES32198
TABLE 2
Benzothiazolium compounds
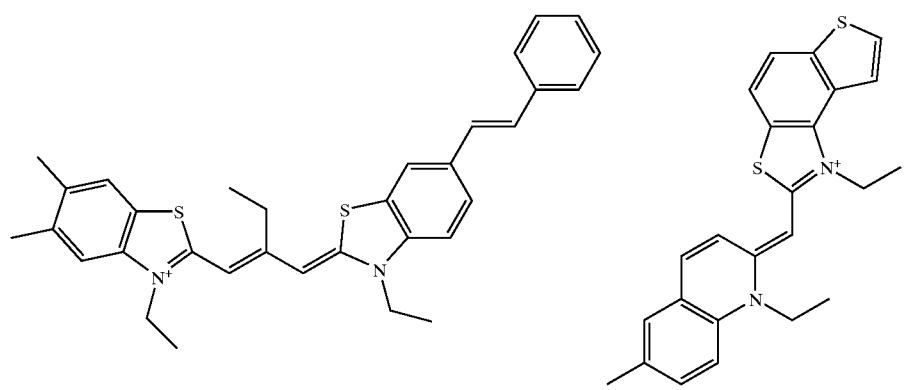
MES 39036  MES 31237

TABLE 2-continued

Benzothiazolium compounds

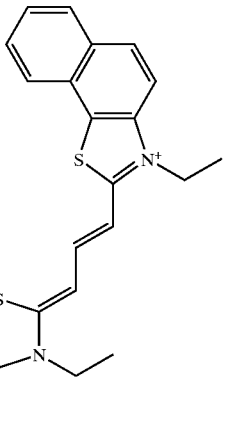

MES 31242

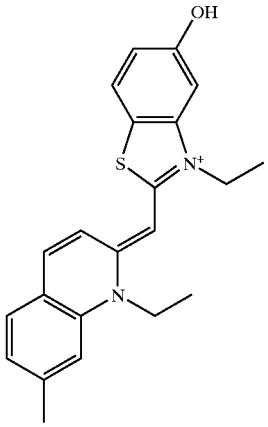

MES 82794

Assays

The ability of compounds of the invention to inhibit RNase P enzymes can be assessed by standard techniques. For example, the cleavage of ptRNA$^{Gln}$ by the enzyme *N. Gonorrhea* RNase P, can be monitored in the presence and absence of a candidate compound as described in the Example 23. The progress of the RNase P-mediated cleavage reaction can be assessed by measuring the fluorescence polarization level of the TAMRA moiety hybridized to the cleaved substrate The ability of compounds of the invention to inhibit bacterial growth can also be assessed by standard testing procedures, such as monitoring bacterial growth in the presence of one or more candidate compound. Any reduction in bacterial growth, in comparison to an uninhibited control, is a measure of the antibacterial activity of the compound. The antibacterial activity of some compounds of the invention were measured against *N. gonorrhea*, *E. coli*, *S. aureus*, and *S. pyogenes* (Example 23).

Clinical Applications of RNase P Inhibitors

Compounds which modulate RNase P activity may be administered by any appropriate route for treatment, stabilization, or prevention of a bacterial infection. These compounds may be administered to humans, domestic pets, livestock, or other animals with a pharmaceutically acceptable diluent, carrier, or excipient, in unit dosage form. Administration may be oral, topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or by any other suitable route of administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington: The Science and Practice of Pharmacy* (20th ed., A. R. Gennaro ed., Lippincott: Philadelphia, 2000). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid, phosphoric acid, or the like. Metal complexes include zinc, iron, and the like.

The chemical compounds for use in such therapies may be produced and isolated as described herein or by any standard technique known to those in the field of medicinal chemistry. Conventional pharmaceutical practice may be employed to provide suitable formulations or compositions to administer the identified compound to patients suffering from a condition or at increased risk for a condition involving bacterial infection. Administration may begin before, during, or after the patient is symptomatic.

The formulations can be administered to human patients in therapeutically effective amounts (e.g., amounts which prevent, stabilize, eliminate, or reduce a bacterial infection) to provide therapy for a disease or condition associated with a bacterial infection. Typical dose ranges are from about 0.1 µg/kg to about 1 mg/kg of body weight per day. The exemplary dosage of drug to be administered is likely to depend on such variables as the type and extent of the disorder, the overall health status of the particular patient, the formulation of the compound, and its route of administration. Standard clinical trials maybe used to optimize the dose and dosing frequency for any particular compound.

Other Uses of RNase P Inhibitors

Compounds which modulate RNase P activity may also be used for the preservation of food, beverages, cosmetics such as lotions, creams, gels, ointments, soaps, shampoos, conditioners, antiperspirants, deodorants, mouth wash, contact lens products, enzyme formulations, or food ingredients. Methods for use as a preservative include incorporating a compound of the invention into, for example, unpreserved food, beverages, cosmetics, contact lens products, or food ingredients in an amount effective for killing or inhibiting the growth of bacteria.

Thus, a compound of the invention may by useful as a disinfectant, e.g., in the treatment of acne, eye infections, mouth infections, skin infections, or other wounds. It is also contemplated that a compound of the invention is useful for cleaning, disinfecting, or inhibiting bacterial growth on any hard surface. Examples of surfaces which may advantageously be contacted with a compound of the invention are surfaces of process equipment used in dairies, chemical or pharmaceutical process plants, water sanitation systems, paper pulp processing plants, water treatment plants, cooling towers, cooking utensils, hospital operating rooms, or surfaces in any area in which food is prepared (e.g., hospitals, nursing homes, or restaurants). The composition of the invention should be used in an amount which is effective for cleaning, disinfecting, or inhibiting bacterial growth on the relevant surface.

In addition, compounds of the invention are useful for cleaning, disinfecting, or inhibiting bacterial growth on in an in-dwelling device in a patient. In-dwelling devices include, but are not limited to, surgical implants, prosthetic devices, artificial joints, heart valves, pacemakers, vascular grafts, vascular catheters, cerebrospinal fluid shunts, urinary catheters, and continuous ambulatory peritoneal dialysis (CAPD) catheters. A compound of the invention may be used to bathe an in-dwelling device immediately before insertion. The compound will desirably be present, for example, at a concentration of 1 µg/ml to 10 mg/ml for bathing of wounds or indwelling devices. Alternatively, the compound may be administered by injection to achieve a local or systemic effect against relevant bacteria shortly before insertion of an in-dwelling device. Treatment may be continued after surgery during the in-body time of the device.

The following examples are provided to illustrate the invention. These examples should not be construed as limiting.

EXAMPLE 1

General Synthetic Strategy

General Description of the Synthesis of Guanylhydrazines and Aryl Guanylhydrazones, Precursors for Compounds of Formulas II, IX, and X:

Guanylhydrazines can be prepared from commercially available starting materials as follows. A monoprotected hydrazine (e.g., t-butylcarbazate—Aldrich catalogue number B9, 100-5) may be condensed with an aldehyde/ketone and reduced with a hydride reducing agent such as sodium cyanoborohydride to yield a protected monoalkylated hydrazine. Condensation with a suitable guanylating agent such as 1,3-bis(t-butoxycarbonyl)-2-methyl-2-thiopseudourea (Aldrich catalogue number 43,9910-8) or a derivative of this compound (see, for example, Monache et al., J. Med. Chem. 36: 2956, 1993) yields mono or di substituted guanylhydrazines, as shown in Scheme 1. In this Scheme, $R^a$ is $R^3$ of formula II, $R^7$ of formula IX, $R^3$ of formula X, or $R^{46}$ of formula XVII; $R^b$ is $R^5$ of formula II, $R^4$ of formula IX, $R^4$ of formula X, or $R^{48}$ of formula XVII; and $R^c$ is $R^4$ of formula II, $R^3$ of formula IX, $R^7$ of formula X, or $R^{47}$ of formula XVII.

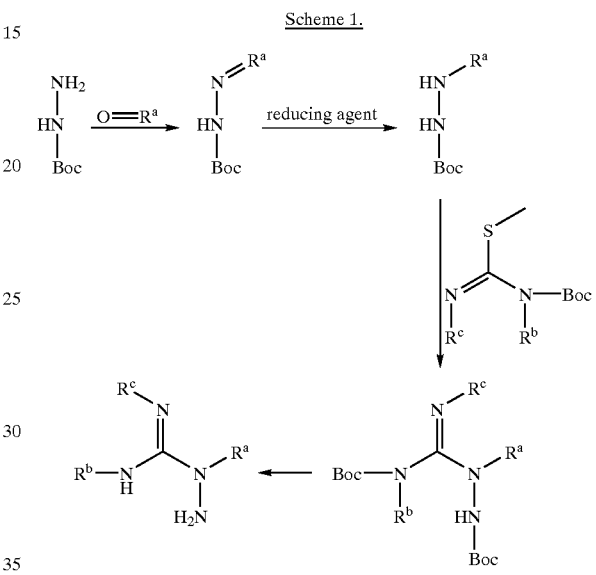

Phenyl, biphenyl and napthyl guanylhydrazones of formulas II, IX, and X can be prepared by condensation of guanylhydrazines with aryl aldehydes or ketones as shown in Scheme 2. $R^d$ is $R^6$ of formulas II, IX, or X, or $R^{49}$ of formula XIV.

The "aryl" group may be a phenyl, biphenyl, or napthyl group, which also contains at least one carboxylic acid or amino substituent useful for attachment to linker A. The reaction is carried out using standard imine condensation techniques (see, for example, J. March, Advanced Organic Chemistry: Reactions, Mechanisms and Structure, Wiley: New York, pp. 896–899, 1992). The condensation reaction may be performed prior to the coupling to linker A or after the coupling to linker A. Accordingly, the guanyl nitrogens of the guanyl hydrazine may be protected (for example, using standard protecting groups, R=Boc or Cbz) or unprotected, during the condensation reaction of Scheme 1.

Alternatively, the bis aldehyde/ketones can be condensed with a monosubstituted hydrazine to generate the bis hydrazones which may be subsequently guanylated employing the reagent described above, as shown in Scheme 3.

Scheme 3.

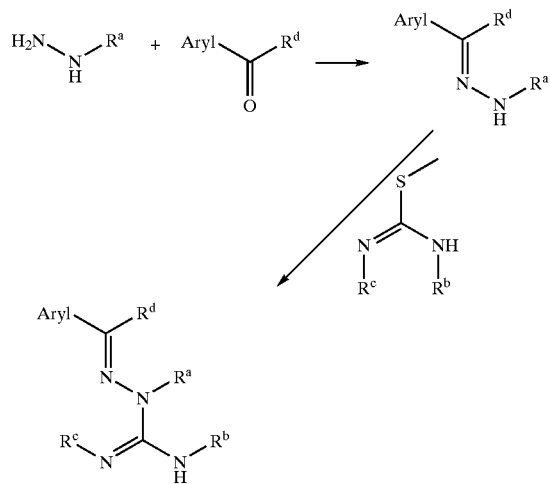

General Description of the Synthesis of Aryl Amidines, Precursors for Compounds of Formulas III, VI, and VIII:

Phenyl, biphenyl, and napthyl amidines of formulas III, VI, and VIII can be prepared from their respective nitrile precursors. The precursor nitrile substituted biphenyl carboxylic acids are available through methods previously described in the art (see, for example, Gong et al., Synlett. 6: 829, 2000; Baudoin et al., J. Org. Chem. 65: 9268, 2000; and Neustadt et al., Bioorg. & Med. Chem. 8: 2395, 1998). The precursor cyanonapthoic acids may be prepared according to the methods of Adcock et al. (Aust. J. Chem. 18: 1351, 1965). The precursor nitrilobenzoic acids are commercially available. For example, 3-cyanobenzoic acid (catalogue number 15,716-3) and 4-cyanobenzoic acid (catalogue number C8,980-3) can be purchased from Aldrich. The precursor nitrile substituted aryl amines are available through methods previously described in the art (see, for example, Neilson in Patai, *The Chemistry of Amidines and Imidates*, Wiley: Noe York, pp. 385–489, 1975; or Rousselet et al. Tetrahedron Lett. 34: 6395, 1993).

The conversion of nitrile groups to amidines can be accomplished using standard synthetic protocols. For example, the classical Pinner reaction (see Pinner, A. *Die Iminoäther und ihre Derivate*, Verlag, R. Oppenheim: Berlin, 1892; or Roger et al. Chem. Rev. 61: 179, 1961) is a commonly used method for the transformation of nitrites to amidines. The direct conversion of nitrites to amidines can be achieved under milder conditions with the use of alkylchloroaluminum amides (Garigipati Tetrahedron Lett. 31: 1969, 1990; and Moss et al., Tetrahedron Lett. 36: 8761, 1995); with the addition of a copper(I) catalyst (Rousselet et al. Tetrahedron Lett. 34: 6395, 1993); or with the addition of a lanthanide(III) catalyst (Forsberg et al., J. Org. Chem. 52: 1017, 1987). In addition, the conversion can be achieved via an intermediate such as an oxime (Judkins et al., Synth. Commun. 26: 4351, 1996) or a thioimidate (Baati et al. Synlett 92, 1999; and Schnur J. Org. Chem. 44: 3726, 1979).

General Description of the Synthesis of Aryl Guanidines, Precursors of Compounds of Formulas IV, V, and VII Phenyl, biphenyl and napthyl guanidines of formulas IV, V, and VII can be prepared from their respective amine precursors. The precursor amine substituted biphenyl carboxylic acids are available through methods previously described in the art (see, for example, Gong et al., Synlett. 6: 829, 2000; Nesloney et al., J. Org. Chem. 61: 3127, 1996; Baudoin et al., J. Org. Chem. 65: 9268, 2000; and Neustadt et al., *Bioorg. & Med. Chem.* 8: 2395, 1998). The precursor aminonapthoic acids may be prepared according to the methods of Adcock et al. (Aust. J. Chem. 18: 1351, 1965). The precursor aminobenzoic acids are commercially available. For example, anthranilic acid (catalogue number A8,985-5), 3-aminobenzoic acid (catalogue number 12,767-1) and 4-aminobenzoic acid (catalogue number 42,976-7) can be purchased from Aldrich.

Amino-aryl-guanidines may be prepared from the corresponding nitroanilines. Guanylation of the nitroaniline followed by hydrogenation of the nitro functionality would generate the desired amino-aryl-guanidines. These compounds could be coupled directly to the activated carboxylic acids or the guanidine group could be protected prior to hydrogenation to yield the protected amino-aryl-guanidines.

The conversion of amino groups to guanidines can be accomplished using standard synthetic protocols. For example, Mosher has described a general method for preparing mono-substituted guanidines by reaction of aminoiminomethanesulfonic acid with amines (Kim, K.; Lin, Y.-T.; Mosher, H. S. Tetrahedron Lett. 29: 3183, 1988). A more convenient method for guanylation of primary and secondary amines was developed by Bernatowicz employing 1-H-pyrazole-1-carboxamidine hydrochloride; 1-H-pyrazole-1-(N,N'-bis(tert-butoxycarbonyl)carboxamidine; or 1-H-pyrazole-1-(N,N'-bis(benzyloxycarbonyl) carboxamidine. These reagents react with amines to give mono-substituted guanidines (see Bernatowicz et al., J. Org. Chem. 57: 2497, 1992; and Bernatowicz et al., Tetrahedron Lett.34: 3389, 1993). In addition, thioureas and S-alkyl-isothioureas have been shown to be useful intermediates in the syntheses of substituted guanidines (Poss et al., Tetrahedron Lett. 33: 5933 1992).

General Description of the Coupling of Precursors to Linker A, Synthesis of Compounds of Formulas II–X:

A general scheme for the synthesis of compounds having formulas II through X, employing standard amide coupling (see, for example, J. March, *Advanced Organic Chemistry: Reactions, Mechanisms and Structure*, (Wiley: New York, pp. 417–425, 1992)) is shown in Scheme 4. Compounds of formula I Scheme 4.

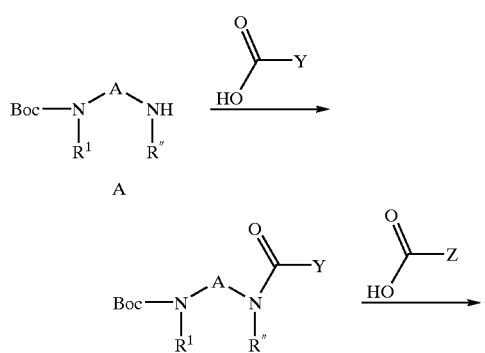

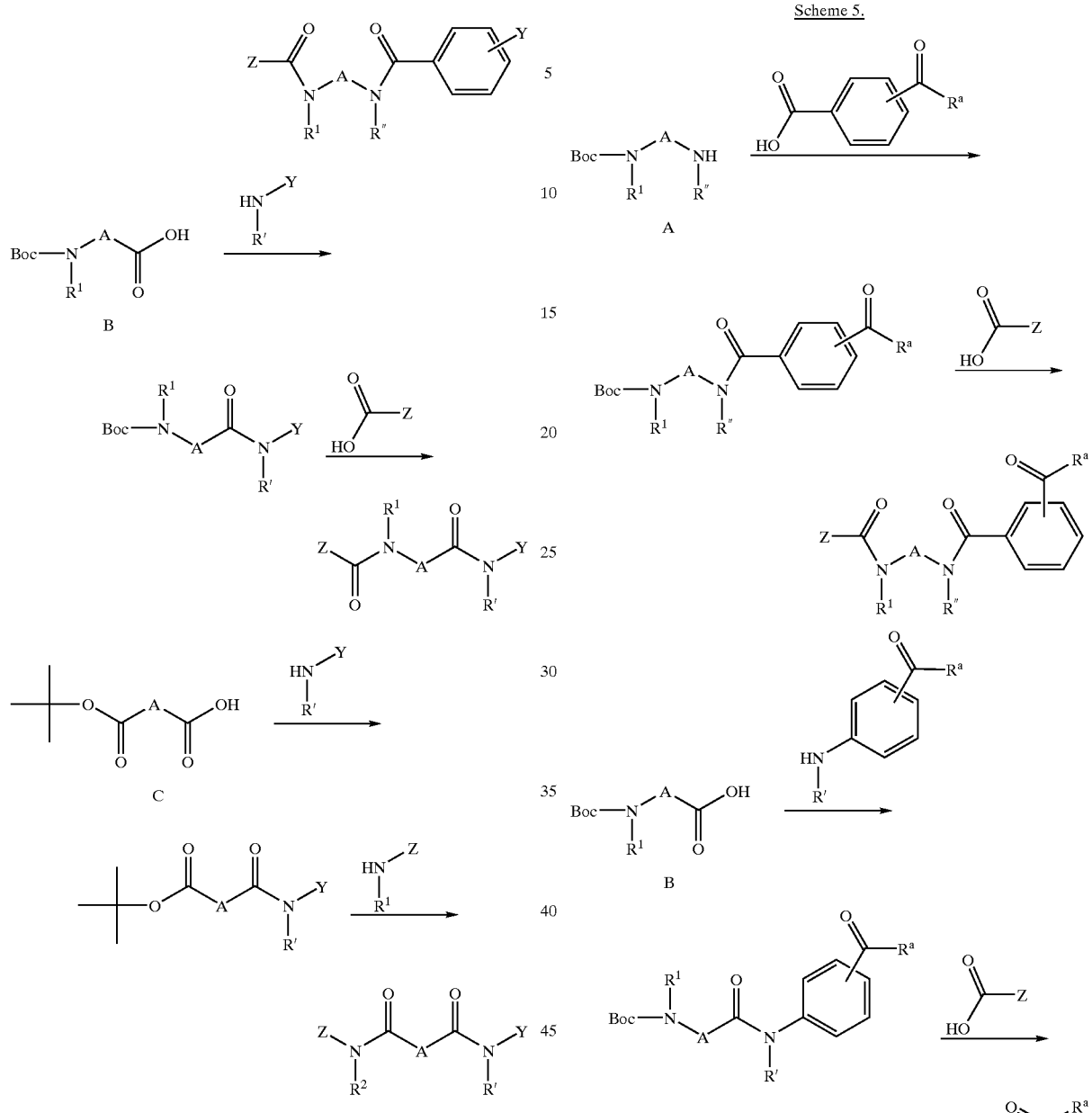

in which Y and Z are as described herein can be prepared by selective protection and deprotection of amine and carboxylic acid functional groups attached to linker A, as shown in Scheme 4 with starting materials A, B, and C. For example, commonly used protecting groups for amines include tert-butoxycarbonyl (Boc) and benzyloxycarbonyl (Cbz) groups. Examples of commonly used protecting groups for carboxylic acids include methyl ester, ethyl ester, and tert-butyl ester.

In the case where Y and/or Z is a guanidyl hydrazone in the final product (a compound of formula II, IX, or X), the coupling may proceed with the precursor aldehyde or ketone as shown in Scheme 5 (where $R^a$ is $R^3$ of formula II, $R^7$ of formula IX, $R^3$ of formula X, or $R^{46}$ of formula XVII). The product of the coupling reactions of Scheme 5 may then be combined with a guanyl hydrazine, in a condensation reaction of Scheme 2, resulting in the formation of a guanyl hydrazone of formula II, IX, or X.

-continued

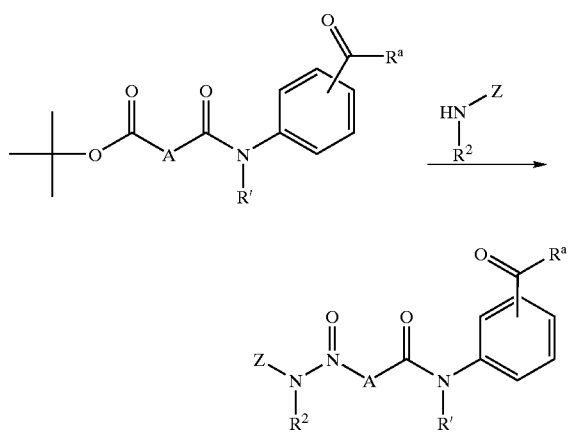

EXAMPLE 2

Synthesis of N-(N'-t-butoxycarbonyl-2-aminoethyl)-3-acetylbenzamide, Compound 1 of Scheme 6

N-(t-Butoxycarbonyl)ethylenediamine 2 (5 mmol, 800 mg) was weighed directly into a clean dry flask, which was then tightly stoppered. 3-Acetylbenzoic acid 3 (5 mmol, 820 mg) was added directly to the amine in the flask. Under an inert atmosphere dry dimethylformamide (15 mL) was added to the flask. Benzotriazole-1-yl-oxy-tris-(dimethylamino)-phosphonium hexafluorophosphate (5 mmol, 2.21 g) was added to the solution, and subsequently N-methylmorpholine (15 mmol, 1.51 g, 1.7 mL) was added to the solution, and the mixture was allowed to stir for 2–3 hrs. The reaction mixture was quenched by the addition of 15 mL of water to the reaction flask, and partitioned between water (300 mL) and ethyl acetate (300 mL). The organic phase was washed successively with saturated sodium bicarbonate (200 mL), water (4×300 mL), and brine (200 mL) and then dried over anhydrous sodium sulfate. Filtering off the drying agent and concentration of the organic phase to ~10–15 mL yielded a tan solid. Hexanes (~30 mL) were added and the mixture gently heated to reflux. Upon cooling semicrystalline product was precipitated as a white powder. The product was collected by filtration and dried. Yield 775 mg, 51%.

EXAMPLE 3

Synthesis of N-(N'-2-(3-acetylbenzamido)-ethyl)-3-acetylbenzamide, Compound 4 of Scheme 6

N-(N'-t-butoxycarbonyl-2-aminoethyl)-3-acetylbenzamide 1 (0.5 mmol) was dissolved in a 50/50 mixture of dichloromethane and trifluoroacetic acid (2 mL) and stirred for 30 minutes. After which time the volatiles were removed on the rotary evaporator and toluene (4 mL) was added to the flask. The volatiles were again removed, and the residue was further dried under high vacuum for 5 min. The oily residue was dissolved in dimethylformamide (1.5 mL) and to this added benzotriazole-1-yl-oxy-tris-(dimethylamino)-phosphonium hexafluoro-phosphate (1.0 eq., 221 mg) and 3-acetylbenzoic acid 3 (1.0 eq, 83 mg), and N-methylmorpholine (4.0 eq., 202 mg, 220 μL), and the resulting mixture was stirred overnight. The reaction mixture was quenched by the addition of 1.5 mL of water to the reaction flask, and partitioned between water (30 mL) and ethyl acetate (30 mL). The organic phase was washed successively with saturated sodium bicarbonate (20 mL), water (4×30 mL), and brine (20 mL) and then dried over anhydrous sodium sulfate. Filtering off the drying agent and concentration of the organic phase to ~1–1.5 mL yielded a tan solid. Hexanes (~30 mL) were added and the mixture gently heated to reflux. Upon cooling semicrystalline product was precipitated as a tan powder. The product was collected by filtration and dried. Yield 159 mg, 90%.

EXAMPLE 4

Synthesis of Bisguanylhydrazones of N-(N'-2-(3-acetylbenzamido)-ethyl)-3-acetylbenzamide, MES 10609

The bisguanylhydrazone of N-(N'-2-(3-acetylbenzamido)-ethyl)-3-acetylbenzamide, MES 10609, was prepared as described in scheme 6. N-(N'-2-(3-acetylbenzamido)-ethyl)-3-acetylbenzamide 4 (0.2 mmol, 70 mg) was dissolved in dry DMSO (1 mL) and to this solution added anhydrous ethanol (672 μL), aminoguanidine hydrochloride (3 eq., 0.6 mmol, 66 mg), and hydrochloric acid (20 mol %, 320 μL of a 99:1 mixture of EtOH:HCl (conc.)). The reaction mixture was heated to ~100° C. in a sealed vial for 5 days. After which time the vial was removed from the heat bath and allowed to cool. The cap was removed, and the ethanol allowed to evaporate at ~90° C. for 45 min. The crude reaction product was quenched with 0.2 N NaOH(aq) (10 mL) and allowed to stir for 3 hrs. The resulting white precipitate was collected by filtration and washed with water (2×1 mL) and dried under vacuum overnight. The resultant dry solid was added to 0.025 N HCl(aq) (20 mL) and allowed to stand for 30 min. The solution was filtered to remove insoluble particulates and frozen. Lyophilization gave a feathery white solid which was one peak by HPLC (Rt=6 min: water(58%), 1% trifluoroacid acid in water(17%), acetonitrile(25%)).

EXAMPLE 5

Synthesis of Bisguanylhydrazones of N-(N'-2-(4-acetylbenzamido)-ethyl)-3-acetylbenzamide, MES 10608

Bisguanylhydrazones of N-(N'-2-(4-acetylbenzamido)-ethyl)-3-acetylbenzamide, MES 10608, can be prepared in an analogous manner to Example 4, as shown below in scheme 7.

Scheme 6.
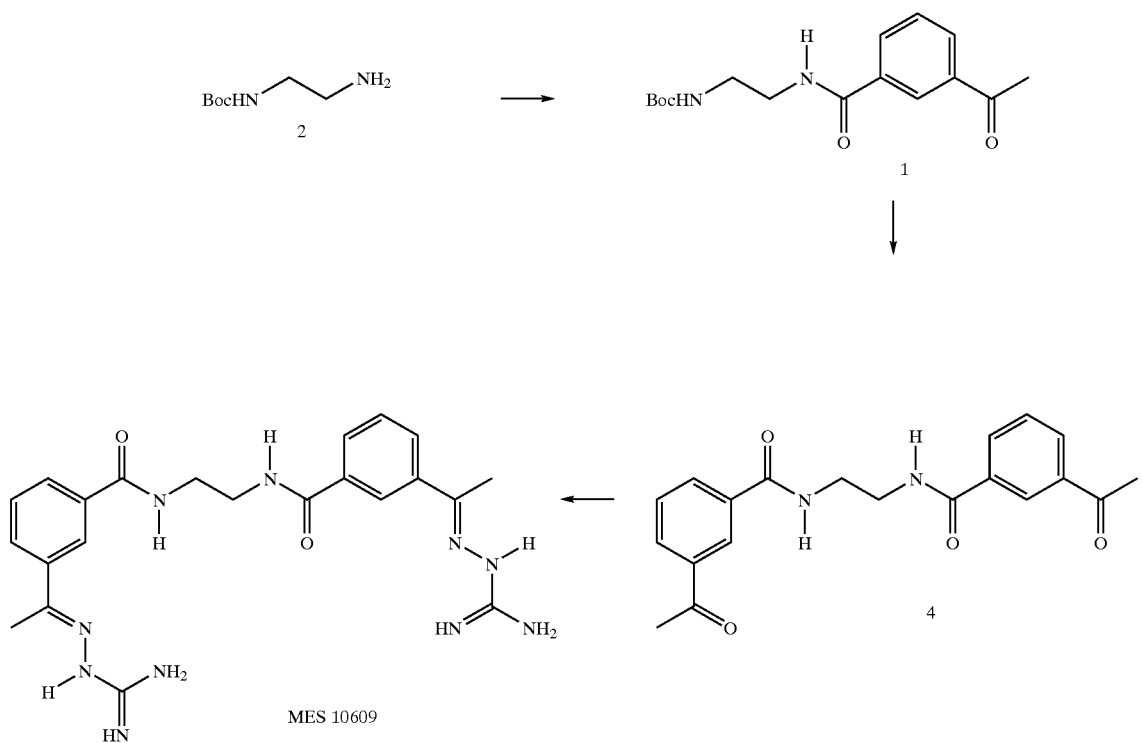
Scheme 7.
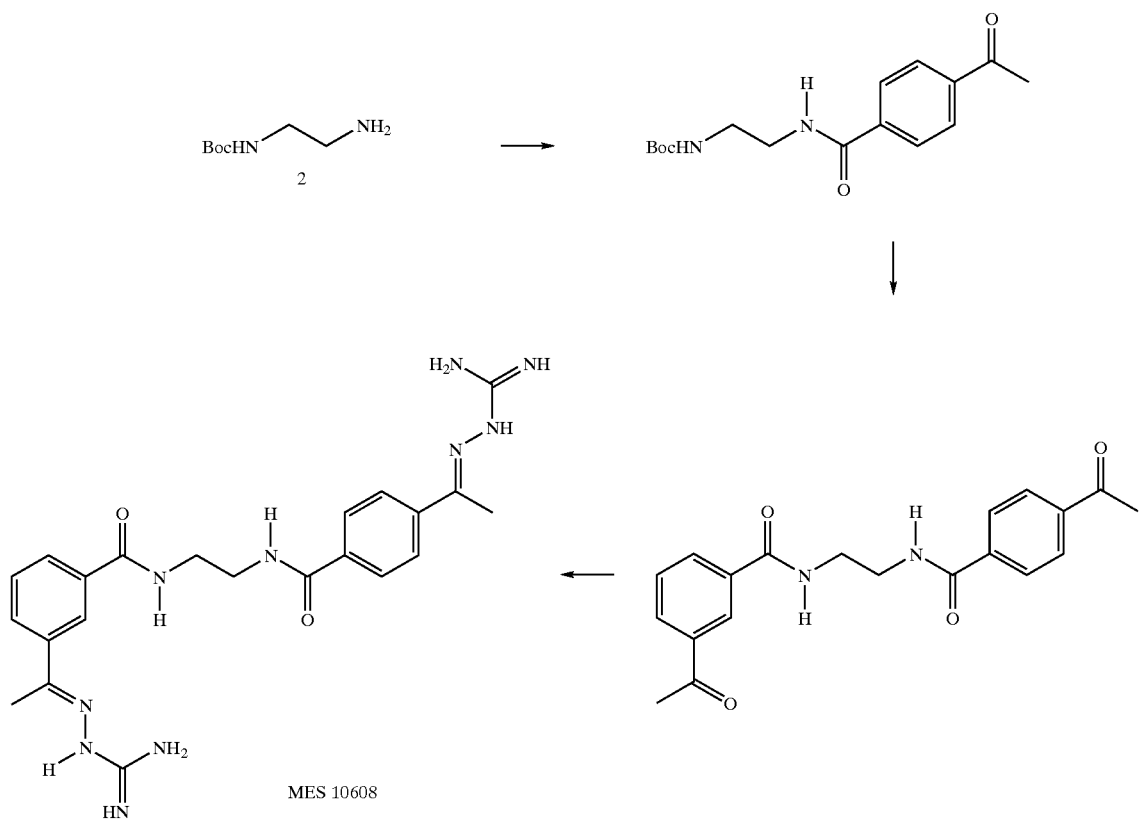

EXAMPLE 6

Synthesis of N'-(t-butoxycarbonyl)-N-(4-acetylphenyl)glycinamide, Compound 1 of Scheme 8

N-(t-Butoxycarbonyl)glycine 2 (1 mmol, 175 mg) was weighed directly into the clean dry flask, 4-aminoacetophenone 3 (1 mmol, 135 mg) was added directly to the acid in the flask. Under an inert atmosphere dry dimethylformamide (5 mL) was added to the flask. Benzotriazole-1-yl-oxy-tris-(dimethylamino)-phosphoniumhexafluorophosphate (1 mmol, 442 mg) was added to the solution, and subsequently ethyldiisopropylamine (3.1 mmol, 404 mg, 0.44 mL) was added to the solution and the mixture was allowed to stir for 72 hrs. The reaction mixture was quenched by the addition of 60 mL of 0.2 N aqueous sodium hydroxide to the reaction flask. After stirring for 2 hr the mixture was extracted with ethyl acetate (60 mL). The organic phase was washed successively with water (4×40 mL), and brine (30 mL) and then dried over anhydrous sodium sulfate. Filtering off the drying agent and flask. The volatiles were again removed, and the residue was further dried under high vacuum for 5 min. The oily residue was dissolved in dimethylformamide (2 mL) and to this added benzotriazole-1-yl-oxy-tris-(dimethylamino)-phosphonium hexafluoro-phosphate (1.0 eq., 88 mg) and 3-acetylbenzoic acid 3 (1.0 eq., 32.5 mg), and ethyldiisopropylamine (3.1 eq., 80 mg, 88 µL), and the resulting mixture was stirred overnight. The reaction mixture was quenched by the addition of 0.2 N aqueous sodium hydroxide (12 mL) to the reaction flask, and the mixture was stirred for 3 hr. The resulting mixture was diluted with water (10 mL) and extracted with ethyl acetate (20 mL). The organic phase was washed successively with water (4×20 mL), and then dried over anhydrous sodium sulfate. Filtering off the drying agent and concentration of the organic phase to ~1–1.5 mL yielded a cream solid. Hexanes (~30 mL) were added and the mixture gently heated to reflux. Upon cooling semicrystalline product was precipitated as a cream powder. The product was collected by filtration and dried. Yield 18 mg, 27%.

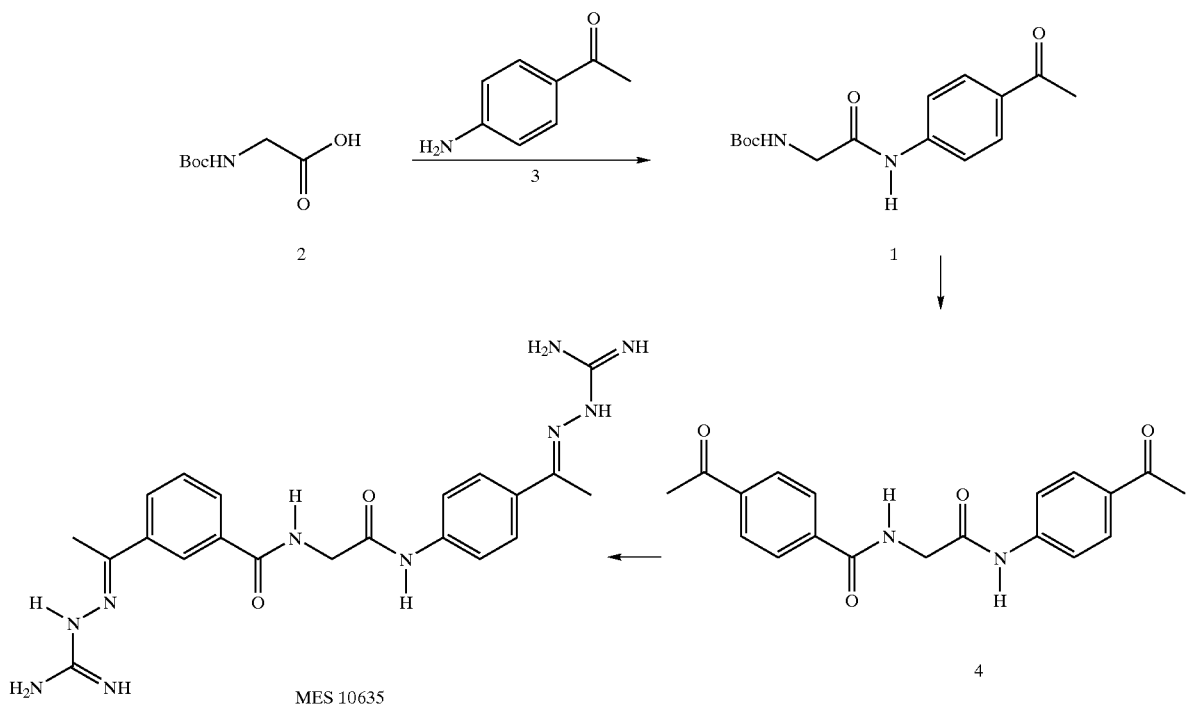

Scheme 8.

MES 10635 concentration of the organic phase to ~10–15 mL yielded a white solid product. The desired material was isolated by column chromatography on silica gel eluted with Hex-:EtOAc (2:1-1:1). Yield 85 mg, 29%.

EXAMPLE 7

Synthesis of N'-(3-acetylbenzoyl)-N-(4-acetylphenyl)glycinamide, Compound 4 of Scheme 8

N'-(t-butoxycarbonyl)-N-(4-acetylphenyl)glycinamide 1 (58 mg, 0.2 mmol) was dissolved in a 50/50 mixture of dichloromethane and trifluoroacetic acid (2 mL) and stirred for 45 min. After which time the volatiles were removed on the rotary evaporator and toluene (4 mL) was added to the

EXAMPLE 8

Synthesis of Bisguanylhydrazone trifluoroacetic acid salt of N'-(3-acetylbenzoyl)-N-(4-acetylphenyl)glycinamide MES 10635

N'-(3-acetylbenzoyl)-N-(4-acetylphenyl)glycinamide 4 (0.053 mmol, 18 mg) was dissolved in dry DMSO (0.25 mL) and to this solution added anhydrous ethanol (168 µL), aminoguanidine hydrochloride (3 eq., 0.159 mmol, 18 mg), and hydrochloric acid (20 mol %, 80 µL of a 99:1 mixture of EtOH:HCl (conc.)). The reaction mixture was heated to ~100° C. in a sealed vial for 5 days. After which time the vial was removed from the heat bath and allowed to cool. The cap was removed and the ethanol allowed to evaporate at ~90° C. for 45 min. The crude reaction product was purified by C18 semi-preparative (200 mm×25 mm) HPLC eluted with acetonitrile:water:1% TFA in water (18:62:20). A major fraction eluted with a retention time of 7.5 min. and was collected. Removal of the volatile acetonitrile and subsequent lyophilization gave a feathery white solid (16 mg, 67%) which was one peak by HPLC (Rt=7.5 min: acetonitrile(25), water(62%), 1% trifluoroacid acid in water (20%)).

EXAMPLE 9

Synthesis of Bisguanylhydrazone trifluoroacetic acid salt of N'-(3-acetylbenzoyl)-N-(4-acetylphenyl) phenylalaninamide, MES 10636

MES 10636 was prepared in an analogous manner to that shown above in Example 8, employing N-(t-Butoxycarbonyl)phenylalanine instead of N-(t-Butoxycarbonyl)glycine.

EXAMPLE 10

Benzothiazolium Salts Identified from Combinatorial Libraries

The compound, MES 35793, is available from the Nanoscale Combinatorial Synthesis Inc. library (Compound Identification Number: NS19466) and has the structure:

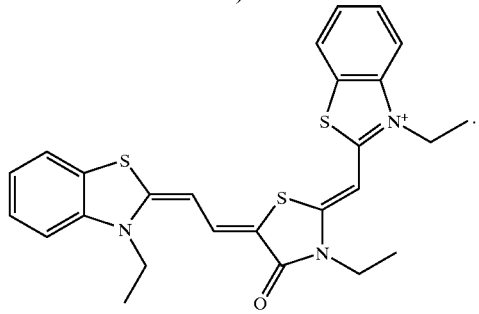

The compound, MES 31242, is available from the Nanoscale Combinatorial Synthesis Inc. library (Compound Identification Number: NS2194) and has the structure:

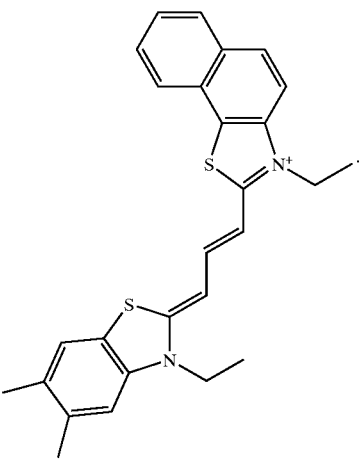

The compound, MES 82794, is available from Specs, Inc. (Compound Identification Number: AG-690/15428507) and has the structure:

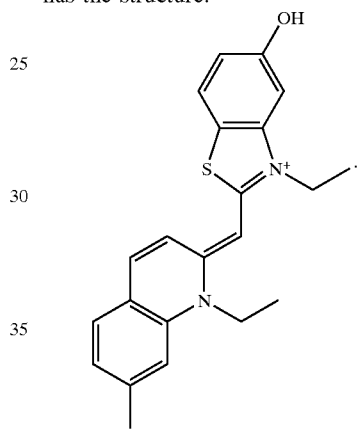

Other benzothiazolium salts may be synthesized using methods known in the art.

EXAMPLE 11

Synthesis of Mono Guanylhydrazones

Mono guanylhydrazones of the invention may be synthesized according to Scheme 9.

Scheme 9.

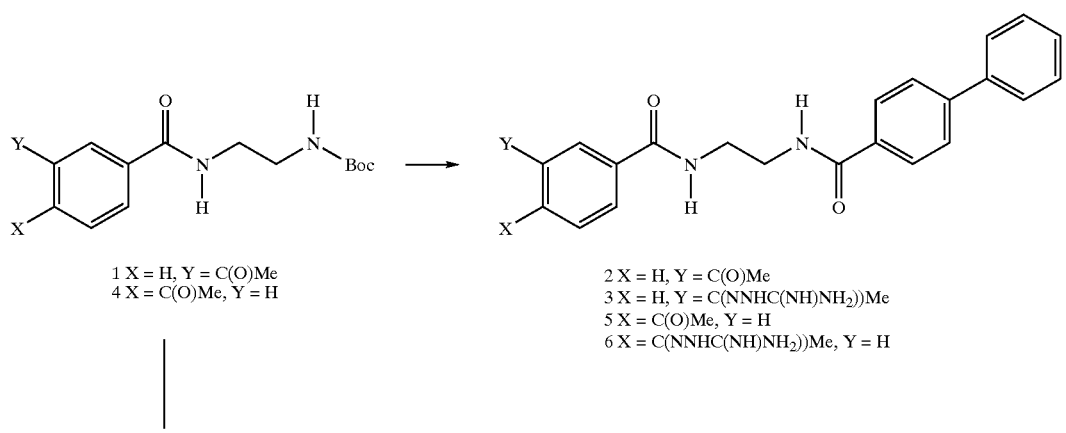

1 X = H, Y = C(O)Me
4 X = C(O)Me, Y = H

2 X = H, Y = C(O)Me
3 X = H, Y = C(NNHC(NH)NH$_2$))Me
5 X = C(O)Me, Y = H
6 X = C(NNHC(NH)NH$_2$))Me, Y = H

-continued

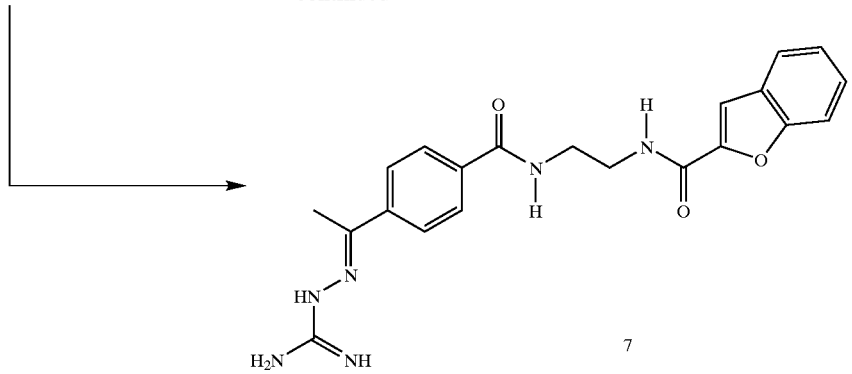

EXAMPLE 12

Synthesis of N-(N'-2-(3-acetylbenzamido)-ethyl)-4-phenylbenzamide, Compound 2 of Scheme 9

N-(N'-t-butoxycarbonyl-2-aminoethyl)-3-acetylbenzamide 1 (0.17 mmol) was dissolved in a 50/50 mixture of dichloromethane and trifluoroacetic acid (2 mL) and stirred for 30 min. After which time the volatiles were removed on the rotary evaporator, and toluene (4 mL) was added to the flask. The volatiles were again removed, and the residue was further dried under high vacuum for 5 min. The oily residue was dissolved in dimethylformamide (1 mL) and to this added benzotriazole-1-yl-oxy-tris-(dimethylamino)-phosphonium hexafluoro-phosphate (1.0 eq., 68 mg) and 4-phenylbenzoic acid (1.2 eq., 40 mg), and N-methylmorpholine (4.0 eq., 62 mg, 68 µL), and the resulting mixture was stirred overnight. The reaction mixture was quenched by the addition of 6 mL of a 0.2 N aqueous sodium hydroxide solution. The resulting mixture was stirred for 1 hr. The product was collected by filtration, washed with water (2×3 mL) and dried. Yield 32 mg, 49%.

EXAMPLE 13

Synthesis of the mono guanylhydrazone 3 of N-(N'-2-(3-acetylbenzamido)-ethyl)-4-phenylbenzamide, MES 10725

The guanylhydrazone of N-(N'-2-(3-acetylbenzamido)-ethyl)-4-phenylbenzamide, MES 10725, was prepared as described in Scheme 9. N-(N'-2-(3-acetylbenzamido)-ethyl)-4-phenylbenzamide 2 (0.08 mmol, 32 mg) was dissolved in dry DMSO (0.2 mL) and to this solution added anhydrous ethanol (133 µL), aminoguanidine hydrochloride (3 eq., 0.24 mmol, 28 mg), and hydrochloric acid (20 mol %, 70 µL of a 99:1 mixture of EtOH:HCl (conc.)). The reaction mixture was heated to ~105° C. in a sealed vial for 5 days. After which time the vial was removed from the heat bath and allowed to cool. The cap was removed and the ethanol allowed to evaporate at ~90° C. for 45 min. The crude reaction product was purified by preparative reverse-phase HPLC. Lyophilization gave a feathery white solid, 3 which was one peak by HPLC (water(58%), 1% trifluoroacid acid in water(17%), acetonitrile(25%)). 1H NMR (D$_2$O) δ=10.78 (s, 1H), 8.92(s, 1H), 8.84 (s,1H), 8.44 (s, 1H), 8.32 (d, J=8 Hz, 1H), 8.29 (s, 1H), 8.06 (m, 2H), 7.36–7.99 (m, 10H), 3.67 (s, 4H), 2.56 (s, 3H) ppm.

EXAMPLE 14

Synthesis of N-(N'-2-(4-acetylbenzamido)-ethyl)-4-phenylbenzamide, compound 4 of Scheme 9

N-(N'-t-butoxycarbonyl-2-aminoethyl)-4-acetylbenzamide 5 (0.17 mmol) was dissolved in a 50/50 mixture of dichloromethane and trifluoroacetic acid (2 mL) and stirred for 30 min. After which time the volatiles were removed on the rotary evaporator, and toluene (4 mL) was added to the flask. The volatiles were again removed, and the residue was further dried under high vacuum for 5 min. The oily residue was dissolved in dimethylformamide (1 mL) and to this added benzotriazole-1-yl-oxy-tris-(dimethylamino)-phosphonium hexafluoro-phosphate (1.0 eq., 68 mg) and 4-phenylbenzoic acid, (1.2 eq, 40 mg), and N-methylmorpholine (4.0 eq., 62 mg, 68 µL), and the resulting mixture was stirred overnight. The reaction mixture was quenched by the addition of 6 mL of a 0.2 N aqueous sodium hydroxide solution. The resulting mixture was stirred for 1 hr. The product was collected by filtration, washed with water (2×3 mL) and dried. Yield 45 mg, 69%.

EXAMPLE 15

Synthesis of the mono guanylhydrazone 6 of N-(N'-2-(4-acetylbenzamido)-ethyl)-4-phenylbenzamide, MES 10732

The guanylhydrazone of N-(N'-2-(3-acetylbenzamido)-ethyl)-4-phenylbenzamide 6, MES 10725, was prepared as described in scheme 9. N-(N'-2-(3-acetylbenzamido)-ethyl)-4-phenylbenzamide 1 (0.12 mmol, 45 mg) was dissolved in dry DMSO (0.25 mL) and to this solution added anhydrous ethanol (188 µL), aminoguanidine hydrochloride (2.2 eq., 0.26 mmol, 29 mg), and hydrochloric acid (20 mol %, 110 µL of a 99:1 mixture of EtOH:HCl (conc.)). The reaction mixture was heated to ~105° C. in a sealed vial for 5 days. After which time the vial was removed from the heat bath and allowed to cool. The cap was removed and the ethanol allowed to evaporate at ~90° C. for 45 min. The crude reaction product was purified by preparative reverse-phase HPLC. Lyophilization gave a feathery white solid which was one peak by HPLC (water(58%), 1% trifluoroacid acid in water(17%), acetonitrile(25%)). 1H NMR (DMSO) δ=10.55 (s, 1H), 8.71 (m, 2H), 7.4–8.1 (m, 13H), 3.48 (s, 2H), 3.35 (s, 2H), 2.28 (s, 3H) ppm.

EXAMPLE 16

Synthesis of the mono guanylhydrazone 7 of N-(N'-2-(3-acetylbenzamido)-ethyl)benzofuran-2-carboxamide, MES 10716

This compound can be prepared from N-(N'-t-butoxycarbonyl-2-aminoethyl)-3-acetylbenzamide 1 in a manner analogous to Examples 13 and 15 employing benzofuran-2-carboxylic acid in place of 4-phenylbenzoic acid. 1H NMR (DMSO) δ=10.45 (s, 1H), 8.90 (s, 1H), 8.70 (s, 2H), 8.19 (d, J=8 Hz, 1H), 7.9 (d, J=8 Hz, 1H), 7.80 (d, J=8 Hz, 1H), 7.63 (d, J=8 Hz, 1H), 7.56 (d, J=8 Hz, 1H), 7.54 (s, 1H), 7.53 (dd, J=8, 8Hz, 1H), 7.48 (dd, J=8, 10 Hz, 1H), 7.35 (dd, J=7, 8 Hz, 1H), 3.50 (s, 2H), 3.40 (s, 2H), 2.30 (s, 3H) ppm.

EXAMPLE 17

Synthesis of Guanylhydrazone Mimetics

Guanylhydrazone mimetics of the invention may be synthesized according to Scheme 10.

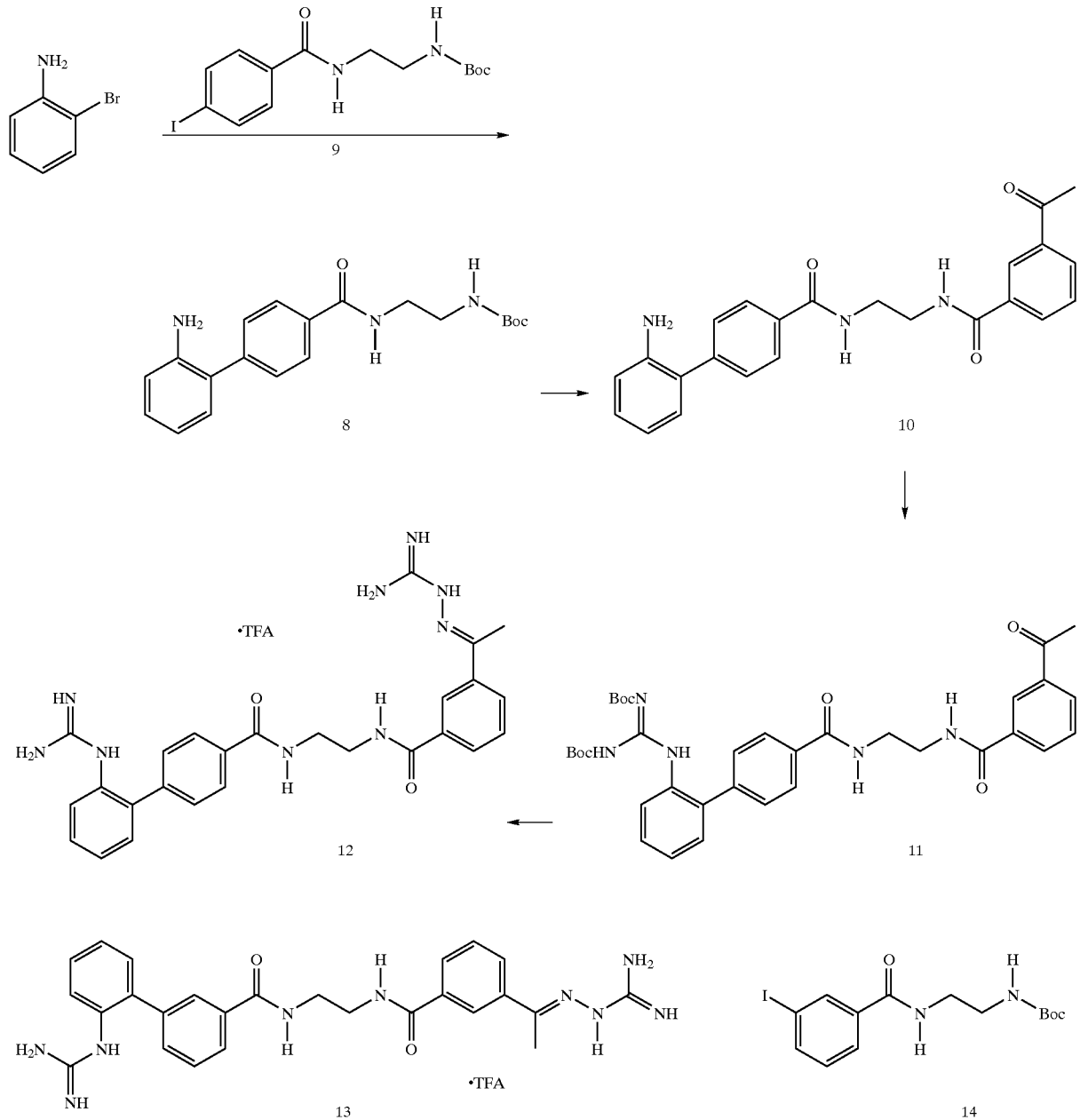

EXAMPLE 18

Synthesis of N-(N'-t-butoxycarbonyl-2-aminoethyl)-4-(2'-aminophenyl)benzamide 8 in Scheme 10

2-Bromoaniline (43 mg, 0.25 mmol) was dissolved in dioxane (540 µL), and to this solution was added triethylamine (4 eq, 101 mg, 140 µL), palladium diacetate (5 mol %, 2.8 mg), dicyclohexyl(2-phenyl)phenylphosphine (20 mol %, 18 mg) and bis(tetramethyl1,3-dioxaborolane) (3 eg, 109 µL) and the mixture heated at 80° C. for 1 hr under an atmosphere of argon. After this time water (216 µL), barium hydroxide (3 eq, 130 mg), and N-(N'-t-butoxycarbonyl-2-aminoethyl)-4-iodobenzamide 9 (1 eq, 97.5 mg) were added, and the reaction mixture heated at 100° C. for 16 hr. After cooling the reaction mixture was partitioned between ethylacetate (20 mL) and water(20 mL). The organic phase was washed with water (3×20 mL), brine (20 mL) and dried over sodium sulfate. The material was absorbed on to silica gel, and chromatography on silica gel eluted with hexanes:ethylacetate (1:3–1:6) gave the desired biphenylamide 7 (44 mg, 50%).

EXAMPLE 19

N-(N'-2-(3-acetylbenzamido)-ethyl)-4-(2'-aminophenyl)benzamide 10 in Scheme 10

Biphenylamide 8 (0.125 mmol) was dissolved in a 50/50 mixture of dichloromethane and trifluoroacetic acid (1 mL) and stirred for 30 min. After which time the volatiles were removed on the rotary evaporator, and toluene (2 mL) was added to the flask. The volatiles were again removed, and the residue was further dried under high vacuum for 5 min. The oily residue was dissolved in dimethylformamide (1 mL) and to this added benzotriazole-1-yl-oxy-tris-(dimethylamino)-phosphonium hexafluoro-phosphate (1.0 eq., 55 mg) and 3-acetylbenzoic acid, (1.0 eq, 21 mg), and N-methylmorpholine (4.0 eq., 50 mg, 55 µL), and the resulting mixture was stirred overnight. The reaction mixture was quenched by the addition of 12 mL of a 0.2 N aqueous sodium hydroxide solution. The resulting mixture was stirred for 4 hr. The reaction mixture was extracted with ethyl acetate (25 mL) and the organic phase was washed with water (4×25 mL), brine (20 mL) and dried over sodium sulfate. The material was absorbed on to silica gel, and chromatography on silica gel eluted with ethyl acetate gave the desired product 10 as a colorless resin (36 mg, 72%).

EXAMPLE 20

N,N'-Bis(t-Butoxycarbonyl)-N"-2-(4-(N-(3-acetylbenzamido)-2-ethyl)-carboxamido)phenyl)phenylguanidine 11 in Scheme 10

Aniline 10 (36 mg, 0.09 mmol) was dissolved in dioxane (0.5 mL), and to this solution was added N,N'-Bis(t-Butoxycarbonyl)-pyrazole-1-carboxamidine (2 eq, 56 mg). The reaction mixture was allowed to stand at r.t. for 8 days. After this time the reaction mixture was diluted with ethyl acetate (10 mL) and washed with water (3×10 mL) and dried over sodium sulfate. The material was absorbed on to silica gel, and chromatography on silica gel eluted with hexanes: ethyl acetate (1:1-0:1) to give the desired product as a colorless oil (30 mg, 52%).

EXAMPLE 21

Mono guanylhydrazone 12 of N,N'-Bis(t-Butoxycarbonyl)-N"-2-(4-(N-(3-acetylbenzamido)-2-ethyl)-carboxamido)phenyl)phenylguanidine, MES 10641

N,N'-Bis(t-Butoxycarbonyl)-N"-2-(4-(N-(3-acetylbenzamido)-2-ethyl)-carboxamido)phenyl)phenylguanidine 11 (30 mg, 0.047 mmol) was dissolved in dry DMSO (0.225 mL) and to this solution added anhydrous ethanol (182 µL), aminoguanidine hydrochloride (2 eq., 10.5 mg), and hydrochloric acid (20 mol %, 43 µL of a 99:1 mixture of EtOH:HCl (conc.)). The reaction mixture was heated to ~100° C. in a sealed vial for 5 days. After which time the vial was removed from the heat bath and allowed to cool. The cap was removed and the ethanol allowed to evaporate at ~100° C. for 30 min. The crude reaction product was purified by preparative reverse-phase HPLC. Lyophilization gave a feathery white solid which was one peak by HPLC Rt=19.5 min (water(60%), 1% trifluoroacetic acid in water(20%), acetonitrile(20%)). 1H NMR (DMSO) δ=10.74 (s, 1H), 9.33 (s, 1H), 8.70 (br s, 2H), 8.28 (s, 1H), 8.19 (d, J=8 Hz, 1H), 7.93 (d, J=9 Hz, 2H), 7.90 (d, J=7 Hz, 1H), 7.72 (br s, 4H), 7.49–7.72 (m, 3H), 7.48 (d, J=9 Hz, 2H), 7.39 (m, 1HH, 7.13 (br s, 4H), 3.50 (s, 4H), 2.44 (s, 3H) ppm.

EXAMPLE 22

Synthesis of 13 in Scheme 10, MES 10642

MES 10642 13 was prepared in an analogous manner to compound MES 10641 12 by employing N-(N'-t-butoxycarbonyl-2-aminoethyl)-3-iodobenzamide 14 instead of N-(N'-t-butoxycarbonyl-2-aminoethyl)-4-iodobenzamide 9. Lyophilization gave a feathery white solid which was one peak by HPLC Rt=13.5 min (water(60%), 1% trifluoroacetic acid in water(20%), acetonitrile(20%)). 1H NMR (DMSO) δ=10.60 (s, 1H), 9.26 (s, 1H), 8.70 (br s, 2H), 8.27 (s, 1H), 8.19 (d, J=8 Hz, 1H), 7.90 (m, 3H), 7.68 (br s, 4H), 7.50–7.58 (m, 5H), 7.39 (m, 1H), 7.10 (br s, 4H), 3.49 (s, 4H), 2.34 (s, 3H) ppm.

EXAMPLE 23

RNase P Inhibition Assay

Figure 1B:
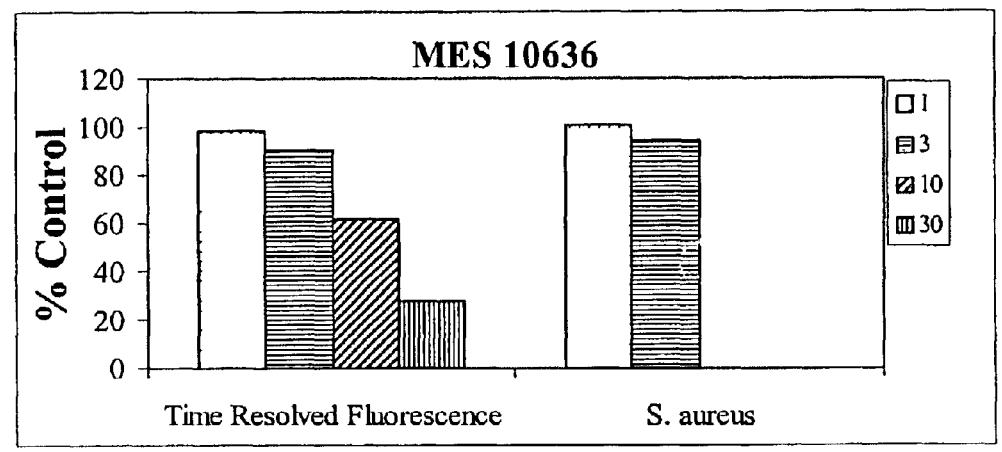
Figure 2:
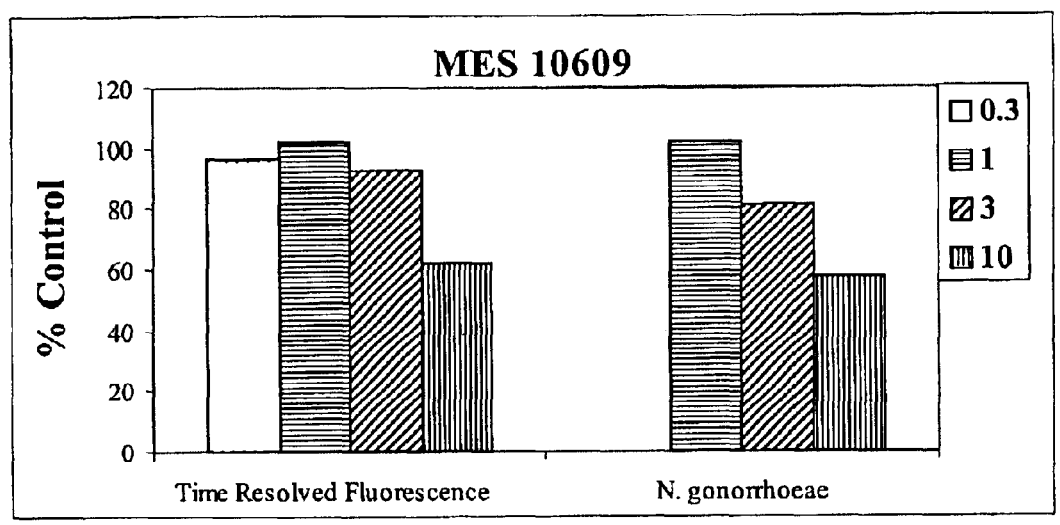
FIG. 2 is a bar graph illustrating the effect of MES 10609 on *N. Gonorrhea* RNase P activity. The fluorescence data illustrates that this compound can inhibit RNase P activity. The *N. Gonorrhea* growth data illustrates that this compound can inhibit bacterial growth. Doses are in $\mu$M.
Figure 7:
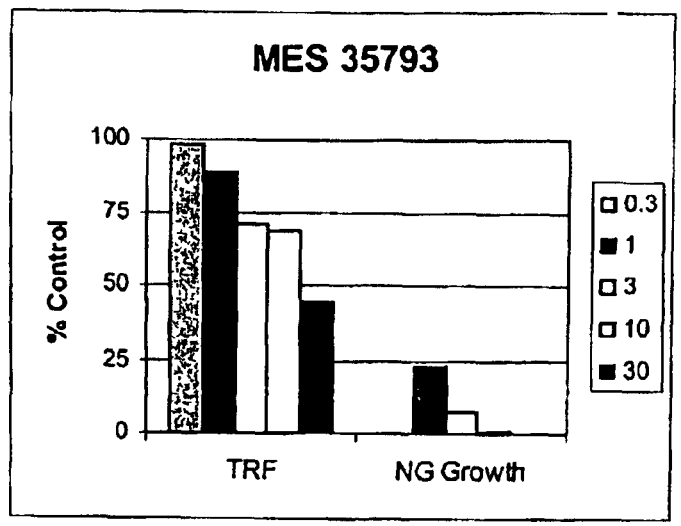
FIG. 7 is a bar graph illustrating the effect of MES 35793 on *N. Gonorrhea* RNase P activity. The fluorescence data illustrates that these compounds can inhibit RNase P activity. The *N. Gonorrhea* growth data illustrates that these compounds can inhibit bacterial growth. Doses are in μM.
Figure 8:
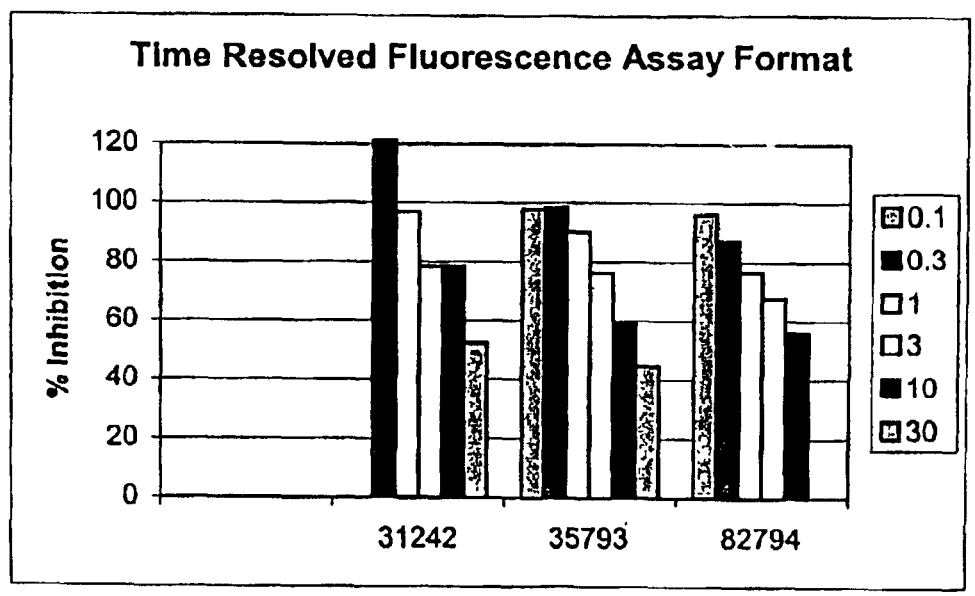
FIG. 8 is a bar graph illustrating the activity of MES 31242, MES 35793, and MES 82794. The fluorescence data illustrates that these compounds can inhibit a representative RNase P (*N. gonorrhoeae*). Doses are in μM.

Compounds of the invention (see Table 1 and FIG. 3) were assayed for inhibition of RNase P activity. The assay components were the M1 RNA and C5 protein from *N. gonorrhea* and a model precursor tRNA substrate derived from *Synechocystis* ptGLN. The compounds were diluted in assay buffer (50 mM Tris-HCl, pH 7.5/100 mM $NH_4Cl_2$/10 mM $MgCl_2$/1 mM DTT/1 mg/ml BSA) from 2 µL of a 1 mM DMSO stock solutions in 384 well polypropylene plates to a concentration of 40 µM. 12.5 µL of each compound dilution was transferred to empty duplicate wells of two 384-well black polystyrene assay plates. One assay plate received 37.5 µL of assay buffer plus 12.5 µL of stop buffer (25 mM EDTA/1.25×SSC Buffer in PA buffer; SSC=150 mM NaCl, 15 mM sodium citrate and PA=50 mM TRIS hydrochloride, 100 mM ammonium chloride, 10 mM magnesium chloride) and was read immediately on a LJL Analyst fluorimeter to serve as a background fluorescence plate. The other plate sequentially received the following reagents diluted in assay buffer, 12.5 µL of 0.4 nM M1 RNA, 12.5 µL of 2 nM C5 protein, and 12.5 µL of 160 nM substrate. Wells were included that receive neither the M1 RNA nor the C5 protein to serve as no-enzyme controls. The enzymatic reaction was allowed to proceed for 30 minutes and was stopped by the addition of 12.5 µL per well of stop buffer containing 20 nM of a DNA-5' TAMRA probe complementary to the 5' end of the substrate. The probe was allowed to hybridize to the substrate for 2 hours, and the polarization status of the probe was measured using the LJL Analyst fluorimeter. All compounds were tested at 0.3 µM, 1 µM, 3 µM, and 10 µM concentrations. The results, which are expressed as a percentage of the control, were calculated using equation 1. In this equation, f is the fluorescence in counts per second; (f.enzyme+probe) is the fluorescence observed when enzymatic activity is uninhibited; (f.probe) is the fluorescence observed without enzymatic activity; and (f.compound+enzyme+probe) is the fluorescence observed when the enzymatic activity is modulated by a compound of the invention. The assay results are provided in FIGS. 1A–3. MES 10635, MES10636, MES 67402 and MES10609 are inhibitors of RNase P activity, as shown in FIGS. 1A–2. Assay results for MES 35793 are shown in FIG. 7, and assay results for MES 31242, MES 82794, and MES 35793 are shown in FIG. 8. Other candidate RNase P inhibitors may be tested similarly using any RNase P holoenzyme and any appropriate RNase P substrate.

$$\% \text{ control} = \left[1 - \left(\frac{(f \cdot compound + enzyme + probe) -}{(f \cdot enzyme + probe)}\right)\right] \times 100 \qquad \text{Eq 1.}$$

EXAMPLE 24

Bacterial Inhibition Assay

Compounds of the invention (see Table 1 and FIG. 3) were assayed for their ability to inhibit bacterial growth. Compounds were diluted from 10 mM DMSO stocks to 3 mM and 1 mM in DMSO. The compounds were further diluted from these stocks into saline for 200, 120, and 20 $\mu$M stocks. Control antibiotics were diluted similarly. Overnight cultures of bacteria were made in the following manner. $N.$ $gonorrhea$ was streaked onto a chocolate agar plate and incubated at 35° C./5% $CO_2$. A loopful from a stock plate of $E.$ $coli$ was added to 3 mL TSB medium, vortexed and incubated at 37° C. in the absence of $CO_2$. An $S.$ $aureus$ culture was made as described for the $E.$ $coli$ culture, except that a nutrient broth was used instead of TSB medium. Rather than make an overnight culture of $S.$ $pyogenes$, a loopful of $S.$ $pyogenes$ from a blood plate or a stock plate was used the following day for direct cell suspension.

On the following day bacteria were prepared by dilution into saline with O.D. 625 nM readings taken to determine the concentration of the bacteria. CFUs (colony forming units) were determined using the formula: CFU/mL= $OD_{625} \times (1.5 \times 10^8$ CFU/mL/OD McFarland std)×dilution. The four bacterial cultures were diluted initially to $5.5 \times 10^7$ CFU/mL. The bacteria were then further diluted into medium to $5.5 \times 10^5$ CFU/mL for $S.$ $aureus$, $S.$ $pyogenes$ and $E.$ $coli$ and $5.5 \times 10^6$ CFU/mL for $N.$ $gonorrhea$. $S.$ $aureus$ and $E.$ $coli$ are grown in CAMHB medium and $S.$ $pyogenes$ and $N.$ $gonorrhea$ in CAMHB-3% LHB medium. The bacteria were added one per plate at 200 $\mu$L per well. Compounds were added in 10 $\mu$L for final concentrations of 10, 3 and 1 $\mu$M in duplicate. Control antibiotics for $S.$ $aureus$, oxacillin; for $S.$ $pyogenes$, penicillin; for $E.$ $coli$, ampicillin; and for $N.$ $gonorrhea$, ciprofloxacin were added from 0.8 mg/ml to 0.003 mg/ml. Plates were incubated at 35° C. with $O_2$ for 16–20 hours for $S.$ $aureus$, $S.$ $pyogenes$, and $E.$ $coli$ and read at $OD_{665}$ in the Victor2 plate reader. Plates were incubated at 35° C. with 5% $CO_2$ for 24 hours for $N.$ $gonorrhea$ at which time 40 $\mu$L of MTS reagent is added per well and incubated for 1 hour in same incubator. The plates were read at $OD_{490}$. Compounds were tested at 1 $\mu$M, 3 $\mu$M, and 10 $\mu$M concentrations. The results, which are expressed as a percentage of the control, were calculated using equation 2. In this equation, O.D. is optical density; (O.D.compounds+ bacteria) is the optical density observed for bacteria grown in the presence of a compound of the invention; (O.D.blank) is the optical density in the absence of bacteria; and (O.D.bacteria) is the optical density observed for bacteria growing uninhibited. The assay results are provided in FIGS. 1A–3 and 7. MES 10635, MES10636, MES 67402, MES10609, and MES 35793 are inhibitors of bacterial growth, as shown in FIGS. 1A–2. Other RNase P inhibitors may be tested similarly using any bacteria of interest.

$$\% \text{ control} = \left(\frac{O.D. \text{ compound} + bacteria) - (O.D. \text{ blank})}{(O.D. \text{ bacteria}) - (O.D. \text{ blank})}\right) \times 100 \qquad \text{Eq 2.}$$

EXAMPLE 25

Toxicity Assay

Compounds of the invention (see Table 1 and FIG. 3) were assayed for cellular toxicity as follows. Whole blood was drawn from a volunteer, and the red cells were separated from the buffy coat cells by centrifugation over ficoll-paque. The resulting peripheral blood mononuclear cells (PBMC) were collected from the interface and washed extensively with PBS by centrifugation to remove platelets and cellular debris. The cells were then plated in 96-well tissue culture plates at a density of $5 \times 10^5$ cells per mL at 200 $\mu$L per well. After an hour incubation, the candidate compounds were added at the appropriate concentrations diluted from DMSO stocks into assay buffer (RPMI medium supplemented with 10% FCS). The cells were incubated at 37° C., 100% humidity and 5% $CO_2$ for 24 hours at which time MTS reagent was added per the manufacturer's (Promega) instructions. After 2–3 hours incubation the optical density of the wells was read on a spectrophotometer. Viable cells turn the MTS reagent from a yellow solution to a blue solution but dead cells do not. The data are evaluated using equation 2 as described in Example 24, where bacterial cells are replaced by PBMC cells in the measurements. The assay results are provided in FIG. 3. The data describes the toxicity of these compounds to a representative human cell population (PBMC's). This toxicity data can be compared to the activity in the bacterial growth assays, and used to identify compounds that selectively inhibit bacterial cell growth without adversely effecting eukaryotic cell types such as PBMC's.

EXAMPLE 26

Other Assays That Can Be Used to Measure RNase P Inhibition

To test the compounds of the invention for their ability to inhibit other RNase P holoenzymes, the rnpA genes encoding RNase P proteins or protein subfragments are amplified from genomic DNA by established PCR methods. The amplified DNA sequences that encode the RNase P protein genes are subcloned into expression plasmids, which contain fusion sequences allowing the subcloned gene to be expressed in a transformed or transfected host cell as a "tagged" fusion protein. $E.$ $coli$ cells are transformed with the plasmid DNA, protein expression is induced, and the overexpressed fusion protein is isolated by affinity purification according to established protocols.

Each of the purified RNase P proteins is combined with a renatured cognate RNase P RNA subunit from the same, or a different, bacterial organism, under conditions that reconstitute enzymatic activity. It is possible to reconstitute a functional RNase P holoenzyme using a protein subunit and an RNA subunit from different species (e.g., $B.$ $subtilis$, $E.$ $coli$, or $S.$ $aureus$). The conditions for reconstitution include heat denaturing the RNA subunit then slowly cooling in a physiologically similar buffer. A buffer for folding the RNA component of RNase P is 10–50 mM Tris-HCl/MOPS/

HEPES (pH=7.0–8.0), 25–500 mM KCl/NaCl/NH$_4$, and 1–25 mM MgCl$_2$. The RNA is heated to 65° C. for 5 minutes, 55° C. for minutes, and 37° C. for 5 minutes. The protein is then added along with 1–10 mM DTT and the incubation is optionally continued at 37° C. for 5 minutes. Similar heating protocols known in the art may also be used. The protein is then incubated briefly with the renatured RNA to reconstitute holoenzyme activity.

The RNase P substrates used in the assay can be labeled. Examples of labeled nucleotides that can be incorporated into the RNA substrates include BrdUrd (Hoy et al., Mutation Research 290: 217, 1993), BrUTP (Wansick et al., J. Cell Biology 122:283, 1993) and nucleotides modified with biotin (Langer et al., Proc. Natl. Acad. Sci. USA 78: 6633, 1981) or with suitable haptens such as digoxygenin (Kerhof, Anal. Biochem. 205: 359, 1992). Suitable fluorescence-labeled nucleotides are fluorescein-isothiocyanate-dUTP, cyanine-3-dUTP and cyanine-5-dUTP (Yu et al., Nucleic Acids Res. 22:3226, 1994). An exemplary nucleotide analog label for RNA molecules is biotin-14-cytidine-5'-triphosphate. Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

The amplified rnpA genes may also be cloned into expression vectors not containing encoded fusion tag sequences, but still containing an inducible promoter. After induction, the overexpressed protein can be purified essentially by the protocol for purification of E. coli RNaseP protein (Baer et al., Meth. Enzymol. 181:569,1990).

Examples of RNA substrates that can be used to measure RNase P enzymatic activity include the full-length substrate ptRNA$^{Tyr}$ (pTyr) (Altman and Kirsebom, The RNA World, 2nd Ed., Cold Spring Harbor Laboratory Press: Cold Spring Harbor, N.Y., 1999), and ptRNA$^{Gln}$ (pGln), an 85-mer from the cyanobacterium Synechocystis (Pascual and Vioque, Proc. Natl. Acad. Sci. USA 96: 6672, 1999) or a substrate obtained from the homologous bacteria.

A modified ptRNA$^{Gln}$ substrate can also be used, in which the 5' end is fluorescently tagged in order to monitor hydrolysis using fluorescence spectroscopy. Given that the chemical synthesis of an 85-mer with a fluorescent tag is technically impractical, and the fluorescent modification enzymatically synthesized RNA is difficult, the exemplary method of synthesizing a fluorescently tagged pGln is conducted with the following two steps: a 5' fluorescently modified 26-nucleotide fragment is chemically synthesized and annealed to a 3'59-nucleotide fragment that has been enzymatically synthesized. These two fragments, when annealed, form a full-length pGln substrate. The unligated junction between the two fragments occurs in the D-loop, a region that is not required for function by the RNase P holoenzyme.

In addition, substrates that contain only the minimally required structural elements for recognition by the enzyme can also be utilized for this reaction, although the K$_m$ values for these substrate fragments are usually much higher than the above-described full-length substrates. One example of a substrate fragment is p10AT1, a 45-mer that contains a 10-nucleotide 5' leader sequence, an extended 12-base pair stem which is made up of the aminoacyl acceptor stem, a T-stem, and a single loop. The K$_m$ for hydrolysis reactions using this simplified substrate fragment rises to greater than 1 µM (McClain et al., Science 238:527,1987). Therefore, while the substrate fragment is easier to contact, it requires a higher concentration in an enzymatic assay.

The progress of the RNase P-mediated hydrolysis reaction is monitored, for example, by fluorescence spectroscopy. For example, a fluorescence polarization assay for RNase P activity is conducted by labeling the 5' end of the substrate, for example, the 45-mer (p10AT1) or the 85-mer (pGln) substrate, with an appropriate fluorophore. Given that compounds in screening libraries often interfere with fluorescence measurements in the blue to yellow region of the spectrum, exemplary fluorophores emit light in the red region of the spectrum (e.g., TAMRA (Molecular Probes, OR) and Cy3 labeled nucleotide (Dharmacon Research, CO.)) Samples of the RNase P holoenzyme and the RNase P substrate are mixed, incubated, and measured for spectrophotometric polarization. When the substrate is cleaved by the RNase P holoenzyme, the 10-nucleotide 5'-leader sequence is released, which leads to a substantial change in the fluorescence polarization in the sample. (Campbell et al. Biological Spectroscopy, Benjamin/Cummings: Menlo Park, Calif. pp. 91–125 1984; Lakowicz Principles of Fluorescence Spectroscopy, chapter 5, Plenum Press: New York, 1983).

The exemplary reaction buffer contains 50 mM Tris-HCl (pH 7.5), 100 mM ammonium chloride, and 10 mM magnesium chloride. Concentrations of 10–100 mM, 25–500 mM, and 1–100 mM of the above, respectively, can be substituted, as can other buffering agents such as MOPS or HEPES, or other monovalent cations, such as sodium or potassium. When the assay is run in either 98 or 364-well polystyrene or polypropylene assay plates, there is a very significant decrease in the fluorescence intensity and polarization of the annealed substrate over time in the absence of enzyme. Various conditions have been tested to prevent the loss of signal with time. The exemplary conditions include addition of 10–40 µg/ml carbonic anhydrase and 10–100 µg/ml polyC to the buffer. Other materials, such as, 0.5–5% glycerol, 10–100 µg/ml hen egg lysozyme, 10–50 µg/mL tRNA, or 2–10 mM DTT can also be added to the buffer to prevent some loss of signal. The RNase P hydrolysis rate can also be monitored using a radiolabeled substrate, performing a surface proximity assay (SPA), and measuring hydrolysis by scintillation counting. For example, the substrate is anchored to the surface of the assay plate via a biotin-streptavidin interaction between a biotinylated nucleotide in the anticodon loop and a streptavidin matrix on the plate. The substrate is also $^{33}$P-labeled at the 5' end. Using this method, RNase P-mediated hydrolysis of the 5' leader sequence results in decreased scintillation due to reduced proximity of the radiolabel to the scintillation-coated plate. (Brown et al., FlashPlate Technology, in High Throughput Screening: The Discovery of Bioactive Substances, J. P. Devlin (Ed.), Marcel Dekker: New York pp. 317–328,1997).

A bipartite substrate for RNase P, consisting of a 5'-end Cy3 labeled 26mer and an in vitro T7-polymerase transcribed 59mer is exemplary for screening. The 26mer consists of the first 26 contiguous nucleotides of the pre-tRNA substrate including the 10-nucleotide leader sequence. The two RNA fragments are annealed together under appropriate conditions of stoichiometry (59mer in 20 to 100% excess) and temperature in a buffer system consisting of 50 mM Tris-HCl (pH 7.5), 100 mM ammonium chloride, and 10 mM magnesium chloride. Briefly, the two RNA fragments are mixed together and heated to between 65° C. and 80° C. for about 5 minutes and then slowly cooled to room temperature.

In addition, the RNase P enzyme activity can also be measured using standard techniques described in the literature (see, e.g., Altman and Kirsebom, Ribonuclease P, The RNA World, 2nd Ed., Cold Spring Harbor Laboratory Press: Cold Spring Harbor, N.Y., 1999; Pascual and Vioque, Proc. Natl. Acad. Sci. 96:

6672, 1999; Geurrier-Takada et al., Cell 35: 849, 1983; Tallsjö and Kirsebom, Nucleic Acids Research 21: 51, 1993; Peck-Miller and Altman, J. Mol. Biol. 221: 1, 1991; Gopalan et al., J. Mol. Biol. 267: 818, 1997; and WO 99/11653).

To screen for compounds that inhibit the activity of the RNase P holoenzymes, compounds are added to a final concentration of 10 µM before the addition of substrate to the sample. A compound is determined to be an inhibitor if it significantly reduces RNase P hydrolysis as compared to the compound-free control sample. Ideally, the compounds identified as inhibitors selectively inhibit one of the RNase P holoenzymes of the invention without affecting other RNase P holoenzymes. Such inhibitors have the advantage of providing a selective antibacterial treatment that reduces the adverse side effects associated with killing nonpathogenic bacteria. Use of such selective inhibitors also reduces the risk of producing a wide range of resistant bacterial strains.

Compounds of the invention may also be assayed to determine if they reduce or stabilize the level of an RNase P protein or nucleic acid subunit. For example, an antibody reactive wilth an RNase P subunit may be generated as disclosed in U.S. Ser. No. 09/798,635 filed Mar. 1, 2000, and used to measure the levels of the subunit in the presence and absence of the compound of the invention.

EXAMPLE 27

RNase P Protein Amino Acid and Nucleic Acid Sequences for Use in Identifying RNase P Inhibitors As described in U.S. Ser. No. 09/798,635 filed Mar. 1, 2000, other RNase P proteins that may be used to identify RNase P inhibitors, and the nucleic acid sequences which encode the proteins, are derived from the following bacterial species: *Streptococcus mutans* UAB159; *Klebsiella pneumoniae* M6H 78578; *Salmonella paratyphi* A (ATCC 9150); *Pseudomonas aeruginosa* PAO1; *Corynebacterium diphtheriae*; *Chlamydia trachomatis* MoPn; *Vibrio cholerae* Serotype 01, Biotype E1 Tor, Strain N16961; *Neisseria gonorrhoea* FA 1090; *Neisseria meningitidis* Serogroup A, Strain Z2491; *Streptococcus pyogenes* M1; *Bordetella pertussis* Tohama I; *Porphyromonas gingivalis* W83; *Streptococcus pneumoniae* Type 4; *Clostridium difficile* 630; *Camphylobacter jejuni* NCTC; *Bacillus anthracis* Ames; *Mycobacterium avium* 104. *Staphylococcus aureus* NCTC 8325; *Staplylococcus aureus* COL; *Pasteurella multocida* PM70; *Haemophilus ducreyi* strain 35000HP; *Chlamydia muridarum*; *Chlamydophila psittaci*; *Treponema denticola*; *Enterococcus faecalis*; *Legionella pneumophila*; *Staphylococcus epidermis*; *Mycobacterium smegmatis*; *Burkholderia pseudomallei*; and *Ureaplasma urealyticum*. The sequences are shown in FIGS. 5 and 6.

Figure 4A:
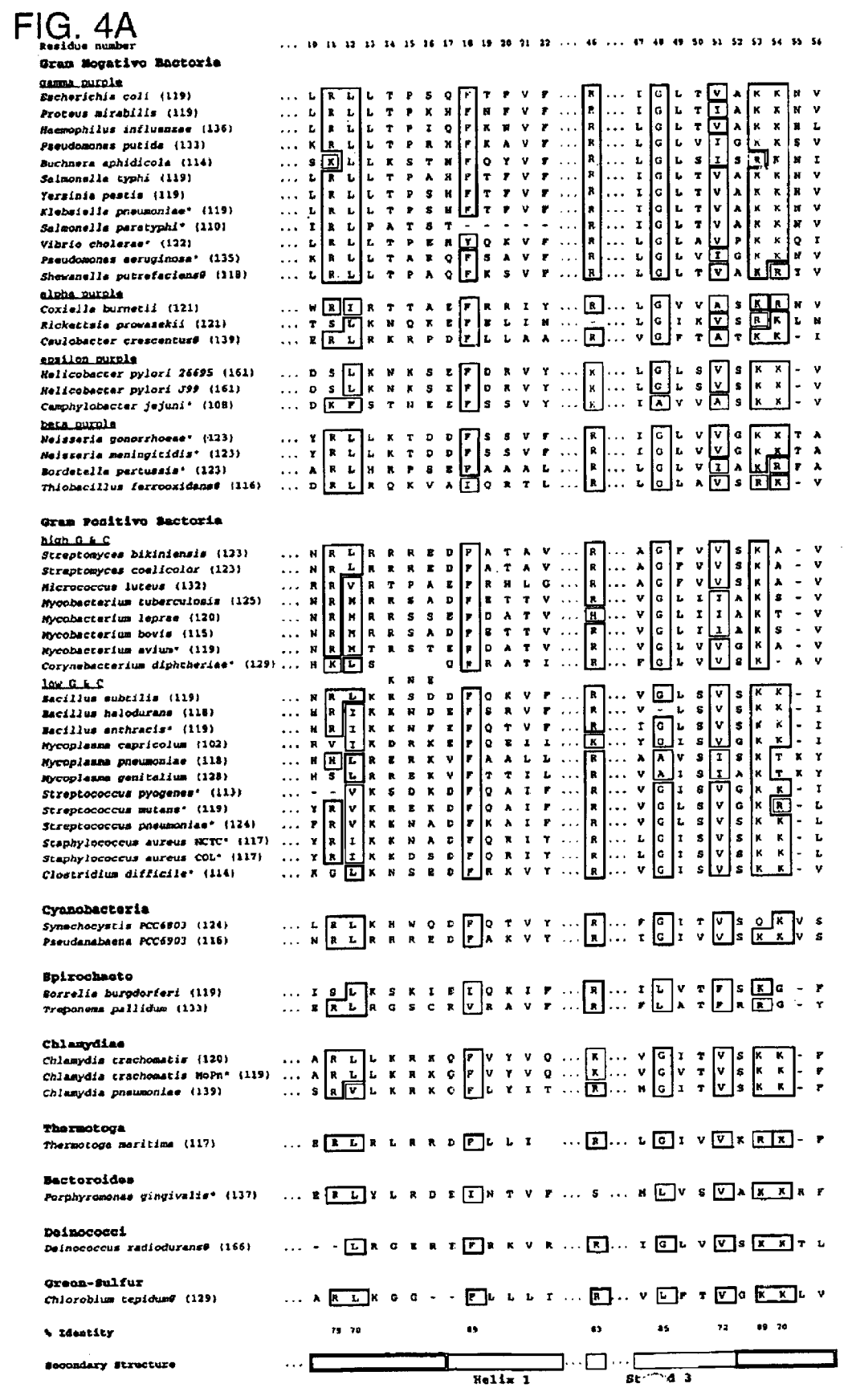
Figure 4B:
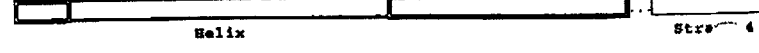
Figure 4C:
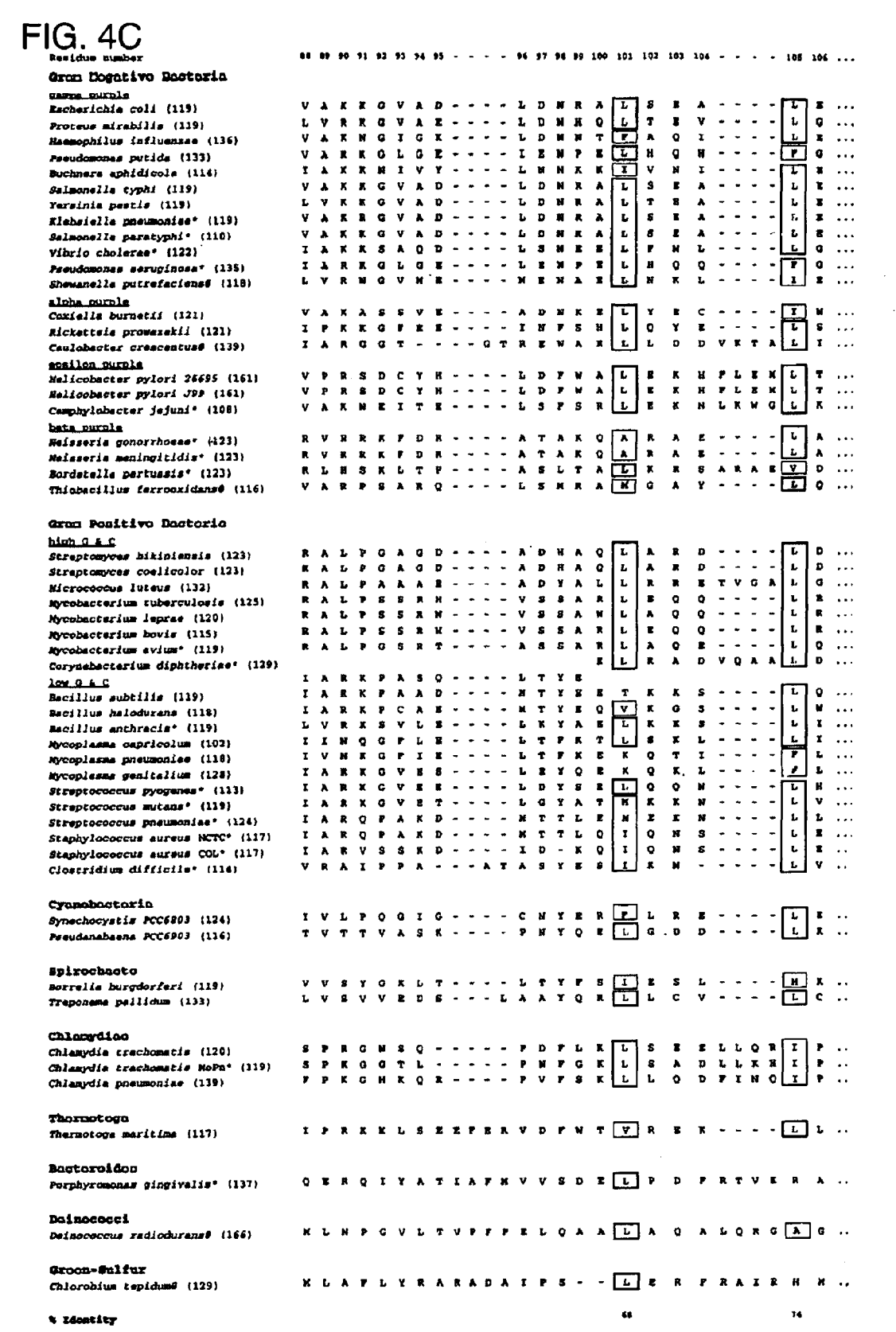

All of these RNase P protein sequences were identified by the above-described BLAST search. The alignment of some of these sequences with the known RNase P sequences is also shown in FIG. 4 (the RNase P sequences disclosed in U.S. Ser. No. 09/798,635 filed Mar. 1, 2000, are shown in this figure are designated by (*)). This alignment demonstrates that the amino acid sequences contain RNase P consensus sequences. Therefore, these polypeptides are genuine RNase P proteins.

The RNase P identification is further supported by the protein structure of these polypeptides, as determined by SWISS-MODEL. The polypeptide sequences were readily folded (at least in part) into the tertiary structure of the *B. subtilis* RNase P protein subunit (Stams et al., Science 280:752, 1998). It is noteworthy that conserved residues in the newly identified sequences are modeled into positions which are spatially and structurally identical to the RNase P protein subunit of *B. subtilis*.

Further support for the RNase P identification is as follows. Using the above-described BLAST search and consensus sequence determination, we independently identified the sequence for an RNase P protein subunit from the genomic database of *Staphylococcus aureus* (*S. aureus*). Although this sequence had been previously identified as an RNase P protein subunit and its RNase P activity had been confirmed by assay (EP 0 811 688 A2), our independent discovery of this RNase P sequence (U.S. Ser. No. 09/798, 635 filed Mar. 1, 2000) provides proof of principle that our method of searching for RNase P protein subunits predictably identifies polypeptides that have RNase P activity.

The methods of the invention may be used with any purified or isolated RNase P protein subunits to identify compounds that inhibit these RNase P enzymes. As used herein, both "protein" and "polypeptide" mean any chain of amino acids, regardless of length or post-translational modification (e.g., glycosylation or phosphorylation). Thus, the term RNase P protein subunit includes full-length, naturally-occurring RNase P proteins, preproteins, and proproteins, as well as recombinantly or synthetically produced polypeptides that correspond to full-length, naturally-occurring RNase P proteins or to particular domains or portions of naturally-occurring proteins. These proteins are produced using standard techniques (see, e.g., Ausubel et al., *Current Protocols in Molecular Biology*, Wiley: New York, 1995; Pouwels et al., *Cloning Vectors: A Laboratory Manual*, 1985 (1987 Suppl.); and Sambrook et al., *Molecular Cloning, A Laboratory Manual*, 2nd ed., Cold Spring Harbor Laboratory Press: Cold Spring Harbor, N.Y., 1989).

Desired RNase P proteins include a sequence substantially identical to all or a portion of a naturally occurring RNase P protein subunit, e.g., including all or a portion of any of the sequences shown in FIG. 5 (SEQ ID NOS: 20–38) and FIG. 6 (SEQ ID NOS: 50–60).

In the case of polypeptide sequences which are less than 100% identical to a reference sequence, the non-identical positions are desirably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Desired polypeptides are those which are soluble under normal physiological conditions. Also, soluble fusion proteins in which a full-length or subfragment of RNase P protein (e.g., one or more domains) is fused to an unrelated protein or polypeptide (i.e., a fusion partner) to create a fusion protein may be used.

Structurally related RNase P polypeptides include, but are not limited to, polypeptides with additions or substitutions of amino acid residues within the amino acid sequence encoded by the RNase P nucleic acid sequences described herein; these changes result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Desired RNase P polypeptides and variants have 20%, 50%, 75%, 90%, or even 100% or more of the activity of one of the bacterial RNase P proteins of SEQ ID NOS: 20–38 shown in FIG. 5, or of SEQ ID NOS: 50–60 shown in FIG. 6. Such comparisons are generally based on equal concentrations of the molecules being compared. The comparison can also be based on the amount of protein or polypeptide required to reach the maximal activation obtainable.

In general, RNase P proteins can be produced by transformation (transfection, transduction, or infection) of a host cell with all or part of a RNase P-encoding nucleic acid sequence in a suitable expression vehicle. Such expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LACSWITCH™ Inducible Expression System (Stratagene, LaJolla, Calif.).

Those skilled in the field of molecular biology will understand that any of a wide variety of expression systems can be used to provide the recombinant protein (see, e.g., Ausubel et al., *Current Protocols in Molecular Biology*, Wiley: New York, 1995; Pouwels et al., *Cloning Vectors: A Laboratory Manual*, 1985 (1987 Suppl.); and Sambrook et al., *Molecular Cloning, A Laboratory Manual*, 2nd ed., Cold Spring Harbor Laboratory Press: Cold Spring Harbor, N.Y., 1989). The precise host cell used is not critical. The RNase P protein can be produced in a prokaryotic host (e.g., *E. coli* or *B. subtilis*) or in a eukaryotic host (e.g., *Saccharomyces* or *Pichia*; mammalian cells, e.g., COS, NIH 3T3 CHO, BHK, 293, or HeLa cells; or insect cells; or plant cells).

The host cells harboring the expression vehicle can be cultured in conventional nutrient media adapted as needed for activation of a chosen gene, repression of a chosen gene, selection of transformants, or amplification of a chosen gene.

RNase P proteins can be produced as fusion proteins. For example, the expression vector pUR278 (Ruther et al., EMBO J. 2: 1791, 1983), can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

The methods of the invention may also be used with the isolated nucleic acid sequences of SEQ ID NOS: 1–19 shown in FIG. 5 and SEQ ID NOS: 39–49 shown in FIG. 6, and nucleic acid sequences that encode one or more portions or domains of an RNase P protein subunit, including but not limited to the $\alpha 1$, $\alpha 2$, $\alpha 3$, $\beta 1$, $\beta 2$, $\beta 3$, and $\beta 3$ portions of the protein.

Desired nucleic acids encode polypeptides that are soluble under normal physiological conditions. Also, nucleic acids encoding fusion proteins in which the whole RNase P protein or a sub-fragment is fused to an unrelated protein or polypeptide (e.g., a marker polypeptide or a fusion partner) may be used to create a fusion protein. For example, the polypeptide can be fused to a hexa-histidine tag to facilitate purification of bacterially expressed protein, or to a hemagglutinin tag to facilitate purification of protein expressed in eukaryotic cells.

The fusion partner can be, for example, a polypeptide which facilitates secretion, e.g., a secretory sequence. Such a fused protein is typically referred to as a preprotein. The secretory sequence can be cleaved by the host cell to form the mature protein. Also, nucleic acids that encode a mature RNase P protein fused to a polypeptide sequence may be used to produce an inactive proprotein. Proproteins can be converted into the active form of the protein by removal of the inactivating sequence.

Nucleic acids that may be assayed in the methods of the invention further include sequences that hybridize, e.g., under high stringency hybridization conditions (as defined herein), to all or a portion of the nucleic sequence of any one of SEQ ID NOS: 1–19 or 39–49, or any of their complements. As used herein, high stringency conditions include hybridizing at 68° C. in 5×SSC/5×Denhardt solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO4 (pH 7.2)/1 mM EDTA/5% SDS at 50° C., or in 40 mM NaHPO$_4$ (pH 7.2)/1 mM EDTA/1% SDS at 50° C. The parameters of salt concentration and temperature can be varied to achieve the desired level of identity between the probe and the target nucleic acid. Further guidance regarding hybridizing conditions is provided, for example, in Sambrook et al., *Molecular Cloning, A Laboratory Manual*, Cold Springs Harbor Press: New York, 1989; Ausubel et al., *Current Protocols in Molecular Biology*, Wiley: New York, 1995).

The hybridizing portion of the hybridizing nucleic acids are desirably 20, 30, 50, or 70 bases long. Desirably, the hybridizing portion of the hybridizing nucleic acid is 80%, more desirably 95%, or even 98% identical, to the sequence of a portion or all of a nucleic acid encoding an RNase P protein subunit. Hybridizing nucleic acids of the type described above can be used as a cloning probe, a primer (e.g., a PCR primer), or a diagnostic probe. Desired hybridizing nucleic acids encode a polypeptide having some or all of the biological activities possessed by a naturally-occurring RNase P protein subunit. Such biological activity can be determined by functional RNase P assay as described herein.

Hybridizing nucleic acids can be additional splice variants of the RNase P protein gene. Thus, they may encode a protein which is shorter or longer than the different forms of RNase P described herein. Hybridizing nucleic acids may also encode proteins that are related to RNase P (e.g., proteins encoded by genes which include a portion having a relatively high degree of identity to the RNase P genes described herein).

Other Embodiments

All publications, patent applications, and patents referenced in this specification are hereby incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are in the claims.

What is claimed is:

1. A method of killing or inhibiting the growth of bacteria, said method comprising contacting bacteria or a site susceptible to bacterial growth with a pharmaceutical composition comprising a pharmaceutically acceptable carrier and an effective amount of a compound of the formula I:

Y—(NR')$_k$—U$_1$—(NR")—A—(NR$^1$)$_m$—U$_2$—(NR$^2$)$_n$—Z    I or a derivative, salt, racemic mixture, mixture of E/Z isomers, or mixture of diastereomers thereof; wherein U$_1$ and U$_2$ are independently carbonyl, thiocarbonyl, or sulfonyl; k, l, m, and n are independently 0 or 1; A is a linker of 1, 2, 3, 4, 5, 6, 7, or 8 atoms that is optionally substituted with a group selected from alkyl, heteroalkyl, alkene, heteroalkene, alkyne, heteroalkyne, aryl, alkaryl, and heteroaryl; R', R", R$^1$, and R$^2$ are independently H, alkyl, heteroalkyl, alkene, heteroalkene, alkyne, heteroalkyne, aryl, or heteroaryl; Y is selected from the group consisting of formulas II, III, IV, V, VI, VII, VIII, IX, and X; and Z is selected from the group consisting of substituted phenyl and formulas II, III, IV, V, VI, VII, VIII, IX, X, and XI:

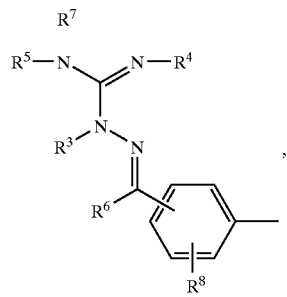

II

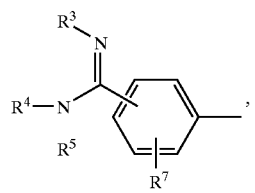

III

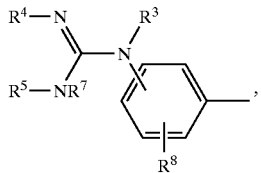

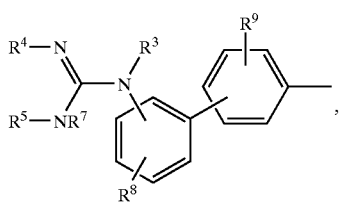

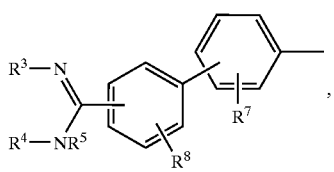

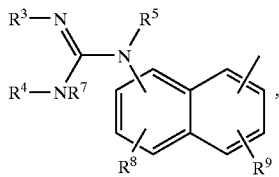

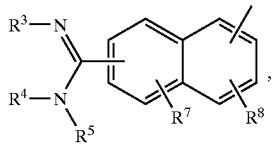

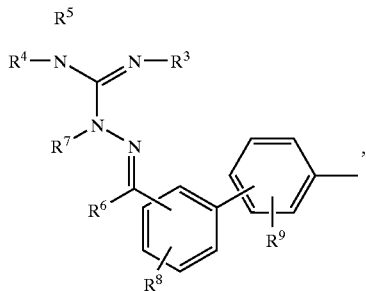

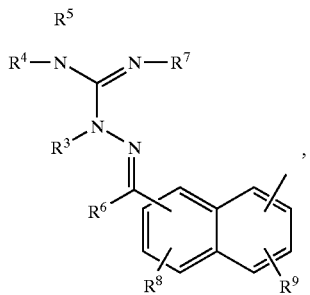

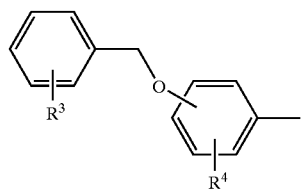

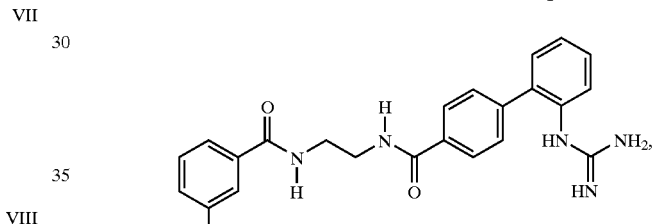

wherein each $R^3$, $R^4$, $R^5$, $R^7$, $R^8$, or $R^9$ is independently H, alkyl, aralkyl, heteroalkyl, alkene, heteroalkene, alkyne, heteroalkyne, aryl, or heteroaryl; and each $R^6$ is H, or alkyl; wherein said substituted phenyl group comprises hydroxy, alkoxy, aryloxy, sulfhydryl, alkylthio, arylthio, halogen, fluoroalkyl, carboxyl, carboxyalkyl, amino, aminoalkyl, monosubstituted amino, disubstituted amino, quaternary amino, nitro, alkyl, heteroalkyl, alkene, heteroalkene, alkyne, heteroalkyne, aryl, or heteroaryl; provided that when A is propylene or substituted phenylene, k and n are both 1, and l and m are both 0, Z and Y are not both formula II.

2. The method of claim 1, wherein said compound is

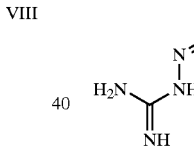

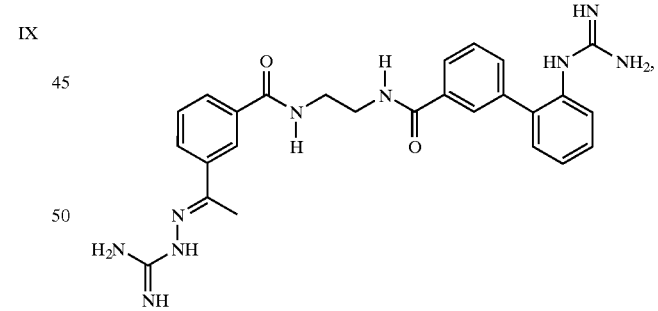

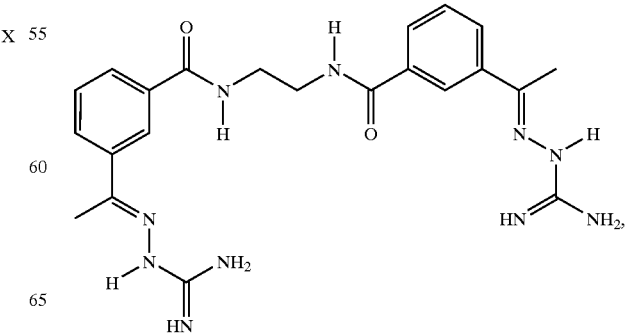

145
-continued
146
-continued
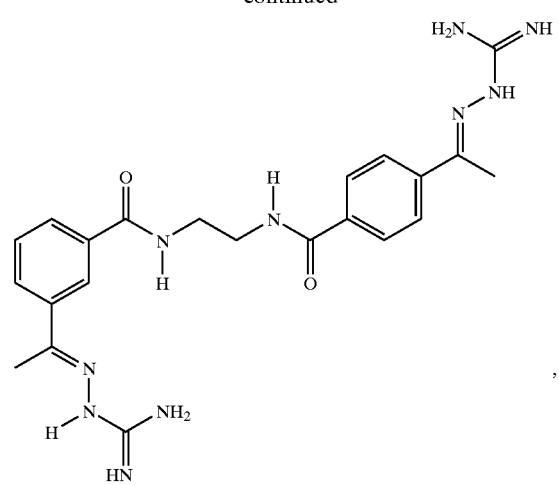
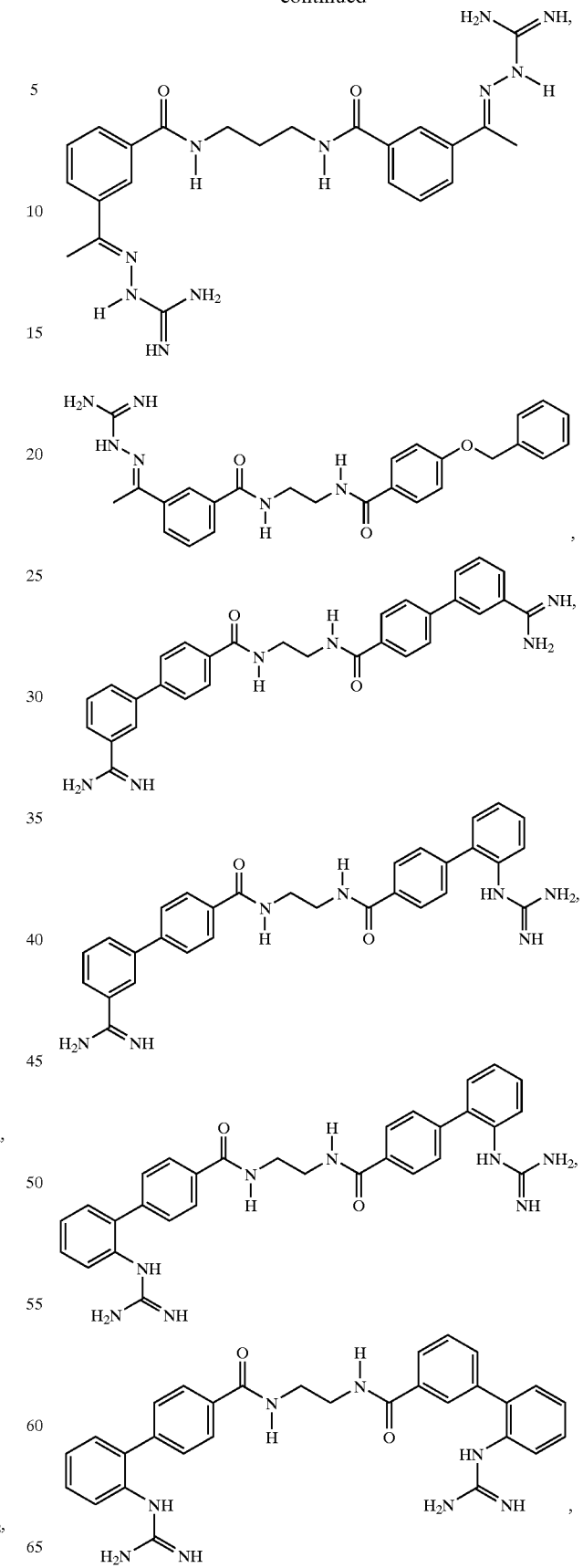

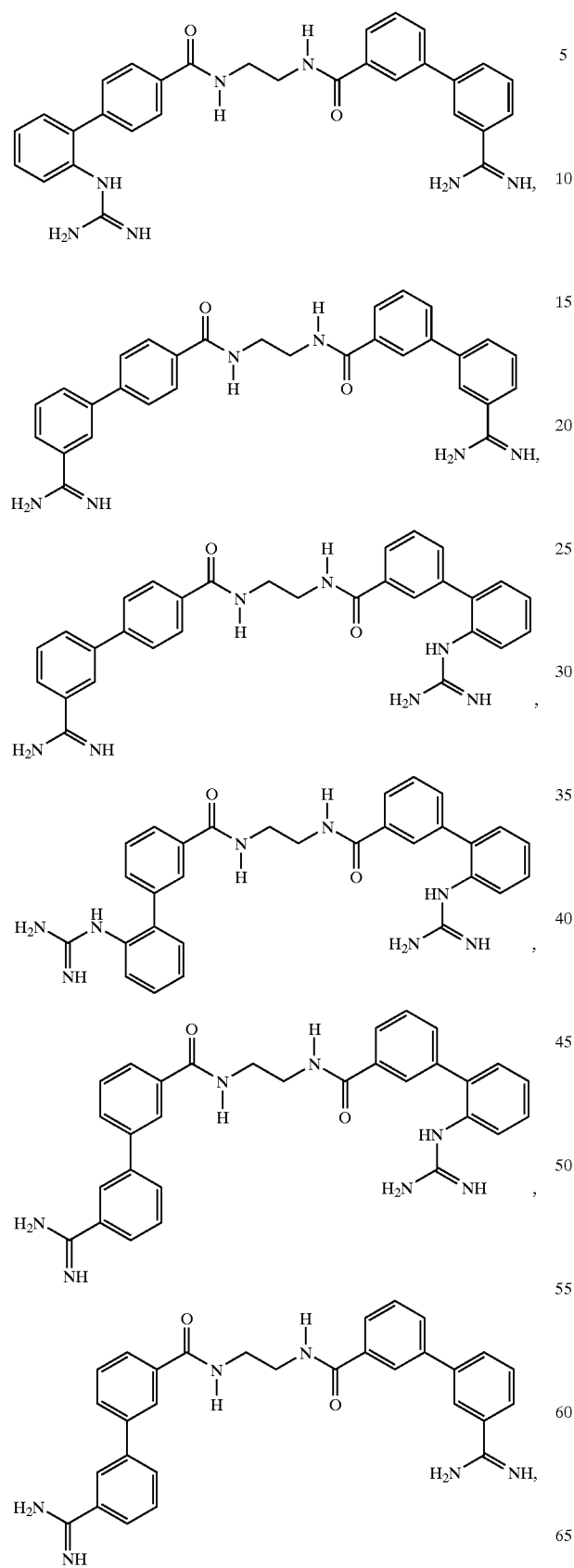
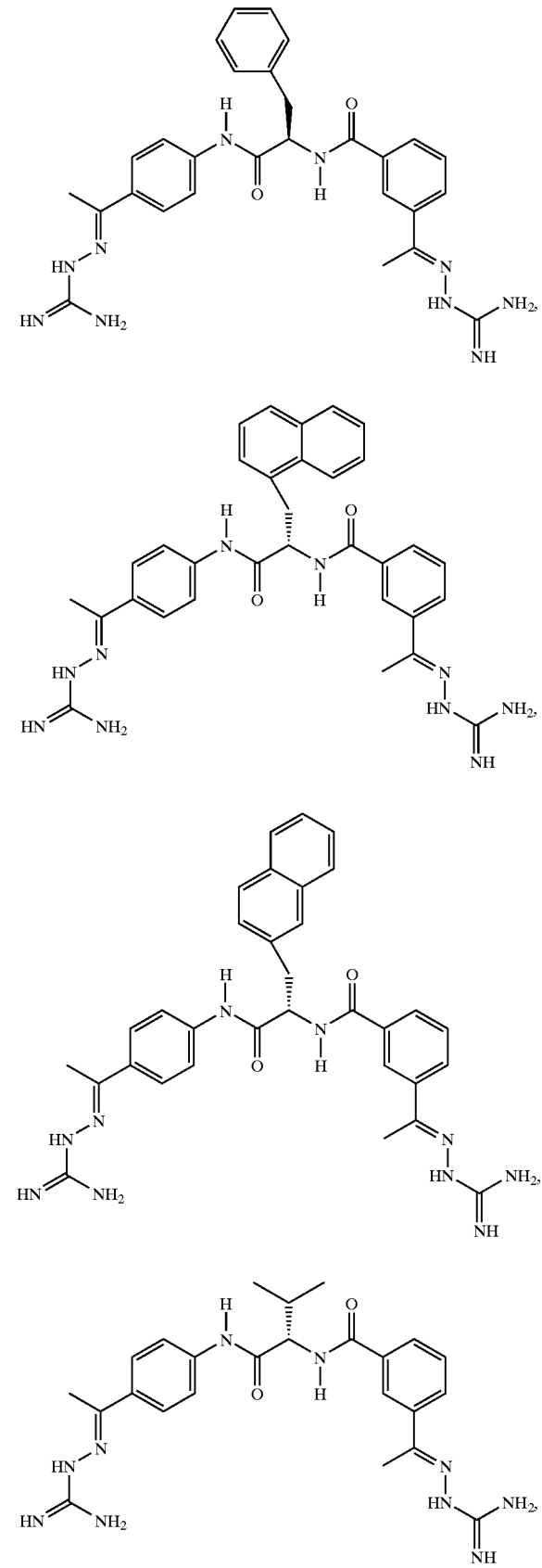

149
-continued
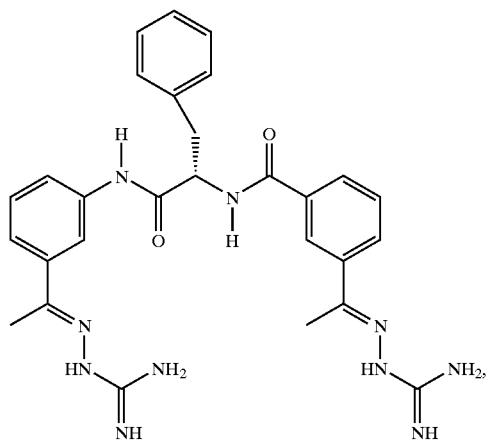
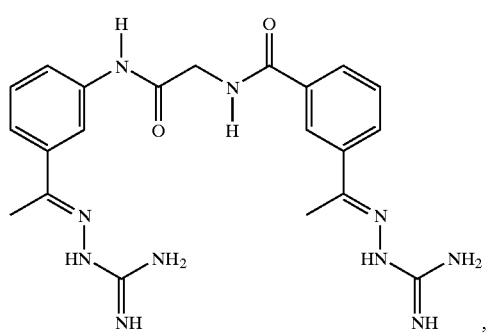
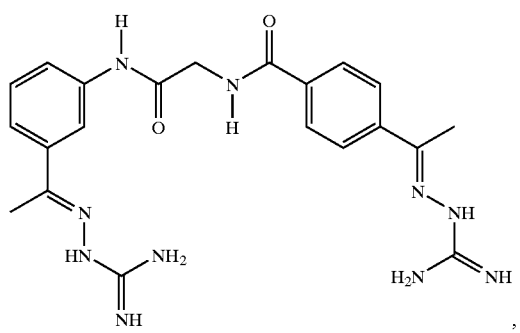
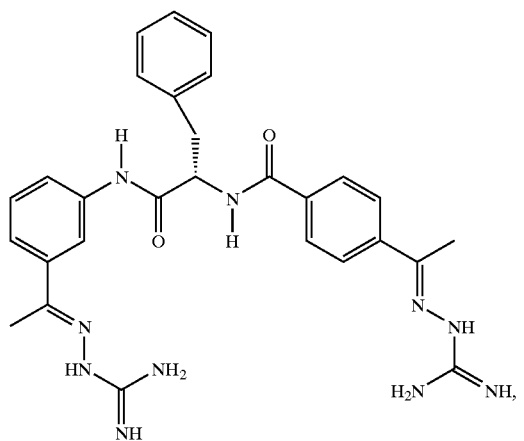
150
-continued
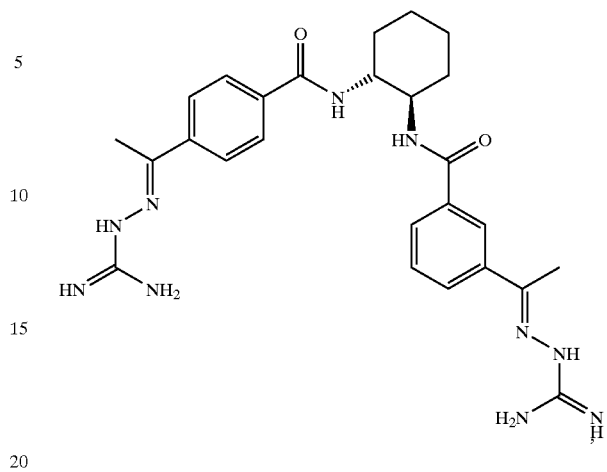
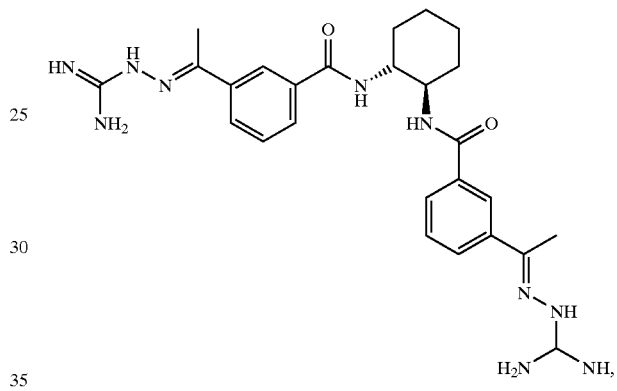
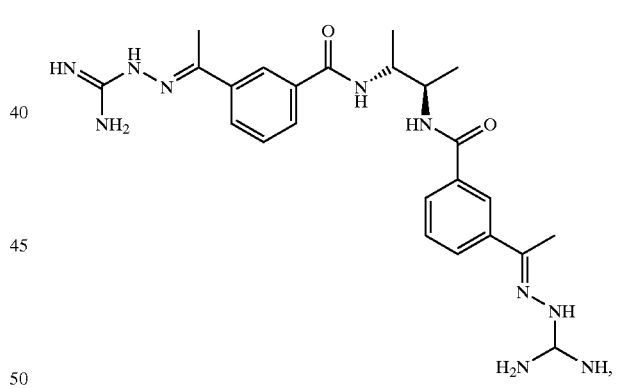
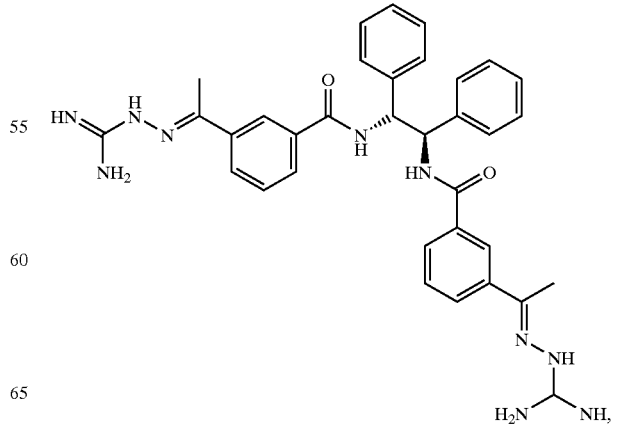

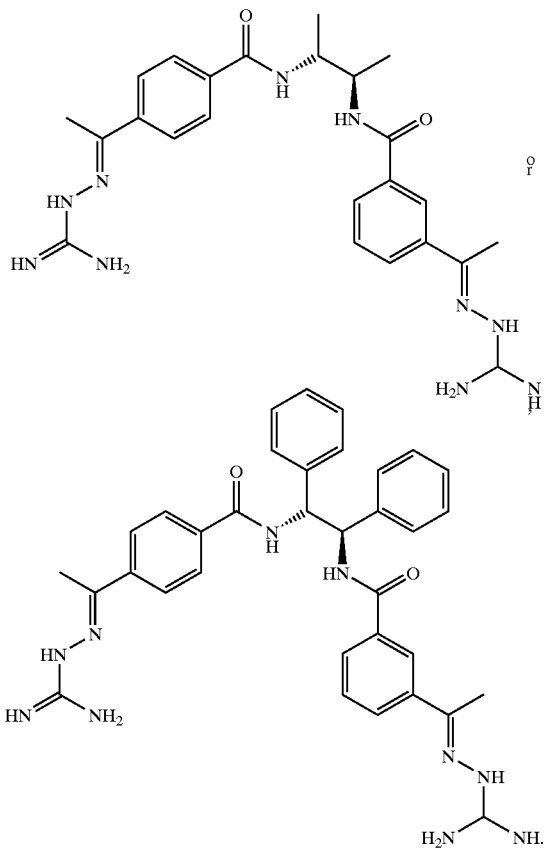

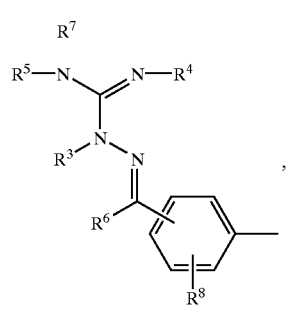

3. A method of killing or inhibiting the growth of bacteria, said method comprising contacting bacteria or a site susceptible to bacterial growth with a pharmaceutical composition comprising a pharmaceutically acceptable carrier and an effective amount of a compound of the formula I:

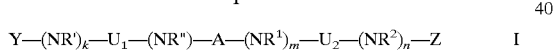    I or a derivative, salt, racemic mixture, mixture of E/Z isomers, or mixture of diastereomers thereof, wherein $U_1$ and $U_2$ are independently carbonyl, thiocarbonyl, or sulfonyl; k, l, m, and n are independently 0 or 1; A is a linker of 1, 2, 3, 4, 5, 6, 7, or 8 atoms that is optionally substituted with a group selected from alkyl, heteroalkyl, alkene, heteroalkene, alkyne, heteroalkyne, aryl, alkaryl, and heteroaryl; R', R'', $R^1$, and $R^2$ are independently H, alkyl, heteroalkyl, alkene, heteroalkene, alkyne, heteroalkyne, aryl, or heteroaryl; Y is selected from the group consisting of formulas II, III, IV, V, VI, VII, VIII, IX, and X:

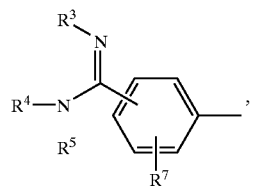   III

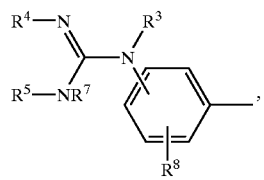   IV

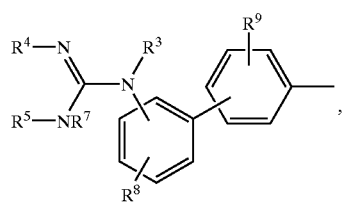   V

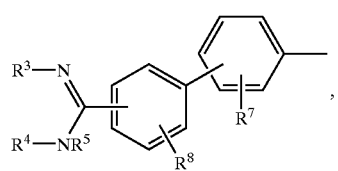   VI

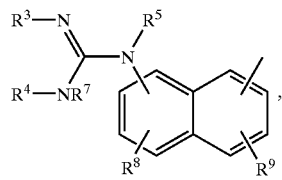   VII

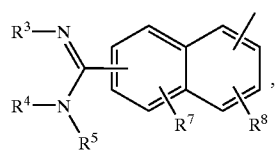   VIII

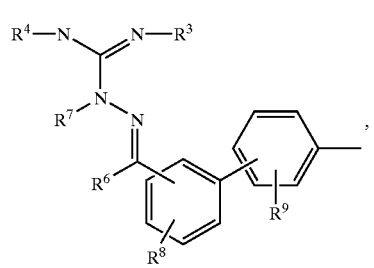   IX

X

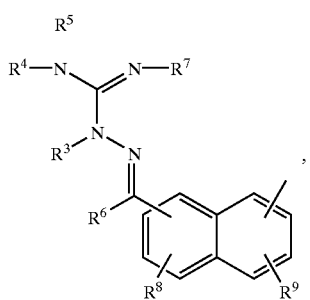

wherein each $R^3$, $R^4$, $R^5$, $R^7$, $R^8$, or $R^9$ is independently H, alkyl, aralkyl, heteroalkyl, alkene, heteroalkene, alkyne, heteroalkyne, aryl, or heteroaryl; and $R^6$ is H, or alkyl; and Z is

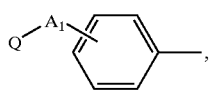

wherein $A_1$ is a bond or a linker of 1 or 2 atoms, and Q is aryl or heteroaryl.

4. A method of killing or inhibiting the growth of bacteria, said method comprising contacting bacteria or a site susceptible to bacterial growth with a pharmaceutical composition comprising a pharmaceutically acceptable carrier and an effective amount of a compound of the formula I:

$$Y-(NR')_k-U_1-(NR'')_l-A-(NR^1)_m-U_2-(NR^2)_n-Z \qquad I$$

or a derivative, salt, racemic mixture, mixture of E/Z isomers, or mixture of diastereomers thereof, wherein $U_1$ and $U_2$ are independently carbonyl, thiocarbonyl, or sulfonyl; k, l, m, and n are independently 0 or 1; A is a linker of 1, 2, 3, 4, 5, 6, 7, or 8 atoms that is optionally substituted with a group selected from alkyl, heteroalkyl, alkene, heteroalkene, alkyne, heteroalkyne, aryl, alkaryl, and heteroaryl; R', R", $R^1$, and $R^2$ are independently H, alkyl, heteroalkyl, alkene, heteroalkene, alkyne, heteroalkyne, aryl, or heteroaryl; Y is selected from the group consisting of formulas II, III, IV, V, VI, VII, VIII, and IX:

II

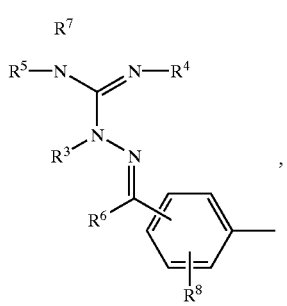

III

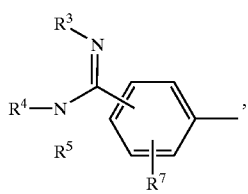

IV

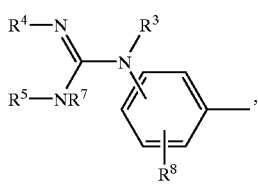

V

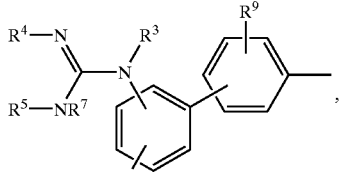

VI

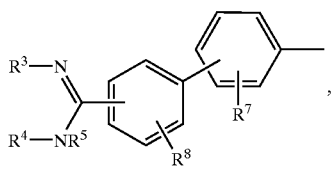

VII

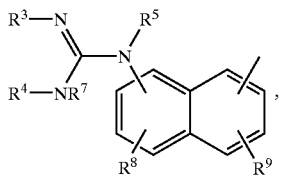

VIII

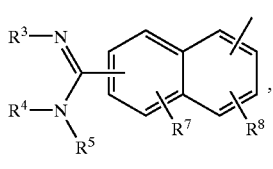

IX

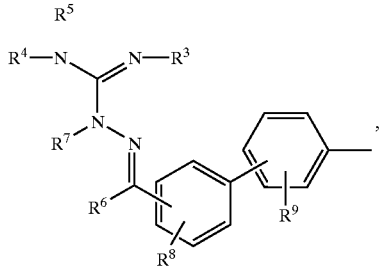

X

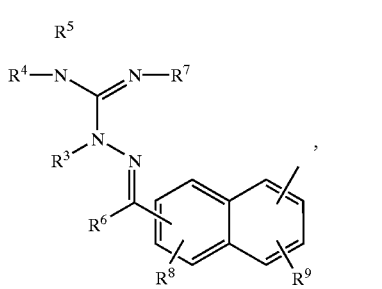

wherein each $R^3$, $R^4$, $R^5$, $R^7$, $R^8$, or $R^9$ is independently H, alkyl, aralkyl, heteroalkyl, alkene, heteroalkene, alkyne, heteroalkyne, aryl, or heteroaryl; and $R^6$ is H, alkyl, aralkyl, heteroalkyl, or aryl; and Z is selected from the group consisting of formulas XII, XIII, XIV XV, and XVI:

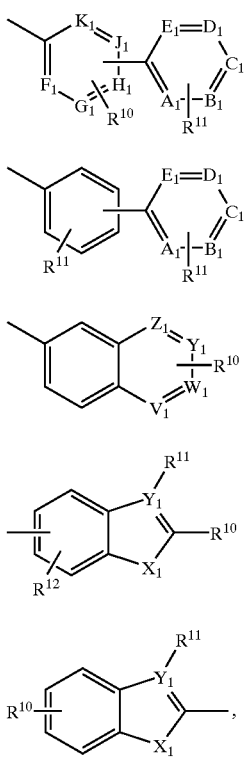

wherein $A_1$, $B_1$, $C_1$, $D_1$, $E_1$, $F_1$, $G_1$, $H_1$, $J_1$, $K_1$, $V_1$, $W_1$, and $Z_1$ are independently C, $CR^{13}$, or $NR^{14}$; $X_1$, is $CR^{15}$, $NR^{16}$, O, or S; $Y_1$ is C or N; and $R^{10}$, $R^{11}$, $R^{12}$, $R^{13}$, $R^{14}$, $R^{15}$, and $R^{16}$ are independently H, alkyl, aryl, amino, alkylamino, dialkylamino, hydroxy, alkoxy, nitro, or halogen.

5. The method of claim 4, wherein said compound is

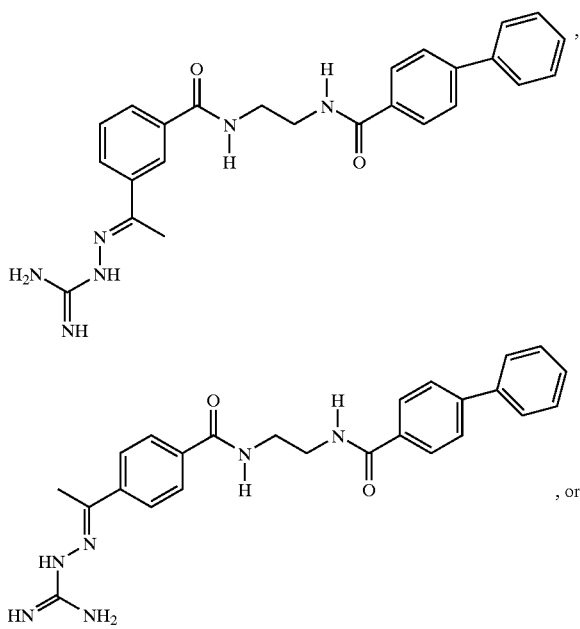

6. A method of killing or preventing the growth of bacteria, said method comprising contacting bacteria or a site susceptible to bacterial growth with a pharmaceutical composition comprising a pharmaceutically acceptable carrier and an effective amount of a compound of the formula XVIII:

XVIII

or a derivative, salt, racemic mixture, mixture of diastereomers thereof, wherein $R^1$ and $R^5$ are independently lower alkyl; $R^2$, $R^3$, and $R^4$, are independently H or lower alkyl; $R^6$ is aryl, heteroaryl or $C(O)R^7$, wherein $R^7$ is alkyl, aryl, or substituted allyl; X is $OR^8$, $SR^9$, or $NR^{10}R^{11}$, wherein $R^8$, $R^9$, and $R^{10}$, and $R^{11}$ are alkyl, alkenyl, or aryl, or X and $R^6$ taken together are a heterocyclic ring; and $Z^1$ and $Z^2$ are independently alkyl, aryl, alkenyl, alkynyl, halogen, cyano, nitro, or $OR^{12}$, wherein $R^{12}$ is alkyl, alkenyl, or aryl, or $SR^{13}$, where $R^{13}$ is alkyl, alkenyl, aryl, or $NR^{14}R^{15}$, where $R^{14}$ and $R^{15}$ are independently alkyl, alkenyl, or aryl, or $Z^1$ and $Z^2$ taken together form a ring that is optionally substituted.

7. The method of claim 6, wherein said compound is

-continued

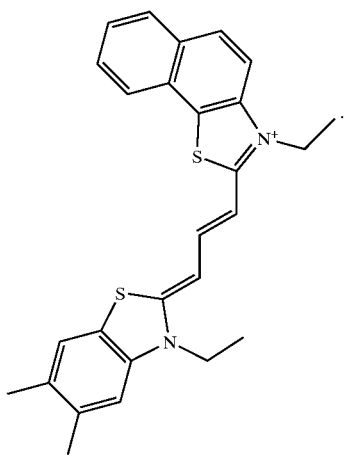

8. A method of killing or preventing the growth of bacteria, said method comprising contacting bacteria or a site susceptible to bacterial growth with a pharmaceutical composition comprising a pharmaceutically acceptable carrier and an effective amount of a compound of the formula XIX:

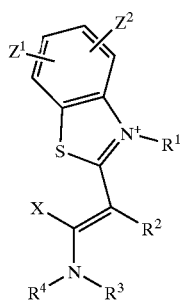

XIX or a derivative, salt, racemic mixture, or mixture of diastereomers thereof, wherein $R^1$ and $R^3$ are independently lower alkyl; $R^2$ is H or lower alkyl; $R^4$ is aryl, heteroaryl or $C(O)R^5$, wherein $R^5$ is alkyl, aryl, or substituted allyl; X is $OR^6$, $SR^7$, or $NR^8R^9$, wherein $R^6$, $R^7$, $R^8$, and $R^9$ are independently alkyl, alkenyl or aryl or X and $R^4$ taken together form a heterocyclic ring; and $Z^1$ and $Z^2$ are independently alkyl, aryl, alkenyl, alkynyl, halogen, cyano, nitro, or $OR^{10}$, where $R^{10}$ is alkyl, alkenyl, aryl, or $SR^{11}$, where $R^{11}$ is alkyl, alkenyl, aryl, or $NR^{12}R^{13}$, where $R^{12}$ and $R^{13}$ are independently alkyl, alkenyl, or aryl, or $Z^1$ and $Z^2$ taken together form a ring that is optionally substituted.

9. The method of claim 6, wherein said compound is

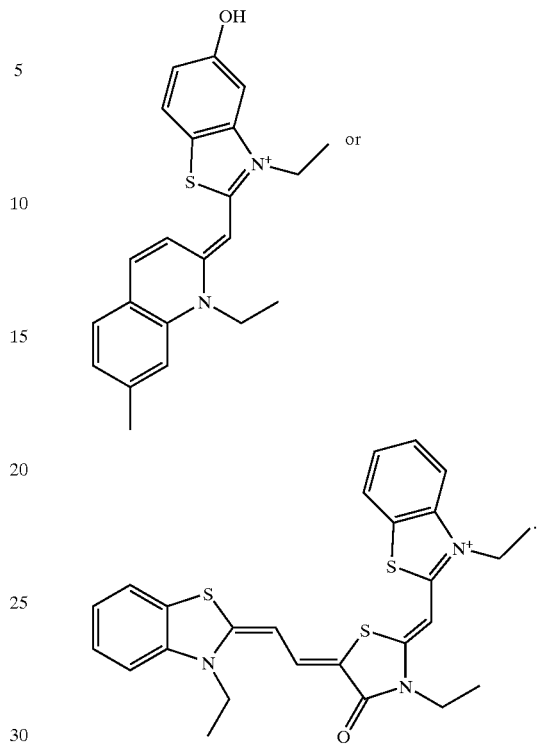

10. The method of any of claims 1–9, wherein said site susceptible bacterial growth is an in-dwelling device in a patient.

11. The method of any of claims 1–9, wherein said contacting comprises administering said pharmaceutical composition to a mammal.

12. The method of claim 11, wherein said administering is to the skin, hair, oral cavity, a mucous membrane, a wound, a bruise, a tooth, or an eye.

13. The method of any of claims 1–9, wherein said site susceptible to bacterial growth is a food, beverage, cosmetic, deodorant, contact lens product, food ingredient, enzyme compositions, a hard surface, or laundry.

14. The method of any of claims 1–10, wherein said compound inhibits a bacterial RNase P enzyme.

15. The method of claim 1, wherein Y is selected from the group consisting of formulas II, V, VI, VII, and VIII.

16. The method of claim 15, wherein Y is selected from the group consisting of formulas V, VI, VII, and VIII.

17. The method of claim 16, wherein Y is selected from the group consisting of formulas VA, VIA, VIB, VIIA, VIIB, VIIC, and VIIIA:

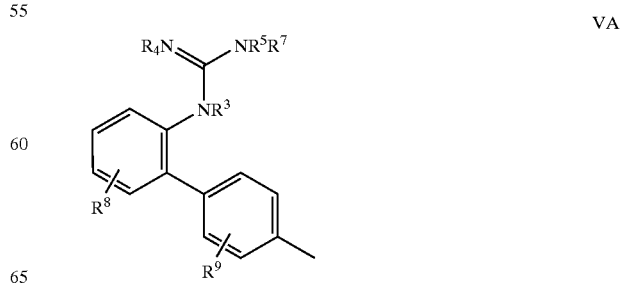

VA

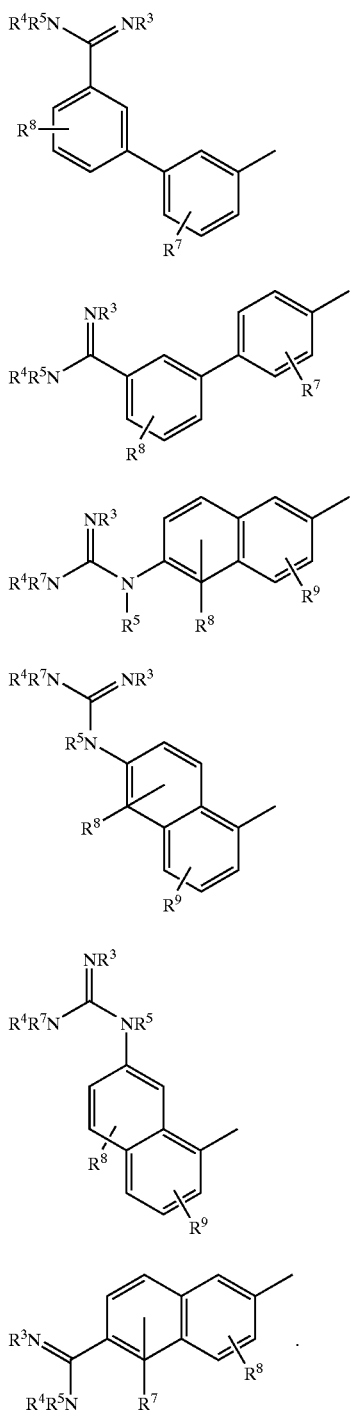

18. The method of claim 1, wherein A is —CH$_2$CH$_2$—, and k and n are 0.

19. The method of claim 3, wherein Y is selected from the group consisting of formulas II, V, VI, VII, and VIII.

20. The method of claim 3, wherein Y is selected from the group consisting of formulas V, VI, VII, and VIII.

21. The method of claim 4, wherein said compound has the formula:

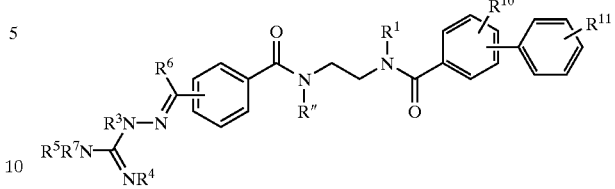

or a derivative, salt, racemic mixture, mixture of E/Z isomers, or mixture of diastereomers thereof.

22. The method of claim 21, wherein R$^1$, R$^3$, R$^4$, R$^5$, R$^7$, and R" are independently H, alkyl, aralkyl, heteroalkyl, or aryl; R$^6$ is H or alkyl; and R$^{10}$ and R$^{11}$ are independently H, halogen, hydroxy, alkoxy, amino, alkylamino, dialkylamino, alkyl, or nitro.

23. The method of claim 21, wherein R$^1$, R$^3$, R$^4$, R$^5$, R$^7$, and R" are independently H, alkyl, aralkyl, heteroalkyl, or aryl; R$^6$ is methyl, and R$^{10}$ and R$^{11}$ are independently H, halogen, hydroxy, alkoxy, amino, alkylamino, dialkylamino, alkyl, or nitro.

24. The method of claim 4, wherein said compound has the formula:

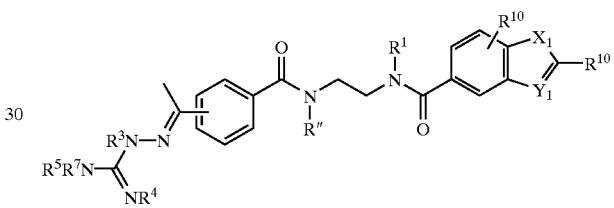

or a derivative, salt, racemic mixture, mixture of E/Z isomers, or mixture of diastereomers thereof.

25. The method of claim 24, wherein R$^1$, R$^3$, R$^4$, R$^5$, and R" are independently H, alkyl, aralkyl, heteroalkyl, or aryl; R$^7$ is H, halogen, hydroxy, alkoxy, amino, alkylamino, dialkylamino, alkyl, or nitro; X$_1$ is CR$^{15}$, NR$^{16}$, O or S; and Y$_1$ is CH or N; and R$^{10}$, R$^{12}$, R$^{15}$, and R$^{16}$ are independently H, alkyl, or aryl.

26. The method of claim 4, wherein said compound has the formula:

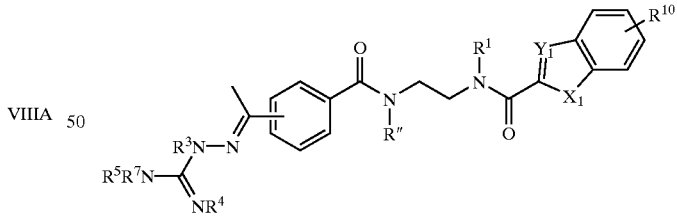

or a derivative, salt, racemic mixture, mixture of E/Z isomers, or mixture of diastereomers thereof.

27. The method of claim 26, wherein R$^1$, R$^3$, R$^4$, R$^5$, R$^7$, and R" are independently H, alkyl, aralkyl, heteroalkyl, or aryl; R$^{10}$ is H, halogen, hydroxy, alkoxy, amino, alkylamino, dialkylamino, alkyl, nitro, aryl, or heteroaryl; X$_1$ is O, S, or NR$^{16}$; Y$_1$ is N or CR$^{11}$, where R$^{11}$ and R$^{16}$ are independently H, alkyl, or aryl.

* * * * *